US012031139B2

(12) United States Patent
Reeves et al.

(10) Patent No.: US 12,031,139 B2
(45) Date of Patent: Jul. 9, 2024

(54) STABLE TRANSFORMATION OF A POPULATION AND A METHOD OF BIOCONTAINMENT USING HAPLOINSUFFICIENCY AND UNDERDOMINANCE PRINCIPLES

(71) Applicant: MAX-PLANCK-GESELLSCHAFT ZUR FÖRDERUNG DER WISSENSCHAFTEN E.V., Munich (DE)

(72) Inventors: Guy Reeves, Hamburg (DE); Floyd Reed, Kapolei, HI (US)

(73) Assignee: MAX-PLANCK-GESELLSCHAFT ZUR FORDERUNG DER WISSENSCHAFTEN E.V., Munich (DE)

( * ) Notice: Subject to any disclaimer, the term of this patent is extended or adjusted under 35 U.S.C. 154(b) by 1305 days.

(21) Appl. No.: 16/538,602

(22) Filed: Aug. 12, 2019

(65) Prior Publication Data

US 2020/0093084 A1    Mar. 26, 2020

Related U.S. Application Data

(62) Division of application No. 14/654,450, filed as application No. PCT/EP2013/077856 on Dec. 20, 2013, now abandoned.

(60) Provisional application No. 61/740,359, filed on Dec. 20, 2012.

(30) Foreign Application Priority Data

Dec. 20, 2012    (GB) ...................................... 1223097

(51) Int. Cl.
| | | |
|---|---|---|
| *C12N 15/113* | (2010.01) | |
| *A01K 67/033* | (2006.01) | |
| *C12N 15/82* | (2006.01) | |

(52) U.S. Cl.
CPC ........ *C12N 15/8218* (2013.01); *A01K 67/033* (2013.01); *A01K 67/0333* (2013.01); *A01K 67/0339* (2013.01); *C12N 15/113* (2013.01); *A01K 2207/05* (2013.01); *A01K 2217/15* (2013.01); *A01K 2227/706* (2013.01); *A01K 2267/02* (2013.01); *C12N 2310/14* (2013.01)

(58) Field of Classification Search
CPC ............ A01K 67/0333; A01K 67/0339; A01K 2217/15; A01K 2227/706; C12N 15/113; C12N 2310/14
See application file for complete search history.

(56) References Cited

U.S. PATENT DOCUMENTS

| | | |
|---|---|---|
| 7,612,255 B2 | 11/2009 | Gressel |
| 2005/0120395 A1 | 6/2005 | Burt |
| 2008/0125384 A1 | 5/2008 | Yang |
| 2008/0134351 A1 | 6/2008 | Sanchez-Fernandez |
| 2014/0298539 A1 | 10/2014 | Loque |

OTHER PUBLICATIONS

Taurog, (1988, J. Immunology, 141:4020-4023). (Year: 1988).*
Mullins et al (1989, EMBO, 8:4065-4072) (Year: 1989).*
Mullins (Nature, 1990, 344:541-544) (Year: 1990).*
Hammer et al (Cell, 1990, 63:1099-1112) (Year: 1990).*
Elbashir et al (Genes Dev. Jan. 15, 2001;15(2):188-200) (Year: 2001).*
Hasuwa et al (FEBS Lett. 2002; 532(1-2): 227-30) (Year: 2002).*
Tiscornia G, (Proc Natl Acad Sci U S A. 2003; 100(4): 1844-8) (Year: 2003).*
Carmell MA (Nat Struct Biol. 2003; 10(2): 91-92). (Year: 2003).*
Qi et al (Hypertension, 2005, 45:1004-1011) (Year: 2005).*
ATRPS5A Gene, Locus NM_180233, Jun. 2006.
Altrock, Philipp M., et al., "Stability Properties of Underdominance in Finite Subdivided Populations", PLoS Computational Biology, vol. 7, Issue 11, e1002260, Nov. 2011.
Altrock, Philipp M., et al., "Using Underdominance to Bi-Stably Transform Local Populations", Journal of Theoretical Biology, vol. 267, pp. 62-75, 2010.
Asman, S.M., et al., "Field Studies of Genetic Control Systems for Mosquitoes" Annual Review of Entomology, vol. 26, pp. 289-318, 1981.
Barakat, Abdelali, et al., "The Organization of Cytoplasmic Ribosomal Protein Genes in the *Arabidopsis* Genome", Plant Physiol. vol. 127, pp. 398-415, 2001.

(Continued)

*Primary Examiner* — J. E. Angell
(74) *Attorney, Agent, or Firm* — BURNS & LEVINSON, LLP; Daniel W. Clarke

(57) ABSTRACT

The present invention relates to a method for reducing the competitive fitness of an organism hemizygous for a transgenic locus compared to the organism homozygous for the transgenic locus comprising the steps of: (a) reducing the expression of a haploinsufficient gene in the organism, wherein said reduction is conveyed by a transgenic locus in the organism; and (b) rescuing the reduced expression in the organism, wherein said rescue is conveyed by the same transgenic locus in the organism, yielding an organism which is less competitively fit if hemizygous for the transgenic locus than if homozygous for the transgenic locus. The present invention also relates to a method for decreasing the introgression of a transgenic locus in an organism into a population of otherwise interfertile sexually reproducing organisms comprising the steps of: (a) reducing the expression of a haploinsufficient gene in the organism, wherein said reduction is conveyed by a transgenic locus in the organism; (b) rescuing the reduced expression in the organism, wherein said rescue is conveyed by the same transgenic locus in the organism, and (c) using a transgenic organism obtained in step (b) in an environment comprising otherwise interfertile sexually reproducing wildtype individuals of the organism, wherein the competitive fitness of hemizygous progeny is reduced, thereby decreasing the rate of sexually reproduction and/or viability and/or the competitive fitness of hemizygous progeny. Further envisaged are corresponding genetic systems and genetically modified organisms.

11 Claims, 13 Drawing Sheets

Specification includes a Sequence Listing.

(56) References Cited

OTHER PUBLICATIONS

Casanova-Saez, Ruben, et al., "Combined Haploinsufficiency and Purifying Selection Drive Retention of RPL36a Paralogs in *Arabidopsis*", Scientific Reports, pp. 1-7, published Feb. 18, 2014.
Chen, Chun-Hong, et al., "A Synthetic Maternal-Effect Selfish Genetic Element Drives Population Replacement in Drosophila", Science, vol. 316, pp. 597-600, Apr. 27, 2007.
Chen, Wei, et al., "Haploinsuffciency for Znf9 in Znf9+/- Mice is Associated with Multiorgan Abnormalities Resembling Myotonic Dystrophy", J. Mol. Biol., vol. 368, No. 1, pp. 8-17, 2007.
Curtis, C. F., "Possible Use of Translocations to Fix Desirable Genes in Insect Pest Populations", Nature, vol. 218, pp. 368-369, Apr. 27, 1968.
Davis, Stephen, et al., "Engineered Underdominance Allows Efficient and Economical Introgression of Traits into Pest Populations", J. Theor. Biol., vol. 212, No. 1, pp. 83-98, 2001.
Enerly, Espen, et al., "Silencing the Drosophila Ribosomal Protein L14 Gene Using Targeted RNA Interference Causes Distinct Somatic Anomalies", Gene, vol. 320, pp. 41-48, 2003.
Flygare, Johan, et al., "Deficiency of Ribosomal Protein S19 in CD34+ Cells Generated by siRNA Blocks Erythroid Development and Mimics Defects Seen in Diamond-Blackfan Anemia", Blood, vol. 105, No. 12, pp. 4627-4634, 2005.
Gong, Peng, et al., "A Dominant Lethal Genetic System for Autocidal Control of the Mediterranean Fruitfly", Nature Biotechnology, vol. 23, No. 4, pp. 453-456, Apr. 2005.
Gressel, Jonathan, et al., "Mitigating Transgene Flow from Crops", Vt. Articles, pp. 1-5, Feb. 2006.
Howell, Gareth R., et al., "Transgenic Rescue of the Mouse t Complex Haplolethal locus Thl1", Mammalian Genome, vol. 16, pp. 838-846, 2005.
Ito, Takuya, et al., "Disruption of an *Arabidopsis* Cytoplasmic Ribosomal Protein S13-Homologous Gene by Transposon-Mediated Mutagenesis Causes Aberrant Growth and Development", The Plant Journal, vol. 22(3), pp. 257-264, 2000.
Magori, Krisztian, et al., "Genetically Engineered Underdominance for Manipulation of Pest Populations: A Deterministic Model", Genetics, vol. 172, pp. 2613-2620, Apr. 2005.
Marshall, John M., et al., "Inverse Medea as a Novel Gene Drive System for Local Population Replacement: A Theoretical Analysis", Journal of Heredity, vol. 102, No. 3, pp. 336-341, 2011.
Marygold, Steven J., "The Ribosomal Protein Genes and Minute Loci of Drosophila Melanogaster", Genome Biology, vol. 8, Issue 10, pg. R216-R216.26, 2007.
Revenkov, Ekaterina, et al., "Involvement of *Arabidopsis thaliana* Ribosomal Protein S27 in mRNA Degradation Triggered by Genotoxic Stress", The EMBO Journal, vol. 18, No. 2, pp. 490-499, 1999.
Saeboe-Larssen, S., et al., "The *Drosophila* Ribosomal Protein L14-Encoding Gene, Identified by a Novel Minute Mutation in a Dense Cluster of Previously Undescribed Genes in Cytogenetic Region 66D", Molecular and General Genetics, vol. 255, pp. 141-151, 1997.
Weijers, Dolf, et al., "An *Arabidopsis* Minute-Like Phenotype Caused by a Semi-Dominant Mutation in a Ribosomal Protein S5 Gene", Development 128, pp. 4289-4299, 2001.
Windbichler, Nikolai, et al., "A Synthetic Homing Endonuclease-Based Gene Drive System in the Human Malaria Mosquito" Nature, vol. 473, pp. 212-215, May 12, 2011.
Windbichler, Nikolai, et al., "Targeting the X Chromosome During Spermatogenesis Induces Y Chromosome Transmission Ratio Distortion and Early Dominant Embryo Lethality in Anopheles Gambiae", PLoS Genetics, vol. 4, Issue 12, e1000291, Dec. 2008.
International Search Report dated Feb. 26, 2014, PCT/EP2013/077856.

\* cited by examiner

FIGURE 3

```
                               Block A
RpL14.dsRNA  CCTTTCGAGAGATTCGTACAAACTGGTCGCATTGCCAAGGC
             |||||||||||||||||||||||||||||||||||||||||
RpL14[+]     CCTTTCGAGAGATTCGTACAAACTGGTCGCATTGCCAAGGC
             || ||||||| | ||||| ||||| || ||||| ||||| ||
RpL14[r]     CCCTTCGAGCGCTTCGTGCAAACAGGCCGCATCGCCAAAGC Linker
RpL14.dsRNA  _____AGGTACCA_____

RpL14[+]     CTCCGCCGGTCCCCTGAAGGGGCGCCTGGT
             ||||||||||||||||||||||||||||||
RpL14[r]     CTCCGCCGGTCCCCTGAAGGGGCGCCTGGT

Block B
RpL14.dsRNA  GGCCATTGTCGACGTCATTGACCAAAACAGA      (SEQ ID NO: 15)
             |||||||||||||||||||||||||||||||
RpL14[+]     GGCCATTGTCGACGTCATTGACCAAAACAGA      (SEQ ID NO: 16)
             ||||| ||||| ||||| ||||| |||||
RpL14[r]     CGCCATCGTCGATGTCATCGACCAGAACAGG      (SEQ ID NO: 17)
```

FIGURE 12 miRNA1

| | |
|---|---|
| miRNA1 sensitive | ATGCCTATAACTGGTAAGTAA (SEQ ID NO: 18) |
| RpL23aA insensitive | AAGCCTAGAACTGGTAAGTAC (SEQ ID NO: 19) |
| Rescue | AAGCCACGTACCGGAAAGTAC (SEQ ID NO: 20) |
| RpL23aB | GTTCCTAGAAAGCCTAAGTAC (SEQ ID NO: 21) | miRNA2

| | |
|---|---|
| miRNA2 sensitive | TAGCCTTACGTGAGGCTTACA (SEQ ID NO: 22) |
| RpL23aA insensitive | AAGGCTTACGTGAGGCTTACA (SEQ ID NO: 23) |
| Rescue | AAGGCTTATGTTAGGTTGACA (SEQ ID NO: 24) |
| RpL23aB | AAGGCGTATGTGAGGTTGACT (SEQ ID NO: 25) |

STABLE TRANSFORMATION OF A POPULATION AND A METHOD OF BIOCONTAINMENT USING HAPLOINSUFFICIENCY AND UNDERDOMINANCE PRINCIPLES

CROSS-REFERENCE TO RELATED APPLICATIONS

This application is a divisional application of U.S. Ser. No. 14/654,450, filed Jun. 19, 2015, which is a national phase application, filed under 35 U.S.C. § 371 of PCT International Application No. PCT/EP2013/077856, filed Dec. 20, 2013, which claims the benefit of priority under 35 U.S.C. § 119(a) to Great Britain Application No. 1223097.5, filed Dec. 20, 2012 and U.S. Application No. 61/740,359, filed Dec. 20, 2012, the entire contents of each of which are incorporated herein by reference.

FIELD OF THE INVENTION

The present invention relates to a method for reducing the competitive fitness of an organism hemizygous for a transgenic locus compared to the organism homozygous for the transgenic locus comprising the steps of: (a) reducing the expression of a haploinsufficient gene in the organism, wherein said reduction is conveyed by a transgenic locus in the organism; and (b) rescuing the reduced expression in the organism, wherein said rescue is conveyed by the same transgenic locus in the organism, yielding an organism which is less competitively fit if hemizygous for the transgenic locus than if homozygous for the transgenic locus. The present invention also relates to a method for decreasing the introgression of a transgenic locus in an organism into a population of otherwise interfertile sexually reproducing organisms comprising the steps of: (a) reducing the expression of a haploinsufficient gene in the organism, wherein said reduction is conveyed by a transgenic locus in the organism; (b) rescuing the reduced expression in the organism, wherein said rescue is conveyed by the same transgenic locus in the organism, and (c) using a transgenic organism obtained in step (b) in an environment comprising otherwise interfertile sexually reproducing wildtype individuals of the organism, wherein the competitive fitness of hemizygous progeny is reduced, thereby decreasing the rate of sexually reproduction and/or viability and/or the competitive fitness of hemizygous progeny. Further envisaged are corresponding genetic systems and genetically modified organisms.

BACKGROUND OF THE INVENTION

Genetic underdominance arises when heterozygotes or hemizygotes have lower fitness than homozygotes. Historically a number of applications exploiting genetic underdominance have been proposed and include (i) Biocontainment: to limit unintentional introgression between sexually reproducing organisms in the environment, (ii) Population transformation: to push to high frequency desirable genes in wild populations of sexually reproducing organisms, and (iii) Suppression of the size of wild pest populations: artificial releases of large numbers of homozygotes over several generations can be used to reduce the size of the next generation of the wild population. The generation of transgenic loci which are underdominant that would permit the implementation of these approaches is technically challenging and remains to be achieved in a manner which permits the flexibility to be used in a wide range of applications and species.

The exploitation of underdominance in biocontainment has been considered mainly in the context of limiting the accidental introgression of transgenes from varieties of genetically modified plants into wild relatives or other cultivar varieties (see, for example, isb.vt.edu/articles/feb0603.htm). Only one underdominant has been implemented however this approach is inflexible, being limited to Brassica species and reliant on unidentified genes distributed throughout the genome. A number of other biocontainment approaches that do not rely on underdominance have been envisaged or implemented, however the applied value of all these approaches remains to be tested in commercial applications. There is a strong need for the development of flexible biocontainment mechanisms which will not significantly impact the agronomic value of plant varieties (Plant gene containment. 224 (Wiley-Blackwel: 2012). This need is driven primarily important for three applications, (1) the field testing of novel experimental plants, (2) facilitating the commercial production of uncontaminated seed by vendors, and (3) the commercial planting of genetically modified plants outside glasshouses.

The exploitation of underdominance in population transformation (also termed population replacement) was proposed by in 1968 by Curtis, (Nature 218, 368-69 (1968)). In this scientific publication Curtis used the example of underdominance to show how disease refractory genes could be sustainably driven at high frequency into wild populations (even if they are not selectively advantageous) through the release of homozygous underdominant stocks of the same species. It was envisaged that genes which rendered insects refractory to spreading diseases to humans, livestock and plants could be driven into wild population where they could they remain in a self-sustaining manner. A number of approaches have been proposed to achieve population transformation which can be described as underdominant but remain to be implemented (e.g. Davis et al. Journal of theoretical biology, 212, 83-98 (2001); and Marshall and Hay, The Journal of heredity, 102, 336-41 (2011)). Alternative approaches which are not described as relying on an underdominance have been implemented in laboratory populations of insects but none have been tested in wild populations (e.g. Chen et al., Science 316, 597 (2007) and Windbichler et al., Nature (2011); doi:10.1038/nature09937). There is thus a clear need to develop and improve population transformation systems, which could be used to control diseases as it is unlikely that a single system will have ideal properties for all the very wide range of potential applications. Of particular value would be the development of systems that can readily be transferred between species.

The exploitation of underdominance in population transformation has been in development since the 1940s. If hemizygous progeny are partially inviable or infertile then the large scale release of the appropriate homozygous stock can be used to reduce the size of the next generation of the wild population. Considerable effort was made from 1960-1980 to develop appropriate underdominant stocks in a wide range of species using radiation induced chromosomal rearrangements (Asman et al., Annual Review of Entomology 26, 289-318 (1981). However, this approach to generating underdominant stocks proved to be inflexible and only marginally effective and was largely abandoned. Currently, wild populations of insect pests are suppressed using mass releases of a radiation-sterilized individuals as part of the 'sterile insects technique' in numerous pest suppression programs around the world (Dyck et al., Sterile Insect Technique. 760; Springer-Verlag: Berlin/Heidelberg, 2005). Despite the success of this approach, there are a number of limitations in terms of the efficiency or radiation based approaches that might be addressed using transgenic stocks. These include reducing the costs of production of large numbers of individuals for release, particularly if sex sorting in required, and potential improvements in the competitive fitness of released individuals. This had led to the development of a small number of system which could be used in insect population suppression (e.g. Windbichler et al., PLoS genetics 4, (2008) and Fu et al., Nature 23, 453-456 (2005)). Yet there is still a clear need to further develop and improve population suppression systems as it is unlikely that a single system will have ideal properties for the wide range of potential applications that might be useful. Of particular value would be the development of further systems that can readily be transferred between species.

OBJECTS AND SUMMARY OF THE INVENTION

The present invention addresses this need and provides means and methods, which allow the reduction of the competitive fitness of an organism hemizygous for a transgenic locus compared to the organism homozygous for the transgenic locus, with the proviso that the organism is not a human being. This objective is accomplished by a method comprising the steps of: (a) reducing the expression of a haploinsufficient gene in the organism, wherein said reduction is conveyed by a transgenic locus in the organism; and (b) rescuing the reduced expression in the organism, wherein said rescue is conveyed by the same transgenic locus in the organism, yielding an organism which is less competitively fit if hemizygous for the transgenic locus than if homozygous for the transgenic locus.

This alternative type of underdominance system based on haploinsufficiency that is contained within a single locus or gene region can be recombined onto different genetic backgrounds and does not affect chromosomal structure. Surprisingly, the transgenic homozygote has a high enough fitness relative to wildtype homozygotes and hemizygotes for underdominant effects with robust dynamics. Such a haploinsufficiency based underdominance system thus allows one to effectively and stably transform populations of sexually reproducing organisms.

The provided underdominance methodology offers several advantages and has a wide range of potential uses, which is facilitated by the extent to which it can be used in a range of species. The methodology can, for example, be used for biocontainment to limit the spread of genetically modified genes into traditional crops or wild relative species. The provided underdominance methodology can also be used as part of a population transformation strategy to render insect populations that are vectors of human, livestock or plant diseases refractory to disease transmission. The concept can additionally be applied to vectors of disease that are not insects and to diseases that affect other species, e.g. endangered species that are threatened by non-native diseases and vectors (Warner, R. E., 1968, Condor 70:101-120). Underdominance can further be combined with engineered gene-drive systems to improve their properties in terms of safety and reversibility. A further advantage of the presently described methodology is the fact that using underdominance to transform a population means that the transformation is potentially reversible over a wide range of realistic circumstances. Thus, releases of individuals that carry the alternative wildtype allele at the transgenic locus in sufficient numbers can re-cross the allele frequency threshold and the transgenic allele is expected to be completely removed from the population over the following generations, along with linked effector genes. Thus, if desired, the population can theoretically be returned to a completely wildtype state. Furthermore, populations transformed according to the presently described underdominance methodology are expected to be geographically stable. Rare migrants, both into and out of a transformed region, will tend to have hemizygous offspring with reduced fitness. In consequence, the migrant alleles will tend to be removed by natural selection and, if migration rates are sufficiently low (Altrock et al., 2010, Journal of Theoretical Biology 267: 62-75), a transgenic construct is not expected to spread uncontrolled from population to population. The provided underdominance methodology can also be used to improve the efficiency of population suppression techniques. Population suppression may thus advantageously be used to facilitate population transformation by reducing the size of the wild target population.

In a preferred embodiment, the method additionally comprises the step of releasing a transgenic organism obtained in step (b) into a population of the same species such that a transgenic construct is established at a high frequency at a locus in the population.

In another preferred embodiment the method additionally comprises the step of using a transgenic organism obtained in step (b) in an environment comprising otherwise interfertile sexually reproducing wildtype individuals of the organism, whereby the competitive fitness of hemizygous progeny is reduced.

In a further aspect the invention relates to a method for the transformation of a population of sexually reproducing organisms, with the proviso that said organism is not a human being, comprising the steps of: (a) reducing the expression of a haploinsufficient gene in the organism, wherein said reduction is conveyed by a transgenic locus in the organism; (b) rescuing the reduced expression in the organism, wherein said rescue is conveyed by the same transgenic locus in the organism, and (c) releasing homozygous organisms obtained in the preceding step into a population of the same species such that the transgenic locus is established at a high frequency in the population.

In a preferred embodiment, said releasing step comprises the release, in a single or over multiple generations, of sufficient relative numbers of organisms to result in a frequency in population of the same species greater than the unstable allelic equilibrium frequency predicted by the competitive fitness.

In a further aspect the prevent invention relates to a method for decreasing the introgression of a transgenic locus in an organism into a population of otherwise interfertile sexually reproducing organisms, with the proviso that said organism is not a human being, comprising the steps of: (a) reducing the expression of a haploinsufficient gene in the organism, wherein said reduction is conveyed by a transgenic locus in the organism; (b) rescuing the reduced expression in the organism, wherein said rescue is conveyed by the same transgenic locus in the organism; and (c) using a transgenic organism obtained in step (b) in an environment comprising otherwise interfertile sexually reproducing wildtype individuals of the organism, wherein the competitive fitness of hemizygous progeny is reduced, thereby decreasing the rate of sexually reproduction and/or viability of hemizygous progeny.

In yet another aspect the present invention relates to a method for reducing the size of wild populations of otherwise interfertile sexually reproducing organisms, with the proviso that said organism is not a human being, comprising the steps of: (a) reducing the expression of a haploinsufficient gene in the organism, wherein said reduction is conveyed by a transgenic locus in the organism; (b) rescuing the reduced expression in the organism, wherein said rescue is conveyed by the same transgenic locus in the organism, and (c) using a hemizygous transgenic organism obtained in step (b) or a mixture of homozygous and hemizygous transgenic organisms obtained in step (b) in an environment comprising otherwise interfertile sexually reproducing wildtype individuals of the organism, wherein the competitive fitness of hemizygous progeny is reduced, thereby decreasing the rate of sexually reproduction and/or viability of hemizygous progeny.

In a preferred embodiment of the methods as defined herein above, said reduced competitive fitness in hemizygous progeny is non-viability and/or non-fertility of the organism.

In a further preferred embodiment said decrease of introgression of a transgenic locus in an organism as mentioned herein above is a prevention of introgression of a transgenic locus and wherein the reduction of competitive fitness of a hemizygous progeny eliminates or limits the sexual reproduction of hemizygous progeny.

In a further preferred embodiment said reducing the expression of a haploinsufficient gene comprises the provision of a means which specifically degrades or directly inactivates the haploinsufficient gene transcript or expression product, or which specifically disrupts the haploinsufficient gene DNA sequence.

In yet another preferred embodiment said specifically degrading or inactivating agent comprises a siRNA, miRNA, an antisense RNA molecule, an antisense DNA molecule or an agent conveying RNA-directed DNA methylation.

In another preferred embodiment said means, which specifically disrupts said haploinsufficient gene DNA sequence is a zinc finger nucleases, a Transcription Activator-Like Effector Nuclease (TALEN), CRISPR or a meganuclease.

In a further preferred embodiment said rescuing the expression of a haploinsufficient gene comprises a modification of the haploinsufficient gene sequence. In a specific embodiment, the modified haploinsufficient gene may be based on an ortholog or paralog sequence. Said modification of the haploinsufficient gene preferably comprises the provision of an at least partial rescue to a means, which specifically degrades or directly inactivates the haploinsufficient gene transcript or expression product, or which specifically disrupts the haploinsufficient gene DNA sequence; or the use of an ortholog or paralog sequence.

In a further preferred embodiment said transgenic locus comprises an underdominant construct. Said underdominant construct preferably comprises a sequence leading to the provision of a means which specifically degrades or directly inactivates the haploinsufficient gene transcript or expression product, or which specifically disrupts the haploinsufficient gene DNA sequence.

In a further preferred embodiment a method of the invention comprises the transformation of the organism with an underdominant construct comprising a sequence leading to the provision of a means which specifically degrades or directly inactivates the haploinsufficient gene transcript or expression product, or which specifically disrupts the haploinsufficient gene DNA sequence. In a particularly preferred embodiment, said underdominant construct comprises a sequence leading to the provision of siRNA, miRNA, or an antisense RNA or DNA molecule, or the expression of a zinc finger nucleases, a Transcription Activator-Like Effector Nuclease (TALEN), CRISPR or a meganuclease activity.

In yet another preferred embodiment, said sequence leading to the provision of a means which specifically degrades or directly inactivates the haploinsufficient gene transcript or expression product, or which specifically disrupts the haploinsufficient gene DNA sequence comprises disruptive sequences flanked by site specific recognition sites for a recombinase, preferably Cre or FLP, allowing to render said sequence, which leads to the provision of a means which specifically degrades or directly inactivates the haploinsufficient gene transcript or expression product, inactive.

In yet another preferred embodiment, said sequence leading to the provision of a means which specifically degrades or directly inactivates the haploinsufficient gene transcript or expression product, or which specifically disrupts the haploinsufficient gene DNA sequence, is inactivated by in vivo exposure of said recombinase, preferably Cre or FLP.

In a further preferred embodiment, said underdominant construct additionally comprises a modified version of the haploinsufficient gene, which is resistant to a means which specifically degrades or directly inactivates the haploinsufficient gene transcript or expression product, or which specifically disrupts the haploinsufficient gene DNA sequence.

In yet another preferred embodiment, said method comprises the initial transformation of the organism with an independent transgenic construct comprising a modified version of the haploinsufficient gene, which is resistant to a means which specifically degrades or directly inactivates the haploinsufficient gene transcript or expression product, or which specifically disrupts the haploinsufficient gene DNA sequence, followed by the transformation of the organism with an underdominant construct comprising a sequence leading to the provision of a means which specifically degrades or directly inactivates the haploinsufficient gene transcript or expression product, or which specifically disrupts the haploinsufficient gene DNA sequence and a haploinsufficient gene that comprises the provision of an at least partial rescue to a means which specifically degrades or directly inactivates the haploinsufficient gene transcript or expression product, or which specifically disrupts the haploinsufficient gene DNA sequence.

In another preferred embodiment the method of the invention comprises the co-transformation of the organism with an independent transgenic construct comprising a modified version of the haploinsufficient gene, which is resistant to the means by which a given underdominant construct specifically degrades or directly inactivates the haploinsufficient gene transcript or expression product, or which specifically disrupts the haploinsufficient gene DNA sequence, and with an underdominant construct comprising a sequence leading to the provision of a means which specifically degrades or directly inactivates the haploinsufficient gene transcript or expression product, or which specifically disrupts the haploinsufficient gene DNA sequence and a haploinsufficient gene that comprises the provision of an at least partial rescue to a means which specifically degrades or directly inactivates the haploinsufficient gene transcript or expression product, or which specifically disrupts the haploinsufficient gene DNA sequence. The method may additionally comprise the steps of obtaining organisms homozygous for said underdominant construct; and removing said independent transgenic construct by chromosomal recombination or segregation.

In yet another preferred embodiment the expression of more than one haploinsufficient gene of the organism may be reduced and rescued in the organism. Said reduction and rescuing of the expression of a haploinsufficient gene may preferably be conveyed by a single transgenic locus in the organism or by multiple transgenic loci in the organism. In a further embodiment, said reduction of the expression of a haploinsufficient gene may be conveyed by multiple transgenic loci and said rescuing of the expression of a haploinsufficient gene may be conveyed by a single transgenic locus.

In a further preferred embodiment said reduction and rescuing of the expression of two or more haploinsufficient genes may be conveyed by functionally cross-linked transgenic loci. Preferably, said functionally linked locus comprises a means for reducing the expression of a haploinsufficient gene of a first haploinsufficient gene, and a rescuing agent able to increase the reduced expression of a second haploinsufficient gene at a first transgenic locus; and a means for reducing the expression of a haploinsufficient gene of a second haploinsufficient gene, and a rescuing agent able to increase the reduced expression of a first haploinsufficient gene at a second transgenic locus.

In yet another preferred embodiment, said reduction of the expression of two or more haploinsufficient genes is conveyed by one transgenic locus and wherein said rescuing of the expression of two or more haploinsufficient genes is conveyed by two or more transgenic loci, wherein said transgenic loci are functionally linked.

In another specific embodiment of the present invention, the method comprises the step of additionally introducing into the organism a mechanistically distinct population transformation construct.

It is preferred that an underdominant construct as mentioned herein above additionally comprises an effector gene. Said effector gene may preferably be selected from the group comprising a dengue fever virus refractory gene, a human malaria refractory gene, an avian malaria refractory gene, a tomato spotted wilt virus refractory gene, a herbicide resistance gene, an insecticidal gene, a drought resistance gene, a parasitic nematode resistance gene and a gene yielding improved plant yield.

In a further aspect the present invention relates to a genetic system comprising the following components: (a) a means for specifically reducing the expression of a haploinsufficient gene; and (b) a rescuing agent able to increase the reduced expression of said haploinsufficient gene.

In a preferred embodiment said means for specifically reducing the expression of said haploinsufficient gene specifically degrades or directly inactivates the haploinsufficient gene transcript or expression product, or specifically disrupts the haploinsufficient gene DNA sequence.

In another preferred embodiment of the present invention said specifically degrading or inactivating means comprises a siRNA, miRNA, an antisense RNA molecule, an antisense DNA molecule, or an agent conveying RNA-directed DNA methylation.

In another preferred embodiment of the genetic system said means, which specifically disrupts said haploinsufficient gene DNA sequence is a zinc finger nucleases, a Transcription Activator-Like Effector Nuclease (TALEN), CRISPR or a meganuclease.

In a further preferred embodiment of the genetic system said rescuing agent is a modified version of said haploinsufficient gene sequence. Preferably, said modified version of said haploinsufficient gene sequence is resistant to a means which specifically degrades or directly inactivates the haploinsufficient gene transcript or expression product, or which specifically disrupts the haploinsufficient gene DNA sequence. It is further preferred that said rescuing agent additionally comprises an effector gene. In another preferred embodiment of the genetic system according to the present invention said effector gene is selected from the group of a dengue fever virus refractory gene, a human malaria refractory gene, an avian malaria refractory gene, a tomato spotted wilt virus refractory gene, a herbicide resistance gene, an insecticidal gene, a drought resistance gene, a parasitic nematode resistance gene and a gene yielding improved plant yield.

In another particularly preferred embodiment of the present invention said genetic system is comprised on or provided in the form of a mobile genetic element, plasmid or exogenous DNA capable of genomic integration.

In another aspect that present invention relates to a use of a genetic system as defined herein above for the transformation of an organism. Said organism is preferably a multitude or population of organisms of the same species.

In yet another aspect the present invention relates to a use of a genetic system as defined herein above for establishing said means for reducing the expression of a haploinsufficient gene; and said rescuing agent able to increase the reduced expression of said haploinsufficient gene in homozygous form at a high frequency in a population of an organism.

In yet another preferred embodiment, the present invention relates to a use of a genetic system as defined herein above for decreasing its introgression into a population of otherwise interfertile sexually reproducing organisms, with the proviso that said organism is not a human being.

In a preferred embodiment, said decrease in the introgression is a prevention of introgression resulting in the elimination or limitation of the sexual reproduction of hemizygous progeny.

In another aspect the present invention relates to a genetically modified organism, with the proviso that said organism is not a human being, comprising (a) a means for specifically reducing the expression of a haploinsufficient gene; and (b) a rescuing agent able to increase the reduced expression said haploinsufficient gene. Preferably, said means for specifically reducing the expression of said haploinsufficient gene specifically degrades or directly inactivates the haploinsufficient gene transcript or expression product, or specifically disrupts the haploinsufficient gene DNA sequence. In a preferred embodiment, said specifically degrading or inactivating means comprises a siRNA, miRNA, an antisense RNA molecule, an antisense DNA molecule, or an agent conveying RNA-directed DNA methylation. In yet another preferred embodiment, said means, which specifically disrupts said haploinsufficient gene DNA sequence is a zinc finger nucleases, a Transcription Activator-Like Effector Nuclease (TALEN), a CRISPR or a meganuclease. It is further preferred that said rescuing agent is a modified version of said haploinsufficient gene sequence. In a further preferred embodiment of the present invention the modified version of said haploinsufficient gene sequence is resistant to a means which specifically degrades or directly inactivates the haploinsufficient gene transcript or expression product, or which specifically disrupts the haploinsufficient gene DNA sequence. The rescuing agent may, in a preferred embodiment, additionally comprise an effector gene. The effector gene may preferably be selected from the group of a dengue fever virus refractory gene, a human malaria refractory gene, an avian malaria refractory gene, a tomato spotted wilt virus refractory gene, a herbicide resistance gene, an insecticidal gene, a drought resistance gene, a parasitic nematode resistance gene and a gene yielding improved plant yield.

In a further preferred embodiment relating to the genetically modified organism as defined herein above, a sequence leading to the provision of a means which specifically degrades or directly inactivates the haploinsufficient gene transcript or expression product, or which specifically disrupts the haploinsufficient gene DNA sequence, comprises disruptive sequences flanked by site specific recognition sites for a recombinase, preferably Cre or FLP, allowing to render said sequence leading to the provision of a means which specifically degrades or directly inactivates the haploinsufficient gene transcript or expression product. It is preferred that said means for reducing the expression of a haploinsufficient gene; and said rescuing agent able to increase the reduced expression of said haploinsufficient gene are comprised in an underdominant construct.

In a further embodiment, the genetically modified organism is homozygous for the underdominant construct. In an alternative embodiment, the genetically modified organism is hemizygous for the underdominant construct.

In yet another preferred embodiment of the present invention the genetically modified organism has a reduced competitive fitness compared to the organism homozygous for said underdominant construct.

In a further preferred embodiment the haploinsufficient gene as mentioned herein above is an endogenous cytoplasmic ribosomal protein (CRP), a transcription factor, a tumor suppressor gene, a gene related to muscle function, a homeodomain protein coding gene, or another gene with evidence indicating that it is potentially haploinsufficient in a specific organism. It is particularly preferred that said haploinsufficient gene is Rpl14 or Rpl 23aA.

In yet another preferred embodiment of the present invention said organism as mentioned herein above is a disease vectoring animal, disease causing animal, or a livestock animal, or a plant, or a fungus, or a protist.

Said disease vectoring animal is preferably an insect, an arachnid. Said insect is preferably a mosquito or a fly. Said arachnid is, in a preferred embodiment, a tick. Said rodent is, in a preferred embodiment, a rat or mouse.

Said disease causing animal is, in a preferred embodiment, a human disease causing nematode, an animal disease causing nematode or a plant disease causing nematode.

Said plant is, in a further preferred embodiment, an agricultural plant or a pest plant. A preferred agricultural plant is a staple crop, more preferably a grain crop, root crops, tubers, pulses, sorghum, or legumes; or a sugar producing crop, preferably sugar cane or sugar beet; or an oil producing plant, more preferably rapeseed, soybean, oil palm, safflower, or sunflower.

In a further embodiment said pest plant is an invasive plant, a poison plant or a plant causing allergic reactions in animals, preferably in human beings.

In yet another embodiment, said plant is an algae, preferably an algae used in biofuel production.

It is further preferred that the fungus as mentioned above is a toxic fungus or a fungus used in bioreactor production. The fungus may, in a specific embodiment, be derived from the genus *Saccharomyces* or *Aspergillus*.

DESCRIPTION OF THE FIGURES

FIG. 2 (A) depicts "wildtype" (GFP) homozygous flies that have two copies of the endogenous RpL14 gene with normal levels of expression. FIG. 2 (B) depicts (RFP/GFP) {Ud}86 heterozygotes, dsRNAi, activated by the GAL4-UAS binary system, targeting the endogenous RpL14 knocks-down RpL14 expression. This RpL14 knockdown is partially rescued by the rescue copy, RpL14$^r$, which is designed to be resistant to the dsRNAi. FIG. 2 (C) shows (RFP) {Ud}86 homozygotes, where two RpL14$^r$ rescue copies are present, to overcome the haploinsufficiency effects of having functionally less than two copies of RpL14 expression.

FIG. 3 shows the sequence of RpL14.dsRNA, its RpL14$^+$ target and the insensitive RpL14$^r$ gene. Further depicted is the entire exon 2 of RpL14. The three segments run continuously from 5' to 3' left to right from the Block A to Linker to Block B segments and are only broken up and interleaved here to aid illustration. The first line of sequence (SEQ ID NO: 15) shows the RNAi targeting RpL14.dsRNA (the sequence of the inverted repeat is not shown). Two non-contiguous blocks of sequences are targeted by RpL14.dsRNA. The linker between block A and B is positioned arbitrarily and has no similarity with any other sequence. Vertical lines shown identity between the dsRNA and the RpL14 (SEQ ID NO: 16) and RpL14$^r$ (SEQ ID NO: 17) genes. While RpL14 is efficiently targeted for RNAi, the number and distribution of the 14 synonymous mutations in RpL14$^r$ prevents the same degree of knockdown by RNAi and rescues RpL14 expression.

FIG. 7 (A) shows the cumulative fraction of adults eclosing each day of development. Females are indicated with solid lines and males with dashed lines. The numbers in the legend give the average time to eclosion for each genotype in days. The difference between homozygotes in development time is not significant (males Kolmogorov-Smirnov test D=0.0749, n1=674, n2=566, P=0.0634; females K-S test D=0.0445, n1=778, n2=715, P=0.452). The difference between pooled homozygotes and heterozygotes in development time is highly significant (males K-S test D=0.272, n1=1240, n2=966, P=2.56×10$^{35}$; females K-S test D=0.292, n1=1493, n2=1149, P=1.64×10$^{-48}$). FIG. 7 (B) shows the relative abundance of offspring from various crosses. The columns correspond to the proportion of offspring genotypes from each type of cross. The labels along the bottom indicate parental genotypes. The average proportion of homozygotes was set to 1. In all cases there is a deficiency of heterozygotes surviving to eclosion relative to homozygotes. The horizontal bar indicates the expected relative proportion of heterozygotes. In all cases the heterozygous deficiency is significant (from left to right, d.f.=2, $\chi2$=24.37, P=5×10-6; d.f.=1, $\chi2$=8.33, P=0.0039; d.f.=1, $\chi2$=11.34, P=0.000759; d.f.=1, $\chi2$=4.40, P=0.0359; d.f.=1, $\chi2$=370.68, P<10-6).

FIG. 8 (A) shows results of multigenerational population experiments providing frequency change of transgenic individuals (+/{Ud}86 and {Ud}86/{Ud}86) from various starting frequencies (gray lines). Populations with starting values higher than the estimated threshold of 0.61 (straight bold dashed line) proceed to fixation while those below result in loss of {Ud}86 (verified by crosses and PCR in all 12 populations). Dashed lines indicate predicted trajectories in the absence of genetic drift and sampling error, under the maximum likelihood estimate (MLE) of fitness parameters shown in parts B and C (12). FIG. 8 (B) shows likelihood surface of relative fitness estimates. Fitness is inferred from the change in allele frequencies in A; {Ud}86/{Ud}86=0.71 (0.62-0.81 95% C.I.) and +/{Ud}86=0.22 (0.16-0.28, 95% C.I.) FIG. 8 (C) shows MLE fitness estimates of the transgenic genotypes. Error bars indicate the confidence intervals estimated in part B.

FIG. 12 depicts the complement of targeting miRNA sequences expressed in the miRNA genes miRNA1 and miRNA2 shown in FIG. 11. The miRNA targeting sequences are similar but not identical to the sequences targeted in RpL23aA, as described in the method of Schwab et al The Plant Cell, Vol. 18, 1121-1133. The sequence of the rescue gene where synonymous mutations have been introduced to a copy of the RpL23aA are also shown (rescue). The frequency and position of the synonymous mutations are intended to render this gene insensitive (or substantially so) to reduction by the targeted miRNA. The corresponding sequence of the RpL23aB is also shown, which exhibits a high degree of sequence similarity to RpL23aA. The location and dissimilarities in the RpL23aB sequence should result limited sensitivity to the miRNA targeting relative to RpL23aA.

DETAILED DESCRIPTION OF THE INVENTION

Figure 1:
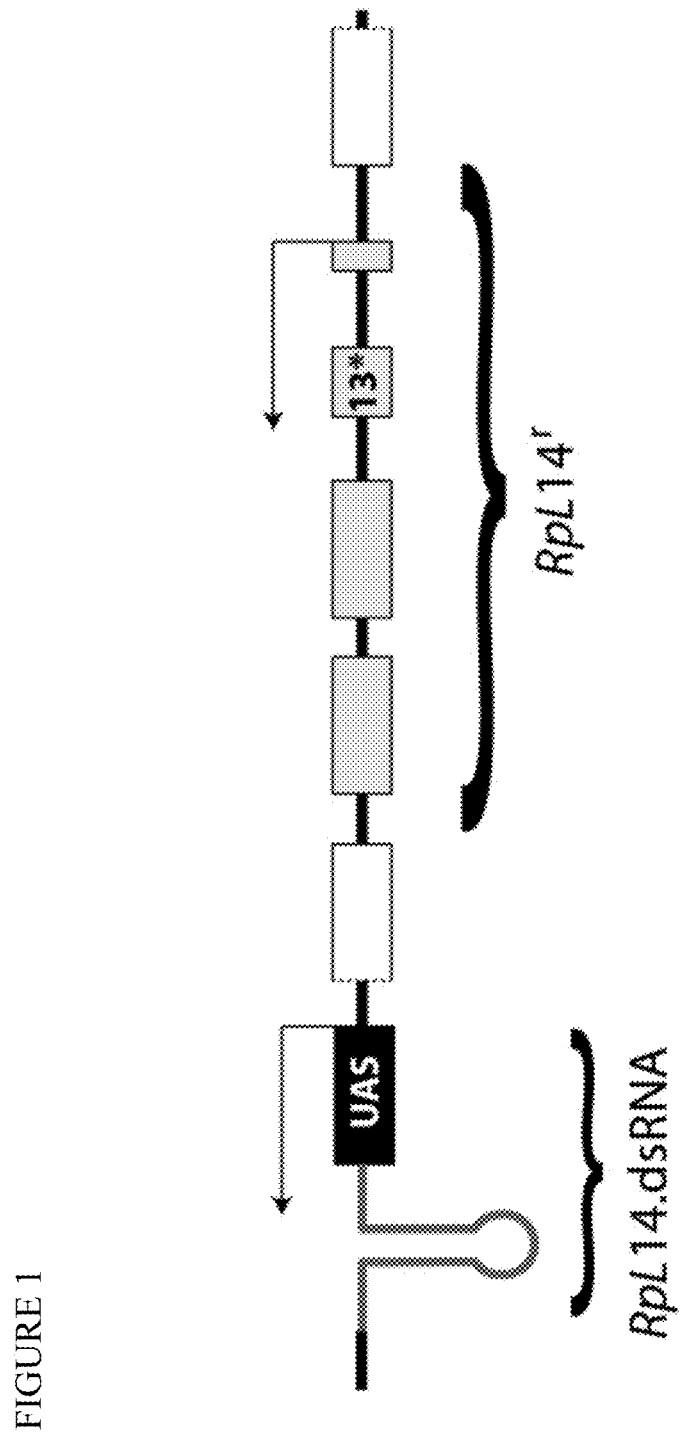
FIG. 1 depicts an underdominance contruct. The first gene of the construct is a dsRNA RNAi knock-down (medium gray) under the control of a UAS promoter (black). This targets 72 bp of exon 2 of the endogenous wildtype gene RpL14$^+$ (cytogenetic position 66D8). The second gene (light gray) of the construct is a rescue gene RpL14$^r$ that is insensitive to the RNAi knock-down. RpL14$^r$ is a complete RpL14 gene, including all its genomic flanking regions and portions of the flanking genes (white), into which 14 synonymous substitutions (14*) have been strategically made in exon 2.

The present invention relates to a method for reducing the competitive fitness of an organism hemizygous for a transgenic locus compared to the organism homozygous for the transgenic locus.

Although the present invention will be described with respect to particular embodiments, this description is not to be construed in a limiting sense.

Before describing in detail exemplary embodiments of the present invention, definitions important for understanding the present invention are given.

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of +20%, preferably +15%, more preferably +10%, and even more preferably +5%. In certain aspects the term "about"

may also refer to a value, which is larger or smaller by several integers, preferably by 5, 4, 3, 2, or 1 in comparison to the starting value.

It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group, which preferably consists of these embodiments only.

If the term "comprising" is used in the context of sequences, in particular nucleotide sequences, the term may not only refer to the sequence mentioned in the sequence listing, but also to the complementary sequence thereof, unless the context states otherwise.

Furthermore, the terms "first", "second", "third" or "(a)", "(b)", "(c)", "(d)" or "(i)", "(ii)", "(iii)", "(iv)", "(v)", "(vi)", "(vii)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)" or "(i)", "(ii)", "(iii)", "(iv)", "(v)", "(vi)", "(vii)" etc. relate to steps of a method or use there is no time or time interval coherence between the steps, i.e. the steps may be carried out simultaneously or there may be time intervals of seconds, minutes, hours, days, weeks, months or even years between such steps, unless otherwise indicated in the application or claims as set forth herein above or below.

It is to be understood that this invention is not limited to the particular methodology, protocols, proteins, bacteria, vectors, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

If not otherwise defined the terms used herein may be derived from "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland. If not otherwise defined the terms used in the context of evolution or inheritance may be derived from Hartl, D. L. & Clark, A. G. *Principles of Population Genetics*, Sinauer Associates: 1997.

Although several documents are cited throughout the text of this specification, which are incorporated by reference in their entirety, nothing herein is to be construed as an admission that the invention is not entitled to antedate such disclosure by virtue of prior invention.

As has been set out above, the present invention concerns in one aspect a method for reducing the competitive fitness of an organism hemizygous for a transgenic locus compared to the organism homozygous for the transgenic locus, with the proviso that the organism is not a human being, comprising the steps of: (a) reducing the expression of a haploinsufficient gene in the organism, wherein said reduction is conveyed by a transgenic locus in the organism; and (b) rescuing the reduced expression in the organism, wherein said rescue is conveyed by the same transgenic locus in the organism, yielding an organism which is less competitively fit if hemizygous for the transgenic locus than if homozygous for the transgenic locus.

The term "competitive fitness" as used herein refers to the average ability of organisms with a certain genotype to survive and reproduce in the natural environment. A complete loss of competitive fitness may lead to inviability and/or infertility of an organism. A "normal competitive fitness" as used herein refers to the average capacity to survive and/or reproduce exhibited in individuals or organisms which do not comprise an underdominant construct according to the present invention. A "reduced competitive fitness" or a "less competitively fit" state of an organism refers to a reduction of an organism's viability and/or fertility and/or its ability to attract mates and/or its fecundity. Such a reduction may not be lethal to an organism, however diminish its capacity to survive and/or reproduce. Such a reduction may include a decrease of fitness of an organism of about 5%, 10%, 15%, 20%, 25%, 30%, 35%, 40%, 45%, 50%, 60%, 70%, 80% or 90% or any value in between these value in comparison to an organism with normal competitive fitness as defined herein above. The reduction may be measured or determined or inferred according to any suitable procedure. For example, the survival of an organism in an environment may be determined after a specific time frame, e.g. within 10%, 15%, 20%, 25%, 30%, 35%, 40%, 45% 50%, 60%, 70%, 80% or 90% of a typical generation period. The fertility may be determined according to the number of progeny in comparison to an average value within a species or group of individuals of the species. The relative competitive fitness of genotypes can be inferred from allele frequency changes between generations, e.g. according to Catteruccia et al., Science 299, 2001-2003 (2003), using an appropriate statistical framework (e.g. based on Clark et al., Heredity 46, 321-46 (1981)). Further details may be derived from FIG. 8 of the present application. Alternatively, the relative competitive fitness of genotypes may be estimated by measuring life-history traits in a single generation that are likely to contribute to competitive fitness. Such traits may include or be selected from fecundity, variability, weight of individuals, sexual attractiveness, number of gametes generated, growth rate(s), and/or mobility in a single generation. Further details may be derived from Irvin et al., PNAS, 101, 891-6 (2004), or Amenya et al., Insect Molecular Biology 19, 263-269 (2010).

In further specific embodiments, the reduction of competitive fitness may also be reflected by the yield, output or production of compounds or material. For example, a plant, in particular of a plant cultivar, may be considered as having a reduced competitive fitness if the yield or production gain is reduced. In the context of animals the phenotype causing competitive fitness reduction maybe due to reduction in expression prior to and after embryonic gastrulation In such a scenario, the phenotype may be displayed during later stages. In very specific embodiments, methods and embodiments as described herein exclude methods which are solely dependent on means to reduce the expression of genes in the organism, wherein said reduction is conveyed by maternal deposition of RNA or proteins or a DNA modification which result in an embryonic lethal phenotype and where zygotic expression prior to embryonic gastrulation of transgenic genes provides a rescue from said lethal phenotype. In particular, methods and embodiments as described herein specifically exclude methods or approaches as described in Chen et al. Science 316, 597 (2007) or Marshall et al., The Journal of heredity 102, 336-41 (2011).

Figure 4:
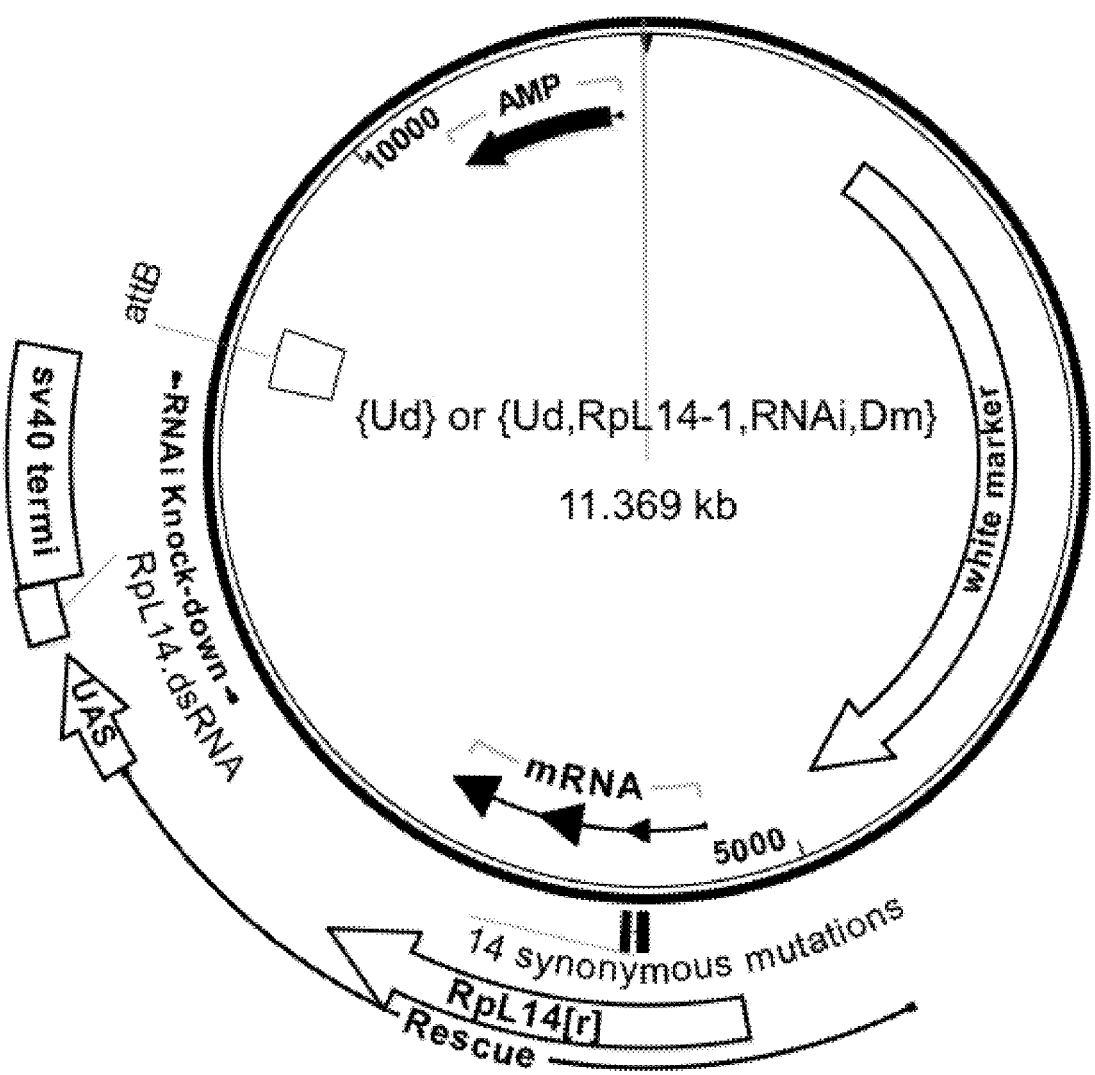
FIG. 4 represents a to-scale schematic of the pUASattB {Ud} containing plasmid that was injected into fly embryos to place the construct at an RFP marked landing site using the phiC31-based integration system. The DNA sequence is given in the accompanying genbank format file.

In further, very specific embodiments, methods or embodiments as described herein exclude methods or approaches where more than two mechanistically distinct transgenic constructs are present at a single locus, representing distinct alleles of the same transgenic locus, and where more than one allele is intended to persist at intermediate frequency at a stable equilibrium in population transformation applications. In particular, methods and embodiments as described herein specifically exclude methods or approaches as described in Davis et al., Journal of theoretical biology, 212, 83-98 (2001). More particular, methods and embodiments as described herein specifically exclude methods or approaches as described in the upper right of FIG. 4 of Davis et al., Journal of theoretical biology, 212, 83-98 (2001).

The term "hemizygous for a transgenic locus" as used herein means that in a diploid or polyploid organism a transgenic locus is present with only one transgenic allele per locus per genome per homologous pair or group of chromosomes. In polyploid organisms more than one pair of homologous chromosomes may be present. Within this group of chromosomes the transgenic locus may be present with one transgenic allele only. In case functionally equivalent but non-homologous pairs of chromosomes are present in a polyploid organism, the transgenic locus may be present with one transgenic allele only within this group of chromosomes. In the case of a diploid organism hemizygosity for a transgenic locus essentially equals heterozygosity for said transgenic locus. The term "heterozygous for a transgenic locus" as used herein means that in a diploid organism a transgenic locus is present with one transgenic allele only. The term "homozygous for a transgenic locus" as used herein means that in a diploid or polyploid organism a transgenic allele is present at a specific locus on both or all copies of a specific chromosome. In polyploid organisms in which more than one pair of homologous chromosomes may be present the term homozygous may include situations where more than one transgenic allele is present at the transgenic locus. Such an allele may accordingly be present with as many copies as chromosomes are present in this group.

In case functionally equivalent but non-homologous pairs of chromosomes are present in a polyploid organism, the term homozygous includes situations where there is more than one transgenic allele present at the transgenic locus. Such an allele may accordingly present with as many copies as chromosomes are present in this group.

The term "homologous chromosomes" as used herein refers to chromosome pairs of approximately the same length, centromere position, and staining pattern, comprising genes for the same characteristics at corresponding loci. Typically one homologous chromosome is inherited from the organism's female parent; the other from the organism's male parent. Homologous chromosomes are typically not entirely identical, but may carry the same type of information. A "functionally equivalent but non-homologous chromosome" as used herein may carry a similar type of information as homologous chromosome, but may show differences in length, centromere position, staining pattern, and/or the presence of genes at corresponding loci. Such chromosomes are typically also designated as homologous chromosomes. Such chromosomes which may be derived from parental sub-genomes may typically pair faithfully during meiosis, which leads to disomic inheritance. In specific embodiments, a 4-fold pairing may take place leading to a tetrasomic inheritance or higher order equivalents.

The term "transgenic locus" as used herein refers to the genomic site of a stable integration of an underdominant construct into a chromosome of a pair of homologous or a group of homologous chromosomes. The transgenic locus may accordingly comprise all elements or sequences provided in an underdominant construct as defined herein. Alleles at this transgenic locus can be homozygous, hemizygous/heterozygous or wildtype. In case of a wildtype genotype no transgenic insertion has taken place. The locus comprising the underdominant construct may, in certain embodiments, also be cisgenic. The term "cisgenic" as used herein means that the locus may comprise only genes or genetic elements derived from closely related organisms, or from organisms which could otherwise be conventionally bred. In further embodiments, the locus comprising the underdominant construct may also be intragenic, i.e. being derived from the same genome, famigenic, i.e. being derived from a species within the same family, or linegenic, i.e. being derived from a species within the same lineage. In specific embodiments of the invention the genomic site of a stable integration of an underdominant construct into a chromosome of a pair of homologous or a group of homologous chromosomes may take place at a single locus, thus providing a single transgenic locus in the organism, or at multiple loci, thus providing multiple transgenic loci in the organism. The multiple loci may differ in terms of chromosomes on which they are located, e.g. one locus on chromosome 1, a further on chromosome 2 etc, and/or in terms of positions within a chromosome, e.g. one locus at the p arm, another locus at the q arm etc. Further variations and all suitable localization positions within the genome of an organism are also envisaged by the present invention.

The term "allele at transgenic locus" as used herein refers to the sequence variants at a transgenic locus. Alleles at this transgenic locus can be homozygous, hemizygous/heterozygous or wildtype. A wildtype allele denotes that there is no transgenic insert at the transgenic locus insertion site which is present in homozygotes and hemizygotes. In case of a diploid wildtype genotype both wildtype alleles have no transgenic insertion at the transgenic locus insertion site.

An "underdominant construct" as used herein means a construct which causes underdominance according to the method of the invention. It may provide a functionality or means which allows to reduce the expression of a haploinsufficient gene and/or which provides a functionality or means which allows to rescue the reduced expression of a haploinsufficient gene. The underdominant construct may be integrated into the genome of an organism, e.g. from a plasmid or any other transferable genetic element, in order to transform an organism. The integration may take place at one specific position or at more than one position resulting in multiple copies per locus. The number of integrated underdominant constructs may vary. For example 1, 2, 3, 4, 5, 6, 7, 8, 9, 10 or more underdominant constructs may be transformed and/or be present in a genome of an organism, e.g. at a corresponding number of transgenic loci as defined above, or at a different number of transgenic loci. The constructs may, for instance, be present at one transgenic locus, e.g. as tandem repeats or any other repeated form, or they may be present at 2, 3 or more loci within the genome, e.g. on 2 or more different chromosomes.

The underdominant construct may comprise flanking regions at the 5' and/or 3' end, preferably at both ends, which are homologous to genomic regions of an organism to be transformed. The flanking regions may have any suitable length, e.g. a length of about 10, 20, 30, 40, 50, 60, 70, 80, 90, 100, 120, 130, 150, 170, 200, 250, 300, 350, 400, 500, 600, 700, 800, 900, 1000 nucleotides or more or any value in between these values. The flanking regions may be chosen such that integration of genetic modifications may be carried out in a site specific manner, e.g. the deletion of a gene or genetic element, the modification of a genomic sequence, a chromosomal rearrangement etc. The homologous flanking regions may have a complementarity of about 100%, or at least 99%, 98%, 97%, 96%, 95%, 85%, 80%, or 75% or any value in between these values with a sequence in the genome of an organism to be transformed. In case of location on different chromosomes, the underdominant construct may be provided with different flanking regions, e.g. the flanking region of chromosome A for construct 1, and the flanking regions of chromosome B for construct 2, wherein construct 1 and 2 essentially only differ by the different flanking regions. The efficiency of these site specific integration approaches may be enhanced through the transient induction of chromosomal double strand breaks, e.g. through the expression of TALENs or ZFNs targeting the intended integration site.

The underdominant construct may in specific embodiments comprise only a functionality or means which allows to reduce the expression of a haploinsufficient gene. The underdominant construct may accordingly comprise a sequence leading to the provision of a means which specifically degrades or inactivates the haploinsufficient gene transcript or expression product as defined herein, or which specifically disrupts the haploinsufficient gene DNA sequence. The underdominant construct may, for example, comprise a sequence leading to the provision of siRNA, miRNA, an antisense DNA or antisense RNA molecule, or which allows for the expression of a sequence specific nuclease such as a zinc finger nuclease, CRISPR, meganuclease activity or TALEN.

The underdominant construct may in alternative embodiments comprise only a functionality or means which allows to rescue the reduced expression of a haploinsufficient gene.

In further preferred embodiments, the underdominant construct may comprise both functionalities, i.e. a functionality which allows to reduce the expression of a haploinsufficient gene and a functionality which allows to rescue the reduced expression of a haploinsufficient gene. The underdominant construct may further comprise further suitable elements. For example, optical or visual marker genes or elements, antibiotics resistance genes, herbicide resistance genes, promoter elements, enhancer elements, terminator elements etc. may be present.

It is particularly preferred that the underdominant construct comprises, in addition to the reducing and/or rescuing activity as defined herein above an effector gene. The effector gene may be provided in a form allowing its expression and/or provision of the expressed protein product. Therefore suitable accessory elements may be provide, e.g. a promoter element, terminator elements, enhancer element etc. In certain embodiments, the absence of an effector gene from the underdominant construct is envisaged.

In a very specific embodiment, the underdominant construct may comprise disruptive sequences, which allows to render any sequence of the underdominant construct provided within or between the disruptive sequences inactive. Envisaged examples of such disruptive sequences are site specific recognition sites for a recombinase. Site specific recognition sites for a recombinase may, for example, be provided at or close to the 5' and 3' terminus of a sequence leading to the provision of a means which specifically degrades or inactivates the haploinsufficient gene transcript or expression product as defined herein, or which specifically disrupts the haploinsufficient gene DNA sequence.

Site specific recognition sites for a recombinase may, in alternative embodiments, be provided at or close to the 5' and 3' terminus of a sequence leading to the provision of a means which allows the activation of the means to the reduced expression of a haploinsufficient gene. It is further envisaged that site specific recognition sites for a recombinase may be provided at or close to the 5' and 3' terminus of a sequence comprising a sequence leading to the provision of a means which specifically degrades or inactivates the haploinsufficient gene transcript or expression product as defined herein, or which specifically disrupts the haploinsufficient gene DNA sequence and a sequence leading to the provision of a means which allows to rescue the reduced expression of a haploinsufficient gene.

Recombinases which can be used for gene activation or inactivation comprises sequences between site specific recognition sites would be known to the skilled person. The use of any suitable recombinase and its cognate recognition sites is envisaged herein. Preferred is the employment of Cre recombinase or FLP recombinase and their respective recognition sites. It is particularly preferred to use Cre-Lox systems or derivatives thereof, or FLP-FRT systems or derivatives thereof. By providing the recognition sites in a direct repeated manner a deletion of sequence between the repeats can be achieved. Similarly, by providing other orientations or more than two recognition sites further rearrangement pattern may become possible, e.g. an inversion of the sequences. Further details may be derived from Ryder et al. Genetics 167, 797-813 (2004); Golic & Golic Genetics 144, 1693-711 (1996); Ito et al., Development, 771, 761-771 (1997)).

In specific embodiments, the recombinase gene may constitute an activation-gene according to the present invention, i.e. the recombinase may lead to activation of the sequence which specifically degrades or inactivates the haploinsufficient gene transcript or expression product as defined herein, or which specifically disrupts the haploinsufficient gene DNA sequence. In further specific embodiments, a recombinase may also be used for inactivation purposes of one or more parts of the underdominace genetic systems as described herein.

The activation or inactivation of the sequence, which specifically degrades or inactivates the haploinsufficient gene transcript or expression product as defined herein, or which specifically disrupts the haploinsufficient gene DNA sequence may preferably be achieved via an in vivo exposure of the cell by said recombinase, e.g. Cre recombinase or FLP recombinase. The in vivo exposure may be implemented according to any suitable means. Recombinases to be used for such an approach, i.e. in vivo exposure, may be provided, for example, externally, e.g. proteins may be administered to the organism or cell, or they may be provided by internal expression, e.g. on an expression system on a plasmid or an expression system encoded genomically. In further embodiments, the recombinase activity may be provided with the boundaries of the underdominant construct itself, e.g. within disruptive sequences or specific recombinase recognition sites on said underdominant construct. The expression of the recombinase may accordingly lead to a deletion of the encompassed sequences including its own sequence. The in vivo exposure may be controlled by any suitable control mechanism, e.g. via a inducible promoter like a heat-shock promoter or a promoter induced by a dietary compound.

The term "wildtype" as used herein refers to the expected levels of expression or competitive fitness likely to be commonly encountered in individuals of a species, which do not have a genomic integration of an underdominant construct according to the present invention. In the case of plant varieties the term may specifically relate to the expected levels of expression or competitive fitness that is likely to be commonly encountered in individuals of the same variety without an underdominant construct according to the present invention.

The transgenic locus or derivatives of the locus as mentioned above may include or be associated with one or more effector genes, or may not include or be associated with an effector gene. The absence of an effector gene may be envisaged in cases in which the transgenic locus per se conveys a molecular effect, e.g. a disease resistance to viral disease. It is understood that the capacity of some viruses to replicate in cells may be highly sensitive to cytoplasmic ribosome protein expression (see, e.g., Cherry et al., Genes & development, 19, 445-52 (2005)). Where a targeted haploinsufficient gene has a role in reducing disease transmission it is conceivable that disease refractoriness may be wholly or partially conferred by the underdominant construct in the absence of any additional effector genes. Effector genes may also be absent from a transgenic construct if an effector gene is present at another transgenic locus. Effector genes may further be absent from a transgenic construct when used for purposes of biocontainment in a cultivar stock where the agronomic traits are, for example, distributed at other locations unlinked or weakly linked to the transgenic locus. In a specific embodiment, this may be implemented when attempting to use an underdominant construct to ensure true breeding of a conventional elite cultivar where the agronomic traits where distributed throughout the genome often at unidentified loci. In a further example, an implementation may be the biocontainment of a cultivar which had previously be genetically modified, e.g. by the genomic integration of a transgenic construct which conferred an agronomic trait but which was not itself underdominant.

Examples of transgenes, which may be integrated into genomes without using underdominant constructs, or as effector genes in the context of underdominant constructs as described herein, may be identified on the basis of any suitable database. Preferred is the gene registry maintained at the biological clearing house (BCH) as part of the Cartagena Biological Protocol on Biodiversity. The database may, for example, be accessed via bch.cbd.int/database/gene-registry/.

Examples of transgenes or effector genes, which may be integrated into genomes without using underdominant constructs, or which may be used as effector genes in the context of underdominant constructs as described herein include (with BCH identification/accession number in brackets): 7Crp peptide (BCH ID #:46121), 9-cis-epoxycarotenoid dioxygenase (NCED) (BCH ID #:45879), Triple gene block (BCH ID #:45834), Bromoxynil-specific nitrilase (BCH ID #:14976), CP Peptide (BCH ID #:104319), Acetyl-CoA carboxylase large subunit (BCH ID #:102613), Acetolactate synthase (ALS) (BCH ID #:15177), Chimeric Acetolactate Synthase (ALS) (BCH ID #:15164), Filamin A (FLNA) (BCH ID #:45847), Acyl-acyl carrier protein thioesterase ClFatB4 (BCH ID #:101362), E3 protein (BCH ID #:45813), Adiponectin (BCH ID #:46072), ADP-dependent glucokinase (ADP-GK) (BCH ID #:45854), Acetohydroxy acid synthase (BCH ID #:48073), Cholera toxin (BCH ID #:102896), Anthocyanin 5-acyltransferase (BCH ID #:43794), Apyrase (BCH ID #:48365), UDP-glucose:sinapate glucosyltransferase (BCH ID #:101523), Barnase ribonuclease inhibitor (BCH ID #:14973), beta-lactamase (BCH ID #:14975), Phytoene Desaturase (BCH ID #:103621), Fatty Acid Desaturase 2 (BCH ID #:104323), Catechol dioxygenase (BCH ID #:45877), Caffeoyl coenzymeA O-methyl transferase (BCH ID #:102123), Chaperonin containing t-complex polypeptide 1 (BCH ID #:45914), CDC25 (BCH ID #: 102013), glycoprotein (GP) (BCH ID #:45851), Chloramphenicol acetyltransferase (BCH ID #:100382), Cinnamoyl coenzymeA reductase (BCH ID #:102122), Major histocompatibility complex class III (BCH ID #:45905), Major histocompatibility complex class III (BCH ID #:45906), Major histocompatibility complex class III (BCH ID #:45907), Odontoglossum ringspot virus coat protein (BCH ID #:45835), Erythromycin Ribosomal Methylase (BCH ID #:45859), Erythromycin Ribosomal Methylase A (BCH ID #:45860), Cryj peptide (BCH ID #:102150), Cold shock protein B (CSPB) (BCH ID #:103065), Cyanophycin Synthetase (BCH ID #: 103096), Cytochrome b (cyt-b) (BCH ID #:45832), DNA adenine methylase (BCH ID #: 15008), 5'methylthioadenosine nucleosidase (BCH ID #:45819), 5'methylthioadenosine (MTA) nucleosidase (BCH ID #:45820), 5'methylthioadenosine (MTA) nucleosidase (BCH ID #:45821), 5' methylthioadenosine (MTA) nucleosidase (BCH ID #:45827, BCH ID #:45828; BCH ID #:45829; BCH ID #:45830; BCH ID #:45831), Dihydrodipicolinate synthase (BCH ID #:14978), Dicamba Monooxygenase (BCH ID #:100728), Doc1/Apc10 (BCH ID #:45817), nodD FITA (BCH ID #:45912), DsRed2 Fluorescent Protein (BCH ID #: 101476), E1 protein (BCH ID #:45803), E1 proteins (BCH ID #:45811), E4 protein (BCH ID #:45805), E5 protein (BCH ID #:45806), elastin 100×ELP (BCH ID #:103553), E2 protein (BCH ID #:45812), EPEC Secreted Protein A (BCH ID #:45844), Initiation Factor 4A (eIF4AI) (BCH ID #:46098), Initiation Factor 4A (eIF4AIII) (BCH ID #:45798), Initiation Factor 4A (eIF4AII) (BCH ID #:45797), Firefly Luciferase (BCH ID #:104332), Flavonoid-hydroxylase (BCH ID #:43793), Flavonoid 3'; 5' hydroxylase (BCH ID #:15010), Gibberellin (GA) 20-oxidase [gibberellin; 2-oxoglutarate:oxygen oxidoreductase (20-hydroxylating; oxidizing)] (BCH ID #:103517), Gamma-glutamylcysteine synthetase (GSH) (BCH ID #:101271), Serine protease inhibitor (BCH ID #:101929), Low Phytic Acid 1 (BCH ID #:103619), gI Glycoprotein (BCH ID #:103649), Glyceraldehyde-3-phosphate dehydrogenase (GAPDH) (BCH ID #:45837), Double mutant 5-EnolPyruvylShikimate-3-Phosphate Synthase (BCH ID #:46333), Glyphosate-N-Acteyltransferase (GAT4621) (BCH ID #:48363), Heat shock protein 60 (BCH ID #:45842), Tilapia Growth Hormone (BCH ID #:103750), Hexa Histidine Anchor (BCH ID #:103022), Phosphoribosyl-ATP Pyrophosphorylase (PR-ATP synthetase) (BCH ID #:46077), Sinapoylglucose: choline sinapoyltransferase (SCT); sinapine synthase (BCH ID #:101519), Zeaxanthin epoxidase (BCH ID #:100278), E4 protein (BCH ID #:45814), Hemagglutinin (HA) (BCH ID #:45883), protein crystal (BCH ID #:102269), Truncated Cry 1Ac protein (BCH ID #:103215), Cry1Ab/Ac protein (BCH ID #:103109), 5-enolpyruvylshikimate-3-phosphate synthase (BCH ID #:45913), Sucrose:sucrose 1-fructosyl transferase (BCH ID #:46095), nitrate reductases (BCH ID #:46097), GIGANTEA protein (BCH ID #:45816), Killer protein 4 (BCH ID #:47790), L1 protein (BCH ID #:45809), L2 protein (BCH ID #:45810), Lactoferrin (BCH ID #:45794), Luciferase alpha subunit (BCH ID #:100377), Luciferase beta subunit (BCH ID #:100378), Matrix protein (M1) (BCH ID #:45881), Intimin (BCH ID #:45843), Human Metallothionenine 1A (BCH ID #:104312), Major histocompatibility complex class I (BCH ID #:45899), Major histocompatibility complex class II (BCH ID #:45900; BCH ID #:45903; BCH ID #:45904), Major histocompatibility complex class I (BCH ID #:45901; BCH ID #:45902), Myostatin (BCH ID #:45853), Newcastle disease virus fusion (F) protein (BCH ID #:48971), NodZ (BCH ID #:45910), NolL (BCH ID #:45911), Non-structural protein (NS2) (BCH ID #:45898), Nopaline synthase (BCH ID #:15171), Nucleoprotein (NP) (BCH ID #:45880), Galactosidase (BCH ID #:45875), Beta-lactoglobulin (BCH ID #:45848), Orotidine-5'-phosphate decarboxylase (BCH ID #:46076), Orotidine-5'-phosphate decarboxylase (BCH ID #:46080), P2X2 protein (BCH ID #:45878), Polymerase PA subunit (BCH ID #:45895), Polymerase PB1 subunit (BCH ID #:45886), Polymerase PB2 subunit (BCH ID #:45894), Phosphofructokinase (BCH ID #:104350), Phosphomannose Isomerase (PMI) protein (BCH ID #: 15003), Phytoene Synthase 1 (BCH ID #: 103620), Proteinase inhibitor II (BCH ID #: 104338), Galectin-1 (LGALS1) (BCH ID #:45796), Polyhedrin (BCH ID #:46002), PRP8 (BCH ID #:45908), PRP8 (BCH ID #:45909), E7 protein (BCH ID #:45808), Renin-2 (BCH ID #:45815), delta-endotoxin mCry3A (BCH ID #:43634), RNA 1 Polymerase (BCH ID #:101870), Silk Proteinase Inhibitor 2 (BCH ID #:104313), Cry1C protein (BCH ID #:103217), Stilbene Synthase (BCH ID #:101520), Talin Protein (BCH ID #:45799), Tetanus toxoid (BCH ID #:101618), Tetracycline-controlled transactivator (BCH ID #:101475), Cry1Ab delta-endotoxin (BCH ID #:14985), Acetolactate Synthase (synthetically modified) (BCH ID #:100268), 3"(9)-O-aminoglycoside adenylyl transferase (BCH ID #:15033), 1-aminocyclopropane-1-carboxyllic acid synthase (BCH ID #:15014), 1-amino-cyclopropane-1-carboxylic acid synthase (BCH ID #:15012), 1-amino-cyclopropane-1-arboxylic acid deaminase (BCH ID #: 15013), Acetohydroxyacid synthase (AKA Acetolactate synthase; ALS) (BCH ID #:48364), Acetolactate synthase (BCH ID #:15007), Thermostable alpha-amylase (BCH ID #:14966), Mycolyl-Transferase/Antigen 85A (BCH ID #:45818), Aminoglycoside 3 phosphotransferase II (APH-II) (BCH ID #:14967), barstar ribonuclease inhibitor (BCH ID #:14974), Branching Enzyme 1 (BCH ID #:48366), Branching Enzyme 2 (BCH ID #:48453), Beta-galactoside alpha-2;6-sialyltransferase (BCH ID #:45800), Alpha S1 caesin (BCH ID #:45795), PLRV Coat Protein (BCH ID #:103751), CMV viral coat protein (BCH ID #:15027), PEMV viral coat protein (CP) (BCH ID #:101930), PPV viral coat protein (BCH ID #:104309), PRSV viral coat protein (CP) (BCH ID #:15026), Pea Seed-borne Mosaic Virus coat protein (CP) (BCH ID #:101940), PVY viral coat protein (BCH ID #:15020), WMV-2 viral coat protein (BCH ID #:15024), ZYMV viral coat protein (BCH ID #:15025), 5-enolpyruvulshikimate-3-phosphate synthase (BCH ID #:14979), Cry1A.105 protein (BCH ID #:43771), cry1Ac delta-endotoxin (BCH ID #: 14986), cry1F delta-endotoxin (BCH ID #: 14987), Cry2Ab delta-endotoxin (BCH ID #:14988), Crystal Cry2Ae protein (BCH ID #:101895), Cry34Ab1 delta-endotoxin (BCH ID #:14994), Cry35Av1 delta-endotoxin (BCH ID #:14995), cry3A delta-endotoxin (BCH ID #:14989), Cry3Bbl protein (BCH ID #:14993), Cry9c delta-endotoxin (BCH ID #:14996), Acyl-lipid desaturase (BCH ID #:102160), E2 protein (BCH ID #:45804), E6 protein (BCH ID #:45807), endochintinase (BCH ID #:100280), 5-enolpyruvylshikimate-3-phosphate synthase (BCH ID #:15000; BCH ID #:45463; BCH ID #:101942), Feline leukemia virus envelope glycoprotein (BCH ID #:45046), Feline Leukemia Virus gag proteins (BCH ID #:45047), Feline Leukemia Virus Reverse Transcriptase (BCH ID #:45048), Dihydroflavonol-4-reductase (BCH ID #:15009), N-acetylglucosaminidase (BCH ID #:45945), Stomatal density and distribution (BCH ID #:48460), Stomatal density and distribution (BCH ID #:48458), Homologues of *Cladosporium fulvum* Resistance genes of the Vf region (HcrVf) (BCH ID #:103738), Phosphinothricin N-acetyltransferase (PAT) (BCH ID #:14972), delta(12)-fatty acid dehydrogenase (BCH ID #:100267), Glyphosate oxidoreductase (BCH ID #: 14998), Granule-bound starch synthase (BCH ID #:48072), Green Fluorescent Protein (BCH ID #:45846), HSP70 (BCH ID #:101614; BCH ID #:45839; BCH ID #:45916), *Hordeum vulgare* sucrose transporter (BCH ID #:45917), *Hordeum vulgare* sucrose transporter 1 (HvSUT1) (BCH ID #:101594), Hygromycin B phosphotransferase (BCH ID #:100292; BCH ID #:14991), Luciferase alpha and beta subunit fusion Protein (BCH ID #: 103755), LuxA; LuxB; LuxC; LuxD; LuxE (BCH ID #:45874), Matrix protein (M2) (BCH ID #:45882), Major Spidroin I protein (BCH ID #:48455), Major Spidroin II protein (BCH ID #:48456), PK Protein Kinase (BCH ID #: 103650), Cry2Ab2 protein (BCH ID #:43772), Lipoxygenase 3 (BCH ID #:48030), Neuraminidase (NA) (BCH ID #:45885), Non-structural protein (NS1) (BCH ID #:45896), Neomycin Phosphotransferase II (BCH ID #: 15001), Quinolinic Acid Phosphoribosyltransferase (QPT) (BCH ID #:15416), Replicase/RNA-dependent RNA polymerase [Potato leafroll virus] (BCH ID #:15019), Helicase (BCH ID #:15018), Phosphinothricin N-acetyltransferase (PAT) (BCH ID #:15002), myo-inositol-hexakisphosphate-3-phosphohydrolase (3-phytase) (BCH ID #:15378), Polygalacturonase (BCH ID #:15015), Fibrinogen (BCH ID #:45801), Glycoprotein (BCH ID #:100344), Red Fluorescent Protein (BCH ID #:103740), Resistance gene 1 (BCH ID #:41317; BCH ID #:102164; BCH ID #:102155), Resistance gene 2 (BCH ID #:41318), Resistance gene 3 (BCH ID #: 102165)), S-adenosylmethionine hydrolase (BCH ID #:15387), S-adenosylmethionine (SAM) hydrolase (BCH ID #: 15017), scFv BA 1 (BCH ID #: 103024), Synthetic spider silk protein (BCH ID #:48457), Thioesterase (TE) (BCH ID #: 15005), Beta-Glucuronidase (BCH ID #:46004), Amino acid permease 1 (BCH ID #:48368), Vegetative insecticidal protein 3A (BCH ID #: 14990), Capsid protein VP60 (BCH ID #:102024), WRKY45 Transcription Factor (BCH ID #:103726), Alpha-hordothionine (BCH ID #:46091), Chaperonin containing t-complex polypeptide 1 (BCH ID #:45840; BCH ID #:45915), endo-(1;3-1;4)-beta-glucanase (BCH ID #:100274), telAB protein (BCH ID #:103758), kilA protein (BCH ID #:103757), Large subunit of the ribulose-bisphosphate carboxylase (rbcL) ribosomal binding site (BCH ID #:102611), Translocated Intimin Receptor (BCH ID #:45845), insulin (BCH ID #:102337), Vegetative insecticidal protein 3Aa20 (BCH ID #: 100887), and Glyceraldehyde-3-phosphate dehydrogenase (GAPDH) (BCH ID #:45836; BCH ID #:45838).

In certain embodiments the transgenic locus may be physically linked to the effector gene which may be a part or subsection of a nucleic acid molecule to be introduced into an organism, or being inserted in the genome of an organism. In other embodiments, the transgenic locus may not be physically linked or weakly linked to an effector gene or to an agronomic trait of interest. The effector gene may accordingly, for example, be provided on a different chromosome or at a different, unlinked position within the genome, e.g. derived from the list of effector genes provided herein above.

The term “effector gene” as used herein refers to any gene or expressible unit which confers a phenotypically detectable effect in an organism or a group of organisms. Such an effector gene may provide, for example, an effect with regard to biochemical properties of an organism or its cells, e.g. the provision or reduction or abolition of enzymatic activities, the provision of interaction interfaces with regulatory factors, the expression of novel genes, or novel expression patterns of endogenous genes. The effector gene may further provide effects to the organism with regard to the susceptibility to a disease, e.g. a disease resistance or disease refractoriness, or alternatively an increased disease vulnerability. For example, a resistance to viral infections, bacterial infections, protist infections, fungal infections, or nematode infections may be provided as effect.

Further examples of envisaged effects are an agronomic trait, e.g. a trait leading to the increase of yield of a plant, resistance to environmental influences such as temperature, salt stress, water supply, nitrogen supply etc. Preferred effector genes are a dengue fever virus refractory gene, a human malaria refractory gene, an avian malaria refractory gene, a tomato spotted wilt virus refractory gene, a herbicide resistance gene, an insecticidal gene, a drought resistance gene, a parasitic nematode resistance gene and a gene yielding improved plant yield.

Preferred human malaria refractory genes are genes encoding peptides such as TP10 (encoding a peptide with the sequence AGYLLGKINLKALAALAKKIL; SEQ ID NO: 1), AngII (encoding a peptide with the sequence peptide, DRVYIHPF; SEQ ID NO: 2), or genes encoding single chain antibodies such as mIC3 (GenBank accession number HQ315886), m4B7 (GenBank accession number HQ315885), or m2A10 (GenBank accession number HQ315884). A preferred avian malaria refractory gene is a gene encoding a peptide such as AngII (comprising sequence DRVYIHPF (SEQ ID NO: 2) as mentioned above).

For application in plant organisms the present invention preferably envisages the use of one or more of effector genes or transgenes selected from the group comprising: 7Crp peptide (BCH ID #:46121), 9-cis-epoxycarotenoid dioxygenase (NCED) (BCH ID #:45879), Triple gene block (BCH ID #:45834), Bromoxynil-specific nitrilase (BCH ID #:14976), CP Peptide (BCH ID #:104319), Acetyl-CoA carboxylase large subunit (BCH ID #:102613), Acetolactate synthase (ALS) (BCH ID #:15177), Chimeric Acetolactate Synthase (ALS) (BCH ID #:15164), Filamin A (FLNA) (BCH ID #:45847), Acyl-acyl carrier protein thioesterase ClFatB4 (BCH ID #:101362), E3 protein (BCH ID #:45813), Adiponectin (BCH ID #:46072), ADP-dependent glucokinase (ADP-GK) (BCH ID #:45854), Acetohydroxy acid synthase (BCH ID #:48073), Cholera toxin (BCH ID #:102896), Anthocyanin 5-acyltransferase (BCH ID #:43794), Apyrase (BCH ID #:48365), UDP-glucose:sinapate glucosyltransferase (BCH ID #:101523), Barnase ribonuclease inhibitor (BCH ID #:14973), beta-lactamase (BCH ID #:14975), Phytoene Desaturase (BCH ID #:103621), Fatty Acid Desaturase 2 (BCH ID #:104323), Catechol dioxygenase (BCH ID #:45877), Caffeoyl coenzymeA O-methyl transferase (BCH ID #:102123), Chaperonin containing t-complex polypeptide 1 (BCH ID #:45914), CDC25 (BCH ID #:102013), glycoprotein (GP) (BCH ID #:45851), Chloramphenicol acetyltransferase (BCH ID #:100382), Cinnamoyl coenzymeA reductase (BCH ID #:102122), Major histocompatibility complex class III (BCH ID #:45905), Major histocompatibility complex class III (BCH ID #:45906), Major histocompatibility complex class III (BCH ID #:45907), Odontoglossum ringspot virus coat protein (BCH ID #:45835), Erythromycin Ribosomal Methylase (BCH ID #:45859), Erythromycin Ribosomal Methylase A (BCH ID #:45860), Cryj peptide (BCH ID #:102150), Cold shock protein B (CSPB) (BCH ID #:103065), Cyanophycin Synthetase (BCH ID #:103096), Cytochrome b (cyt-b) (BCH ID #:45832), DNA adenine methylase (BCH ID #:15008), 5'methylthioadenosine nucleosidase (BCH ID #:45819), 5'methylthioadenosine (MTA) nucleosidase (BCH ID #:45820), 5'methylthioadenosine (MTA) nucleosidase (BCH ID #:45821), 5' methylthioadenosine (MTA) nucleosidase (BCH ID #:45827, BCH ID #:45828; BCH ID #:45829; BCH ID #:45830; BCH ID #:45831), Dihydrodipicolinate synthase (BCH ID #:14978), Dicamba Monooxygenase (BCH ID #:100728), Doc1/Apc10 (BCH ID #:45817), nodD FITA (BCH ID #:45912), DsRed2 Fluorescent Protein (BCH ID #:101476), E1 protein (BCH ID #:45803), E1 proteins (BCH ID #:45811), E4 protein (BCH ID #:45805), E5 protein (BCH ID #:45806), elastin 100×ELP (BCH ID #:103553), E2 protein (BCH ID #:45812), EPEC Secreted Protein A (BCH ID #:45844), Initiation Factor 4A (eIF4AI) (BCH ID #:46098), Initiation Factor 4A (eIF4AIII) (BCH ID #:45798), Initiation Factor 4A (eIF4AII) (BCH ID #:45797), Firefly Luciferase (BCH ID #:104332), Flavonoid-hydroxylase (BCH ID #:43793), Flavonoid 3'; 5' hydroxylase (BCH ID #:15010), Gibberellin (GA) 20-oxidase [gibberellin; 2-oxoglutarate: oxygen oxidoreductase (20-hydroxylating; oxidizing)] (BCH ID #:103517), Gamma-glutamylcysteine synthetase (GSH) (BCH ID #:101271), Serine protease inhibitor (BCH ID #:101929), Low Phytic Acid 1 (BCH ID #: 103619), gI Glycoprotein (BCH ID #: 103649), Glyceraldehyde-3-phosphate dehydrogenase (GAPDH) (BCH ID #:45837), Double mutant 5-EnolPyruvylShikimate-3-Phosphate Synthase (BCH ID #:46333), Glyphosate-N-Acetyltransferase (GAT4621) (BCH ID #:48363), Heat shock protein 60 (BCH ID #:45842), Tilapia Growth Hormone (BCH ID #:103750), Hexa Histidine Anchor (BCH ID #: 103022), Phosphoribosyl-ATP Pyrophosphorylase (PR-ATP synthetase) (BCH ID #:46077), Sinapoylglucose:choline sinapoyltransferase (SCT); sinapine synthase (BCH ID #:101519), Zeaxanthin epoxidase (BCH ID #:100278), E4 protein (BCH ID #:45814), Hemagglutinin (HA) (BCH ID #:45883), protein crystal (BCH ID #:102269), Truncated Cry 1Ac protein (BCH ID #:103215), Cry1Ab/Ac protein (BCH ID #:103109), 5-enolpyruvylshikimate-3-phosphate synthase (BCH ID #:45913), Sucrose:sucrose 1-fructosyl transferase (BCH ID #:46095), nitrate reductases (BCH ID #:46097), *GIGANTEA* protein (BCH ID #:45816), Killer protein 4 (BCH ID #:47790), L1 protein (BCH ID #:45809), L2 protein (BCH ID #:45810), Lactoferrin (BCH ID #:45794), Luciferase alpha subunit (BCH ID #:100377), Luciferase beta subunit (BCH ID #:100378), Matrix protein (M1) (BCH ID #:45881), Intimin (BCH ID #:45843), Human Metallothionenin 1A (BCH ID #:104312), Major histocompatibility complex class I (BCH ID #:45899), Major histocompatibility complex class II (BCH ID #:45900; BCH ID #:45903; BCH ID #:45904), Major histocompatibility complex class I (BCH ID #:45901; BCH ID #:45902), Myostatin (BCH ID #:45853), Newcastle disease virus fusion (F) protein (BCH ID #:48971), NodZ (BCH ID #:45910), NolL (BCH ID #:45911), Non-structural protein (NS2) (BCH ID #:45898), Nopaline synthase (BCH ID #:15171), Nucleoprotein (NP) (BCH ID #:45880), Galactosidase (BCH ID #:45875), Beta-lactoglobulin (BCH ID #:45848), Orotidine-5'-phosphate decarboxylase (BCH ID #:46076), Orotidine-5'-phosphate decarboxylase (BCH ID #:46080), P2X2 protein (BCH ID #:45878), Polymerase PA subunit (BCH ID #:45895), Polymerase PB1 subunit (BCH ID #:45886), Polymerase PB2 subunit (BCH ID #:45894), Phosphofructokinase (BCH ID #: 104350), Phosphomannose Isomerase (PMI) protein (BCH ID #: 15003), Phytoene Synthase 1 (BCH ID #:103620), Proteinase inhibitor II (BCH ID #:104338), Galectin-1 (LGALS1) (BCH ID #:45796), Polyhedrin (BCH ID #:46002), PRP8 (BCH ID #:45908), PRP8 (BCH ID #:45909), E7 protein (BCH ID #:45808), Renin-2 (BCH ID #:45815), delta-endotoxin mCry3A (BCH ID #:43634), RNA 1 Polymerase (BCH ID #:101870), Silk Proteinase Inhibitor 2 (BCH ID #:104313), Cry1C protein (BCH ID #:103217), Stilbene Synthase (BCH ID #:101520), Talin Protein (BCH ID #:45799), Tetanus toxoid (BCH ID #:101618), Tetracycline-controlled transactivator (BCH ID #:101475), Cry1Ab delta-endotoxin (BCH ID #:14985), Acetolactate Synthase (synthetically modified) (BCH ID #:100268), 3"(9)-O-aminoglycoside adenylyl transferase (BCH ID #:15033), 1-aminocyclopropane-1-carboxyllic acid synthase (BCH ID #:15014), 1-amino-cyclopropane-1-carboxylic acid synthase (BCH ID #:15012), 1-amino-cyclopropane-1-arboxylic acid deaminase (BCH ID #:15013), Acetohydroxyacid synthase (AKA Acetolactate synthase; ALS) (BCH ID #:48364), Acetolactate synthase (BCH ID #:15007), Thermostable alpha-amylase (BCH ID #:14966), Mycolyl-Transferase/Antigen 85A (BCH ID #:45818), Aminoglycoside 3 phosphotransferase II (APH-II) (BCH ID #:14967), barstar ribonuclease inhibitor (BCH ID #:14974), Branching Enzyme 1 (BCH ID #:48366), Branching Enzyme 2 (BCH ID #:48453), Beta-galactoside alpha-2;6-sialyltransferase (BCH ID #:45800), Alpha S1 caesin (BCH ID #:45795), PLRV Coat Protein (BCH ID #:103751), CMV viral coat protein (BCH ID #:15027), PEMV viral coat protein (CP) (BCH ID #:101930), PPV viral coat protein (BCH ID #:104309), PRSV viral coat protein (CP) (BCH ID #:15026), Pea Seed-borne Mosaic Virus coat protein (CP) (BCH ID #:101940), PVY viral coat protein (BCH ID #:15020), WMV-2 viral coat protein (BCH ID #:15024), ZYMV viral coat protein (BCH ID #:15025), 5-enolpyruvulshikimate-3-phosphate synthase (BCH ID #:14979), Cry1A.105 protein (BCH ID #:43771), cry1Ac delta-endoxin (BCH ID #: 14986), cry1F delta-endotoxin (BCH ID #: 14987), Cry2Ab delta-endotoxin (BCH ID #:14988), Crystal Cry2Ae protein (BCH ID #:101895), Cry34Ab1 delta-endotoxin (BCH ID #:14994), Cry35Av1 delta-endotoxin (BCH ID #:14995), cry3A delta-endotoxin (BCH ID #:14989), Cry3Bbl protein (BCH ID #:14993), Cry9c delta-endotoxin (BCH ID #:14996), Acyl-lipid desaturase (BCH ID #:102160), E2 protein (BCH ID #:45804), E6 protein (BCH ID #:45807), endochintinase (BCH ID #:100280), 5-enolpyruvylshikimate-3-phosphate synthase (BCH ID #:15000; BCH ID #:45463; BCH ID #:101942), Feline leukemia virus envelope glycoprotein (BCH ID #:45046), Feline Leukemia Virus gag proteins (BCH ID #:45047), Feline Leukemia Virus Reverse Transcriptase (BCH ID #:45048), Dihydroflavonol-4-reductase (BCH ID #:15009), N-acetylglucosaminidase (BCH ID #:45945), Stomatal density and distribution (BCH ID #:48460), Stomatal density and distribution (BCH ID #:48458), Homologues of *Cladosporium fulvum* Resistance genes of the Vf region (HcrVf) (BCH ID #:103738), Phosphinothricin N-acetyltransferase (PAT) (BCH ID #:14972), delta(12)-fatty acid dehydrogenase (BCH ID #:100267), Glyphosate oxidoreductase (BCH ID #: 14998), Granule-bound starch synthase (BCH ID #:48072), Green Fluorescent Protein (BCH ID #:45846), HSP70 (BCH ID #:101614; BCH ID #:45839; BCH ID #:45916), *Hordeum vulgare* sucrose transporter (BCH ID #:45917), *Hordeum vulgare* sucrose transporter 1 (HvSUT1) (BCH ID #:101594), Hygromycin B phosphotransferase (BCH ID #:100292; BCH ID #:14991), Luciferase alpha and beta subunit fusion Protein (BCH ID #: 103755), LuxA; LuxB; LuxC; LuxD; LuxE (BCH ID #:45874), Matrix protein (M2) (BCH ID #:45882), Major Spidroin I protein (BCH ID #:48455), Major Spidroin II protein (BCH ID #:48456), PK Protein Kinase (BCH ID #: 103650), Cry2Ab2 protein (BCH ID #:43772), Lipoxygenase 3 (BCH ID #:48030), Neuraminidase (NA) (BCH ID #:45885), Non-structural protein (NS1) (BCH ID #:45896), Neomycin Phosphotransferase II (BCH ID #: 15001), Quinolinic Acid Phosphoribosyltransferase (QPT) (BCH ID #:15416), Replicase/RNA-dependent RNA polymerase [Potato leafroll virus] (BCH ID #:15019), Helicase (BCH ID #:15018), Phosphinothricin N-acetyltransferase (PAT) (BCH ID #:15002), myo-inositol-hexakisphosphate-3-phosphohydrolase (3-phytase) (BCH ID #:15378), Polygalacturonase (BCH ID #:15015), Fibrinogen (BCH ID #:45801), Glycoprotein (BCH ID #:100344), Red Fluorescent Protein (BCH ID #:103740), Resistance gene 1 (BCH ID #:41317; BCH ID #:102164; BCH ID #:102155), Resistance gene 2 (BCH ID #:41318), Resistance gene 3 (BCH ID #:102165)), S-adenosylmethionine hydrolase (BCH ID #:15387), S-adenosylmethionine (SAM) hydrolase (BCH ID #: 15017), scFv BA 1 (BCH ID #: 103024), Synthetic spider silk protein (BCH ID #:48457), Thioesterase (TE) (BCH ID #: 15005), Beta-Glucuronidase (BCH ID #:46004), Amino acid permease 1 (BCH ID #:48368), Vegetative insecticidal protein 3A (BCH ID #: 14990), Capsid protein VP60 (BCH ID #:102024), WRKY45 Transcription Factor (BCH ID #:103726), Alpha-hordothionine (BCH ID #:46091), Chaperonin containing t-complex polypeptide 1 (BCH ID #:45840; BCH ID #:45915), endo-(1;3-1;4)-beta-glucanase (BCH ID #:100274), telAB protein (BCH ID #:103758), kilA protein (BCH ID #:103757), Large subunit of the ribulose-bisphosphate carboxylase (rbcL) ribosomal binding site (BCH ID #:102611), Translocated Intimin Receptor (BCH ID #:45845), insulin (BCH ID #:102337), Vegetative insecticidal protein 3Aa20 (BCH ID #: 100887), and Glyceraldehyde-3-phosphate dehydrogenase (GAPDH) (BCH ID #:45836; BCH ID #:45838).

The term "haploinsufficient gene" as used herein refers to a gene, or a group of paralogous genes being substantially functionally redundant, which are present in the genome of an organism in which a reduction in the levels of expression relative to a wildtype situation causes a phenotype resulting in a competitive fitness reduction and where this phenotype might only be partially rescued by a single transgenic allele including a single copy or multiple rescue copies of the haploinsufficient gene, e.g. one or more underdominant constructs. The suitability of a haploinsufficient gene for an approach as envisaged herein may be tested by any suitable experiment or be based on any suitable molecular situation. For example, experimental data that can be used to indicate a gene or a paralogous family of functionally redundant genes as being suitably haploinsufficient. Such experimental data may include phenotypic data from heterozygotes, of null mutations, of hypomorphic mutations, of low-expressivity alleles, of chromosomal aneuploids and of chromosomal deletions. Further techniques which can suppress specific genes or gene families though enhanced mRNA degradation or inhibiting mRNA translation may also provide evidence to support haploinsufficiency. Data suggesting haploinsufficiency in one species can indicate haploinsufficiency in homologous genes in other species and may accordingly be used as starting point for corresponding experiments.

Haploinsufficiency may be considered in certain embodiments as a dominant dosage effect of a phenotype arising when there is only a normal level of expression from one gene copy, e.g. if a single gene copy is insufficient to maintain a wildtype expression state. Haploinsufficiency is, for example, associated with certain protein components that make up ribosomes. Ribosomes typically contain ~60-80 protein components across species, designated as Cytoplasmic Ribosomal Proteins (CRPs) or mitochondrial Ribosomal Proteins (MRPs). Mutations resulting in a loss of CRP function may typically result in a phenotype of reduced fitness, e.g. Minute phenotype, when hemizygous or heterozygous and may be lethal as homozygotes. In *Drosophila melanogaster* this phenotype can be associated with a longer development time, thinner bristles, and a reduction in viability and fertility, assumed to result from a reduction in the rate of protein production (see also Marygold et al. 2007, Genome Biol. 8:R216), as well as a several morphological defects. Haploinsufficiency linked to Cytoplasmic Ribosomal Proteins may be encountered in a broad variety of organisms and has been described over a wide range of sexually reproducing species including humans (see Gazda, H. T. et al., 2004, Br. J. Haematol. 127:105-113), mice (see Oliver et al., 2004, Development 131:3907-3920), zebrafish (see Amsterdam et al., 2004, PLoS Biol. 2:E139), the plant *Arabodopsis thaliana* (see Weijers et al, 2001, Development 128:4289-4299), and in yeast (see Deutschbauer et al., 2005, Genetics 169: 1915-1925).

Haploinsufficiency may, apart from CRP loci, also include or be associated with several other genes in several organisms. Examples of haploinsufficient genes envisaged by the present invention are provided in the following Table 1:

RPS10B, DPP, RPL37A, RPL36A, RPS13, RPL13, RPL7, RPL9, RPL24, RPL31, RPS11, RPS15, RPL18A, RPL11, RPL23, RPL12A, RPL39A, RPL23A, RPL8, RPL28, RPL18, RPL14, RPS4, RPL10, RPL35A, RPL13A, RPL34B, SU(VAR)3-9, ABD-B, RPS3, RPL27, RPL4, RPS8, RPL32, RPS7, RPL6, N, HUPB, RUN, S, PKD2, B, MHC, LOK, VG, NP/CG34350C, PCL, BSD, DLL, KR, MTRM, PC, SCR, TM2, ACT88F, UBX, DL, BNL, H, E, P53, MLC2. Also envisaged are homologs of these genes in other species. In a preferred embodiment, a method for reducing the competitive fitness of an organism as defined herein may be carried out in *Drosophila melanogaster* on the basis of one or more of these haploinsufficient genes. In further embodiments, a method for reducing the competitive fitness of an organism as defined herein may be carried out in a different organism, e.g. in a fly, insect or arthropod, on the basis of a homolog of one or more of these haploinsufficient genes.

In further embodiments, a haploinsufficient gene according to the present invention may be a gene selected from the list of *Homo sapiens* genes TP73, DFFB, KCNAB2, CHD5, CAMTA1, PINK1, SAM68, KCNQ4, GLUT1, MYH, FOXE3, HUD, INK4C, NFIA, CCN1, ABCA4, WNT2B, ADAR, ATP1A2, MPZ, MYOC, HRPT2, LRH-1, IRF6, PROX1, TP53BP2, NLRP3, ID 2, MYCN, GCKR, SPAST, MSH6, FSHR, SPR, PAX8, SMADIP1, RPRM, SCN1A, HOXD13, COL3A1, SLC40A1, SATB2, SUMO1, BMPR2, XRCC5, PAX3, STK25, CHL1, SRGAP3, VHL, GHRL, PPARG, SRG3, RASSF1A, TKT, MITF, FOXP1, ROBO1, DIRC2, ATP2C1, FOXL2, ATR, SI, TERC, SOX2, OPA1, TFRC, FGFR3, LETM1, SH3BP2, MSX1, RBPJ, PHOX2B, ENAM, MAPK10, PKD2, SNCA, RIEG, ANK2,

TABLE 1

| Kingdom | Species | CRP genes | Reference | Other genes | Reference |
|---|---|---|---|---|---|
| Animals | *Caenornabaitis elegans* (nematode) | | | gld-1 | Jones and Schdel 1995 |
| | *Drosophila melanogaster* (fruitfly) | 64 CRPs | Marygold et al. 2007 | Mtc-2 | Warmke et al. 1992 |
| | *Nasonia vitripennis* (wasp) | | | ho | Pultz et al. 2000 |
| | *Tribolium castaneum* (flour beetle) | | | mxp | Shippy et al. 2000 |
| | *Felis sylvestris* (cat) | | | CRX | Menotti-Raymond et al. 2010 |
| | *Canis lupus* (dog) | | | T | Haworth et al. 2001 |
| | *Mesocricetus auratus* (hamster) | | | Wh | Hodgkinson et al. 1998 |
| | *Mus musculus* (mouse) | RpL 24 | Oliver et al. 2004 | Dli4 | Krebs et al. 2004 |
| | *Rattus norvegicus* (rat) | | | TSC2 | Habib et al, 2008 |
| | *Homo sapiens* (human) | RpS 19 | Choesmel et al. 2007 | Nkx2-1 | Pohienz et al. 2002 |
| | *Mecaca mulatta* (macaque) | | | TCOF1 | Shows et al. 2006 |
| | *Danio reno* (zebrafish) | 11 CRPs | Amsterdam et al. 2004 | | |
| Fungi | *Aspergillus nidulans* (mold) | | | prpA | Semighini et al. 2006 |
| | *Candida albicans* (gut yeast) | | | CBK1 | Uhi et al. 2003 |
| | *Saccharomyces cerevisiae* (brewer's yeast) | 72 CRPs | Deutschbauer et al. 2005 | TLC1 | Mozdy and Cech 2006 |
| | *Schizosaccharomyces pombe* (fission yeast) | 8 CRPs | Kim et al. 2010 | taf12 | Kim et al. 2010 |
| Plants | *Arabidopsis thaliana* (thale cress) | AtRpS5a/b | Weijers et al. 2001 | ERL2 | Piliterri et al. 2007 |
| | *Pisum sativum* (pea) | | | CRY1 | Platten et al. 2005 |
| | *Solanum lycopersicum* (tomato) | | | CRY1 | Welier et al. 2001 |

Further envisaged examples of haploinsufficent genes include a transcription factor (further details may be derived from Seidman and Seidman, 2002, The Journal of Clinical Investigation, 109: 451-455); a tumor suppressor gene (further details may be derived from Santarosa and Ashworth, 2004, Biochimica et Biophysica Acta (BBA)—Reviews on Cancer 1654: 105-122); a gene related to muscle function, or a homeodomain protein coding gene (further details may be derived from Cook, et al., 2012, Genome Biology 13:R21).

Particularly envisaged examples of haploinsufficient genes, which can be used within the context of the present invention, include the *Drosophila melanogaster* genes RPL36, RPL35, RPL17, RPS6, RPL37A, RPS19A, RPS5A, MAD2L1, PLK4, FBXW7, TERT, SEMA5A, GDNF, FGF10, PIK3R1, APC, RAD50, SMAD5, EGR1, TCOF1, NPM1, NKX2-5, MSX2, NSD1, FOXC1, DSP, EEF1E1, TNXA, TNX, HMGA1, RUNX2, CD2AP, ELOVL4, NT5E, SIM1, COL10A1, PARK2, TWIST1, GLI3, GCK, FKBP6, ELN, LIMK1, RFC2, GTF3, GTF2I, NCF1, KRIT1, COL1A2, SHFM1, RELN, FOXP2, CAV1, ST7, BRAF, SHH, HLXB9, GATA4, NKX3-1, FGFR1, CHD7, CSN5, EYA1, TRPS1, DMRT1, DMRT2, MLLT3, ARF, CDKN2B, BAG1, PAX5, GCNT1, ROR2, PTCH1, NR5A1, LMX1B, ENG, TSC1, COL5A1, NOTCH1, EHMT1, KLF6, GATA3, ANX7, PTEN, PAX2, FGF8, BUB3, CDKN1C, NUP98, PAX6, WT1, EXT2, ALX4, FEN1, SF1, FGF3, FZD4, ATM, H2AX, FLI1, NFRKB, PHB2, ETV6, CDKN1B, COL2A1, KRT5, MYF6, IGF1, SERCA2, TBX5, TBX3, HNF1A, BRCA2, FKHR, RB1, ZIC2, LIG4, COCH, NPAS3, NKX2-1, PAX9, BMP4, GCH1, SIX6, RAD51B, BCL11B, SPRED1, BUBR1, DLL4, FBN1, ALDH1A2, TPM1, P450SCC, BLM, COUP-TFII, SOX8, TSC2, PKD1, CBP, SOCS1, PRM2, PRM1, ABCC6, ERAF, SALL1, CBFB, CTCF, WWOX, FOXF1, FOXC2, YWHAE, HIC1, LIS1, P53, PMP22, COPS3, RAI1, TOP3A, SHMT1, RNF135, NF1, SUZ12, MEL-18, KLHL10, STAT5B, STAT5A, BECN1, BRCA1, PGRN, MAPT, CSH1, POLG2, PRKAR1A, SOX9, NHERF1, FSCN2, DSG1, DSG2, TCF4, FECH, MC4R, GALR1, SALL3, LKB1, PNPLA6, RYR1, TGFB1, RPS19, DMPK, CRX, PRPF31, JAG1, PAX1, GDF5, HNF4A, SALL4, MC3R, RAE1, GNAS, EDN3, KCNQ2, SOX18, SLC5A3, RUNX1, DYRK1A, COL6A1, PRODH, DGCR2, HIRA, TBX1, COMT, RTN4R, PCQAP, LZTR1, INI1, MYH9, SOX10, FBLN1, PPARA, PROSAP2, SHOX, P2RY8, NLGN4X, TRAPPC2, RPS4X, and CSF2RA. Also envisaged are homologs, of these genes in other species. In a preferred embodiment, a method for reducing the competitive fitness of an organism as defined herein may be carried out in a mammal or higher animal on the basis of one or more of these haploinsufficient genes, or on the basis of a homolog of one or more of these haploinsufficient genes.

In an additional group of embodiments, a haploinsufficient gene according to the present invention may be a gene selected from the list of *Arabidopsis thaliana* genes RPSaA, RPSaB, RPS2A, RPS2B, RPS2C, RPS2D, RPS3A, RPS3B, RPS3C, RPS3aA, RPS3aB, RPS4A, RPS4B, RPS4C, RPS4D, RPS5A, RPS5B, RPS6A, RPS6B, RPS7A, RPS7B, RPS7C, RPS8A, RPS8B, RPS9A, RPS9B, RPS9C, RPS10A, RPS10B, RPS10C, RPS11A, RPS11B, RPS11C, RPS12A, RPS12B, RPS12C, RPS13A, RPS13B(A), RPS14A, RPS14B, RPS14C, RPS15A, RPS15B, RPS15C, RPS15D, RPS15E, RPS15F, RPS15aA, RPS15aB, RPS15aC, RPS15aD, RPS15aE, RPS15aF, RPS16A, RPS16B, RPS16C, RPS17A, RPS17B, RPS17C, RPS17D, RPS18A (A), RPS18B (B), RPS18C(C), RPS19A, RPS19B, RPS19C, RPS20A, RPS20B, RPS20C, RPS21A, RPS21B, RPS21C, RPS23A, RPS23B, RPS24A, RPS24B, RPS25A, RPS25B, RPS25C, RPS25D, RPS25E, RPS26B, RPS26A, RPS26C, RPS27A(C), RPS27B (A), RPS27D (B), RPS27aA, RPS27aB, RPS27aC, RPS28A, RPS28B, RPS28C, RPS29A, RPS29B, RPS29C, RPS29D, RPS30A, RPS30B, RPS30C, RPP0A, RPP0B, RPP0C, RPP1A, RPP1B, RPP1C, RPP2A, RPP2B, RPP2C, RPP2D, RPP2E, RPP3A, RPP3B, RPL3A(1), RPL3B(2), RPL3C, RPL4A, RPL4B, RPL4C, RPL4D, RPL5A, RPL5B, RPL5C, RPL6A, RPL6B, RPL6C, RPL7A, RPL7B, RPL7C, RPL7D, RPL7aA, RPL7aB, RPL8A, RPL8B, RPL8C, RPL9A, RPL9B, RPL9C, RPL9D, RPL10A, RPL10B, RPL10C, RPL10aA, RPL10aB, RPL10aC, RPL11A(A), RPL11B, RPL11C(B), RPL11D, RPL12A, RPL12B, RPL12C, RPL13A, RPL13B, RPL13C, RPL13D, RPL13aA, RPL13aB, RPL13aC, RPL13aD, RPL14A, RPL14B, RPL15A, RPL15B, RPL17A, RPL17B, RPL18A, RPL18B, RPL18C, RPL18aA, RPL18aB, RPL18aC, RPL19A, RPL19B, RPL19C, RPL21A, RPL21B, RPL21C, RPL21D, RPL21E, RPL21F, RPL22A, RPL22B, RPL22C, RPL23A, RPL23B, RPL23C, RPL23aA(2), RPL23aB(3), RPL24A, RPL24B, RPL26A, RPL26B, RPL27A, RPL27B, RPL27C, RPL27aA, RPL27aB, RPL27aC, RPL28A, RPL28B, RPL28C, RPL29A, RPL29B, RPL30A, RPL30B, RPL30C, RPL31A, RPL31B, RPL31C, RPL32A, RPL32B, RPL34A, RPL34B, RPL34C, RPL35A, RPL35B, RPL35C, RPL35D, RPL35aA, RPL35aB, RPL35aC, RPL35aD, RPL36A, RPL36B, RPL36C, colRPL36aA, RPL36aB, RPL37A, RPL37B, RPL37C, RPL37aA, RPL37aB, RPL37aC, RPL38A, RPL38B, RPL39A, RPL39B, RPL39C, RPL40A, RPL40B, RPL41A, RPL41B, RPL41C, RPL41D, RPL41E, RPL41F and RPL41G. Also envisaged are homologs of these genes in other species. In a preferred embodiment, a method for reducing the competitive fitness of an organism as defined herein may be carried out in *Arabidopsis thaliana* on the basis of one or more of these haploinsufficient genes. In further embodiments, a method for reducing the competitive fitness of an organism as defined herein may be carried out in a different organism, e.g. in a different plant, on the basis of a homolog of one or more of these haploinsufficient genes. Particularly preferred is the use of the haploinsufficient gene RpL14 (having HomoloGene accession number: 68375) or Rpl 23aA (having HomoloGene accession number: 110453).

In a first step of the method for reducing the competitive fitness of an organism according to the invention the expression of a haploinsufficient gene in the organism is reduced. The reduction may be a reduction of the normal or typical wildtype expression of one haploinsufficient gene by a value of about 10% 20%, 25%, 30%, 40%, 50%, 60%, 70%, 80%, 90%, 95%, 96%, 97%, 98%, 99% or 100% in hemizygotes.

It is preferred that this reduction occurs in at least a subset of cells which are haploinsufficient sensitive which can be contributed to a fitness reducing phenotype. It is understood that in some embodiments not all cells are haploinsufficient sensitive. For instance, in view of the limited nature of the described phenotypes of, e.g. *Drosophila* Minute mutations is assumed that a subset of cells may experience a deficit in protein synthesis and contribute to a deleterious phenotype, while other cells may not experience such a deficit. Suitable techniques and approaches to distinguish between these cell groups would be known to the skilled person. Tissues that might experience haploinsufficiency can be identified using standard methods, e.g. mRNA expression such as Northern analysis tests and/or translated polypeptides may be tested via Western analysis tests or Coomassie staining or isotopic pulse-chase experiments. Further details and additional tests may be derived from qualified textbooks, e.g. from Ausubel et al., eds, 2007, Current Protocols in Molecular Biology, John Wiley & Sons, Inc., New York. The role that any tissues identified as being sensitive to haploinsufficiency could play in potentially fitness reducing phenotypes can be investigated using a range of using standard methods e.g. measuring competitive fitness of genotypes in the type of multi-generational experiment described in Example 5, while specifically targeting haploinsufficiency to candidate cell types. Tissue specific targeting can be achieved by placing genes reducing the expression of a haploinsufficient gene under the control of tissue specific promoters.

A normal or typical wildtype expression of the haploinsufficient gene is understood as the expression of the haploinsufficient gene in a typical physiological situation without influence of stress factors or growth interference or inhibition. The reduction of the expression of the haploinsufficient gene may be provided on all suitable levels of expression. Further envisaged is the use of more than one haploinsufficient gene at a time, i.e. for performing a method of the present invention. For example, 2, 3, 4, 5, 6, 7, 8, 9, 10 or more haploinsufficient genes may be reduced in their activity or functionality according to the principles mentioned herein, e.g. at the same time or in a timely staggered manner.

The reduction may a based, for example, on a permanent modification of all genomic copies of a haploinsufficient gene. An example of such a modification is a deletion, partial deletion or functional modification of all genomic copies of a haploinsufficient gene. Furthermore, genetic elements necessary for the functioning of a haploinsufficient gene such as a promoter, a transcription factor binding site, an enhancer, or a terminator may be modified such that the haploinsufficient gene is no longer expressed or its expression is reduced. In preferred embodiments, the reduction of expression is specific, i.e. it is targeted and non-random with regard to the haploinsufficient gene whose expression should be reduced. This specific reduction essentially excludes random expression reduction based on random-mutagenesis or insertional mutagenesis.

In specific embodiments of the invention the reduction may be based on the presence of a single transgenic locus as defined herein. In a further embodiment, the reduction may be based on multiple transgenic loci as defined herein.

The functional modification of a haploinusufficient gene may be based on the introduction of stop codons thus influencing translation or providing truncated protein species. Alternatively, a modification to the coding sequence may be introduced to a haploinsufficient gene. Such modification may, for example, lead to an exchange of one, two, three or more amino acids at one, two, three or more different sites of the coding sequence. These amino acid exchanges may subsequently prevent the interaction of the encoded protein with other factors, e.g. other proteins, cellular factors or structures. It is preferred that the modification to the coding sequence leads to a reduction or complete abolition of the wildtype functionality of the haploinsufficient gene. The choice for such modification target sites may be made in dependence on structural or functional information on a haploinsufficient gene. Alternatively functional importance could be inferred from the degree of phylogenetic conservation at the level of amino acid residue sequence using. Such information would be known to the skilled person or can be derived from suitable literature or database sources. Examples of suitable databases are NCBI:Homologene, NCBI:Genbank, or EBI: swiss-prot.

In a preferred embodiment the reduction of the expression of a haploinsufficient gene may be based on means which specifically disrupt the haploinsufficient gene DNA sequence. The term "specifically disrupt" as used herein means that an entity is capable of permanently modifying the DNA sequence of a gene, in particular the genomic sequence of a gene, or any extragenomic DNA copy of the gene, in a sequence specific manner. This specificity may be provided by one or more sequence motifs, which are present in the target haploinsufficient gene only (unique sequence motif), e.g. in all alleles of the haploinsufficient genes within a cell or within the genome of an organism. The sequence motifs may, in special embodiments, further be present in ortholog or paralog sequences of the haploinsufficient gene. In a preferred embodiment, such sequence motifs may be present in one gene only, or may be present in no more than two genes unless part of a functionally redundant gene family. Sequence motifs which may be used for such an approach may have any suitable length. The length may be defined according to the size and variability of the genome of the organism in which the disruption is to be carried out. Typically, sequence motifs of about 4 nucleotides to about 150 nucleotides may be used. The usability of the sequence motif may further be checked and verified by comparison with database information, e.g. available genomic information on a target organism. A disruption may lead to a complete or partial absence of the activity of a haploinsufficient gene. The absence of activity may be based on an absence of the protein itself, e.g. due to non-expression, translation difficulties, rapid degradation etc., or it may be based on the provision of proteins, with altered properties, e.g. binding properties, enzymatic activities, localization properties etc. The specific disruption may, in specific embodiments, be a transient disruption, e.g. a disruption, which can be reversed by a further modification of the haploinsufficient gene.

Preferred examples of means, which are able to specifically disrupt the haploinsufficient gene DNA sequence include a zinc finger nuclease (ZFN), a CRISPR, a meganuclease and TALEN (Transcription Activator-Like Effector Nuclease).

The term "zinc finger nuclease" as used herein refers to artificial restriction enzymes, which are typically generated by fusing a zinc finger DNA-binding domain to a DNA-cleavage domain. Zinc finger domains may preferably be engineered or modified in order to target any desired DNA sequence, i.e. a DNA sequence of a haploinsufficent gene according to the present invention. Such engineering methods would be known to the skilled person or can be derived from suitable literature sources such as Bae et al., 2003, Nat Biotechnol, 21, 275-80; Wright et al., 2006, Nature Protocols, 1, 1637-1652.)

Typically, the non-specific cleavage domain from type IIs restriction endonucleases, e.g. from FokI, may be used as the cleavage domain in ZFNs. Since this cleavage domain dimerizes in order to cleave DNA a pair of ZFNs is typically required to target non-palindromic DNA sites. ZFNs envisaged by the present invention may further comprise a fusion of the non-specific cleavage to the C-terminus of each zinc finger domain. For instance, in order to allow two cleavage domains to dimerize and cleave DNA, two individual ZFNs are typically required to bind opposite strands of DNA with C-termini provided in a specific distance. It is to be understood that linker sequences between the zinc finger domain and the cleavage domain may requires the 5' terminus of each binding site to be separated by about 5 to 7 bp. The present invention envisages any suitable ZNF form or variant, e.g. classical FokI fusions, or optimized version of the FokI, as well as enzymes with modified dimerization interfaces, improved binding functionality or variants which are able to provide heterodimeric species. Further details would be known to the skilled person or can be derived from suitable literature sources such as Bitinaite et al. PNAS, 95, 10570-10575 (1998); or Szczepek et. al.. Nature biotechnology 25, 786-93 (2007).

"Meganucleases" are understood as endodeoxyribonucleases, which typically have a recognition site in the form of a double-stranded DNA sequences of about 12 to 40 nucleotides. Meganucleases typically work as molecular DNA scissors which provide the possibility of eliminating or modifying sequences in a sequence specific manner. Examples of suitable meganucleases include intron endonucleases and intein endonucleases. The recognition sequence of a meganuclease may be modified by genetic or protein engineering in order to target any desired DNA sequence, i.e. a DNA sequence of a haploinsufficent gene according to the present invention. In order to provide a sequence specificity the specificity of existing meganucleases may be modified by introducing a variation to the amino acid sequence, followed by the selection of functional proteins. Alternatively, protein domains from different enzymes may be fused to the nucleases, resulting in chimeric meganucleases. Such chimeric meganucleases may have, for example, a new recognition site composed of a half-site of a meganuclease and a half-site of a protein. In further embodiments, both approaches may be combined, i.e. the modification of the binding sequence of the meganuclease and the fusion to a protein domain from a different enzyme. Meganucleases to be used within the context of the present invention may be provided, for instance, on the basis of a technology owned by Cellectis, i.e. based on protein domains from the homodimeric meganuclease I-CreI as well as from other meganucleases scaffolds. Further suitable meganucleases may be engineered according to the technology provided by Precision Biosciences, e.g. the Directed Nuclease Editor (DNE) platform. Further details, in particular with regard to the possibilities of engineering meganucleases, would be known to the skilled person or can be derived from suitable literature sources such as Gao et al., The Plant journal for cell and molecular biology, 61, 176-87 (2010).

Particularly preferred is the use of the TALEN (Transcription Activator-Like Effector Nuclease) system, i.e. an artificial restriction enzyme, which is generated by fusing the TAL effector DNA binding domain to a DNA cleavage domain. TAL effectors are proteins which are typically secreted by Xanthomonas bacteria or related species, or which are derived therefrom and have been modified. The DNA binding domain of the TAL effector may comprise a highly conserved sequence, e.g. of about 33-34 amino acid sequence with the exception of the 12th and 13th amino acids which are highly variable (Repeat Variable Diresidue or RVD) and typically show a strong correlation with specific nucleotide recognition. On the basis of this principle, DNA binding domains may be engineered by selecting a combination of repeat segments containing Repeat Variable Diresidue corresponding to a haploinsufficient gene DNA sequence. The TALEN DNA cleavage domain may be derived from suitable nucleases. For example, the DNA cleavage domain from the FokI endonuclease or from FokI endonuclease variants may be used to construct hybrid nucleases. TALENs may preferably be provided as separate entities due to the peculiarities of the FokI domain, which functions as a dimer. In specific embodiments, the number of amino acid residues between the TALEN DNA binding domain and the FokI cleavage domain and the number of bases between the two individual TALEN binding sites may be modified or optimized according to the sequence of the haploinsufficient gene DNA sequence in order to provide high levels of activity. TALENs or TALEN components may preferably be engineered or modified in order to target any desired DNA sequence, i.e. a DNA sequence of a haploinsufficent gene according to the present invention. Such engineering may be carried out according to suitable methodologies, e.g. Zhang et al., Nature Biotechnology, 1-6 (2011), or Reyon et al., Nature Biotechnology, 30, 460-465 (2012).

The present invention further envisages the use of CRISPR (Clustered Regularly Interspaced ShortPalindromic Repeats). CRISPR can be utilized to reduce expression of specific genes (or groups or similar genes). This is typically achieved through the expression of single stranded RNA in addition to a CRISPR gene. The technique typically relies on the expression of a CRISPR gene such as CAS9 in addition to an RNA guide sequences (see, for example, Cong et al DOI: 1013: 10.1126/science.1231143). Double stranded cleaved may be targeted to specific sequences using the expression of appropriate flanking RNA guide sequences. Chromosomal cleavage could thus locally enhance mutagenesis. This in turn may contribute to a reduction of normal gene expression. Alternatively, CRISPR expression may be used to cleave mRNA, thereby reducing expression. In a preferred embodiment RNA guide sequences and CRISPR gene expression (eg CAS9) may be included as part of an {Ud} construct, e.g. a construct as describe herein. The reduction may alternatively be based on an interference with a transcript of a haploinsufficient gene. For example, the mRNA transcript of a haploinsufficient gene may be recognized and inactivated or degraded according to suitable means known to the person skilled in the art.

In a preferred embodiment the reduction of the expression of a haploinsufficient gene may be based on a means which specifically degrades or directly inactivates the haploinsufficient gene transcript. The term "specifically degrades or directly inactivates" as used herein means that an entity or means is capable of recognizing and inactivating a species of mRNA sequences corresponding to a haploinsufficient gene as defined herein. The inactivation or degradation may be a complete destruction, degradation or degeneration of the mRNA molecule, or it may be a partial degradation or destruction of the mRNA molecule leading to the abolition or prevention of (potential) translational activity based on the mRNA molecule. In further embodiments, the mRNA sequence may be inactivated by a processing, modification, rearrangement, relocalization, storage or other activity performed on the mRNA molecule, which also leads to an abolition or prevention of (potential) translational activity based on the mRNA molecule. The specificity may be provided by one or more sequence motifs, which are present in the transcript(s) of the haploinsufficient gene only (unique sequence motif). The sequence motifs may, in special embodiments, further be present in transcripts of orthologs or paralogs of the haploinsufficient gene. In a preferred embodiment, such sequence motifs may be present in one transcript species only, or may be present in no more than two transcript species. Sequence motifs which may be used for such an approach may have any suitable length. The length may be defined according to the molecular approach chosen, the organism in which the inactivation takes place, the presence and complexity of the transcriptome, or physiological parameters etc. A degradation or inhibition of the haploinsufficient gene transcript may lead to a complete or partial absence of the activity of a haploinsufficient gene. It is preferred that the activity of a haploinsufficient gene is completely absent. The specific inactivation of transcripts may in certain embodiments be a transient inactivation, e.g. an inactivation which can be stopped or paused or terminated in an organism, thus leading to the provision of new transcripts after the termination of the inactivation.

Preferred examples of means which are able to specifically degrade or directly inactivate the haploinsufficient gene transcript include a siRNA molecule, a miRNA molecule, an antisense nucleic acid molecule, e.g. RNA or DNA molecule, or an agent which conveys RNA-directed DNA methylation.

The term "siRNA" as used herein refers to a particular type of antisense-molecule, namely small inhibitory RNA duplexes that induce the RNA interference (RNAi) pathway. These molecules can vary in length and may be between about 18 to 28 nucleotides in length, e.g. have a length of 18, 19, 20, 21, 22, 23, 24, 25, 26, 27 or 28 nucleotides. Preferably, the molecule has a length of 21, 22 or 23 nucleotides. The siRNA molecule according to the present invention may contain varying degrees of complementarity to their target mRNA, preferably in the antisense strand. siRNAs may have unpaired overhanging bases on the 5' or 3' end of the sense strand and/or the antisense strand. The term "siRNA" also includes duplexes of two separate strands, as well as single strands that can form hairpin structures comprising a duplex region. Preferably, the siRNA may be double-stranded wherein the double-stranded siRNA molecule comprises a first and a second strand, each strand of the siRNA molecule is about 18 to about 23 nucleotides in length, the first strand of the siRNA molecule comprises a nucleotide sequence having sufficient complementarity to the target RNA via RNA interference, and the second strand of said siRNA molecule comprises a nucleotide sequence that is complementary to the first strand. Methods for designing suitable siRNAs directed to a given target transcript, i.e. haploinsufficient gene transcript, are known to person skilled in the art, e.g. from Elbashir et al., 2001, Genes Dev. 15, 188-200. Also preferred are siRNAs against a haploinsufficient gene transcript which are provided in the form of short hairpin RNAs. Such short hairpin RNAs may be produced or designed according to any suitable method or technique known to the person skilled in the art. For example, a tool like the one provided at molgyn.kgu.de/genesilencer/genesilencer.html (Kappel et al., Nature Protocols, 2007, 2(12):3257-69), may be used in order to design haploinsufficient gene transcript specific hnRNA molecules. A short hairpin RNA or short hairpin RNA encoding molecule may comprise a first recombinant nucleic acid molecule, comprising at least a first sequence corresponding to a stretch of a haploinsufficient gene transcript and at least a second sequence corresponding to the reverse complement of said first sequence. The stretch may comprise between 17 and 25 nucleotides, preferably between 18 and 22, more preferably 19 nucleotides. Additionally, or optionally, a loop sequence may be present between the two stretches of nucleic acid sequence. This loop sequence may have a length of between about 6 to 12 nucleotides, preferably a length of 9 nucleotides. Furthermore, the short hairpin RNA or short hairpin RNA encoding molecule may comprise a terminator signal and/or sequences comprising restriction sites for endonucleases. The at least first sequence corresponding to a haploinsufficient gene transcript and at least a second sequence corresponding to the reverse complement of said first sequence may be either entirely complementary to the sequence of a haploinsufficient gene transcript or its reverse complement, or the sequences may comprise one or more mismatches, e.g. 1, 2, 3, 4, or 5 mismatches.

The term "miRNA" or "microRNA" as used herein refers to a short single-stranded RNA molecule of typically 18-27 nucleotides in length, which regulates gene expression. miRNAs are typically encoded by genes from whose DNA they are transcribed but are not translated into a protein. In a natural context miRNAs are first transcribed as primary transcripts or pri-miRNA with a cap and poly-A tail and processed to short, 70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). This complex is believed to be responsible for the gene silencing observed due to miRNA expression and RNA interference. Either the sense strand or antisense strand of DNA may function as templates to give rise to miRNA. Typically, efficient processing of pri-miRNA by Drosha requires the presence of extended single-stranded RNA on both 3'- and 5'-ends of hairpin molecule. These ssRNA motifs could be of different composition while their length is of high importance if processing is to take place at all. Generally, the Drosha complex cleaves the RNA molecule about 22 nucleotides away from the terminal loop. Pre-miRNAs may not have a perfect double-stranded RNA (dsRNA) structure topped by a terminal loop. When Dicer cleaves the pre-miRNA stem-loop, typically two complementary short RNA molecules are formed, but only one is integrated into the RISC complex. This strand is known as the guide strand and is typically selected by the argonaute protein, the catalytically active RNase in the RISC complex, on the basis of the stability of the 5' end. The remaining strand, known as the anti-guide or passenger strand, is typically degraded as a RISC complex substrate. After integration into an active RISC complex, miRNAs may base pair with their complementary mRNA molecules and inhibit translation or may induce mRNA degradation by the catalytically active members of the RISC complex, e.g. argonaute proteins. Mature miRNA molecules are typically at least partially complementary to transcripts of a haploinsufficient gene according to the present invention. Preferably, miRNAs as envisaged by the present invention may be identifiable and/or obtainable according to assays and methods described in Hüttenhofer and Vogel, 2006, NAR, 34(2): 635-646. They may be, for example, 100% complementary to their target sequences, i.e. haploinsufficient gene transcripts. Alternatively, they may have 1, 2 or 3 mismatches, e.g. at the terminal residues or in the central portion of the molecule. miRNA molecules according to the present invention may have a length of between about 18 to 27 nucleotides, e.g. 18, 19, 20, 21, 22, 23, 24, 25, 26 or 27 nucleotides. Preferred are 21 to 23 mers. miRNAs having 100% complementarity may preferably be used for the degradation of transcripts of haploinsufficient genes according to the present invention, whereas miRNAs showing less than 100% complementarity may preferably be used for the blocking of translational processes.

The term "antisense molecule" refers to a nucleic acid which is at least partially complementary to the transcript of a haploinsufficient gene as defined herein. The antisense molecule of the invention may comprise, for example, a sequence complementary to at least a portion of a haploinsufficient gene transcript as defined herein. Antisense molecules may further be complementary to the coding region sequence of a haploinsufficient gene transcript or complementary to the transcribed untranslated region of a haploinsufficient gene transcript. The complementary dsRNA that a RNAi targeting molecule might be derived from may have different lengths, e.g. from about 21 to 1000 bp, preferably about 21, 40, 100, 200, 300, or 1000 bp or longer, or any value in between these values. These dsRNAs may accordingly be processed by a variety of pathways into catalytically active RNase in the RISC complex.

It is preferred that the antisense molecule is complementary to the transcribed translated or transcribed untranslated region of a haploinsufficient gene transcript. Generally, antisense molecules can be used to control gene expression via antisense DNA or RNA, or through triple-helix formation. The antisense molecule of the invention may typically comprise a sequence, which is complementary to at least a portion of a haploinsufficient gene transcript. Absolute complementarity, although preferred, is not required. A sequence "complementary to at least a portion of a haploinsufficient gene transcript" as referred to herein, means a sequence having sufficient complementarity to be able to hybridize with the transcript, thus forming a stable duplex triplex formation. The ability to hybridize will depend on both the degree of complementarity and the length of the antisense nucleic acid. Generally, the larger the hybridizing nucleic acid, the more base mismatches with a transcript it may contain and still form a stable duplex or triplex. A person skilled in the art would know how to determine a tolerable degree of mismatch by use of standard procedures to determine the melting point of the hybridized complex. The antisense molecule may further be complementary to any part of the mRNAs expressed by the target gene. Preferably antisense molecules complementary to the 5' end of the transcript, e.g., the 5' untranslated sequence up to and including the AUG initiation codon may be used in or for the inhibition of translocation. In a further preferred embodiment, sequences complementary to the 3' untranslated sequences of transcripts may also be used.

An antisense molecule according to the present invention may be DNA or RNA or chimeric mixtures or derivatives or modified versions thereof, single-stranded or double-stranded.

The term "agent conveying RNA-directed DNA methylation" refers to a nucleic acid which is capable of silencing a haploinsufficient gene according to an epigenetic process. RNA-directed DNA methylation or RdDM is typically present in plant and animal cells and may be conveyed by short double-stranded RNA molecules or dsRNAs. These RNAs are typically processed by a cell and may lead to a methylation of complementary genomic loci and thereby interfere with the transcription from these loci via interaction with histone residues.

In a further specific embodiment of the invention the means which specifically degrades or inactivates the haploinsufficient gene transcript may be a catalytic RNA or a ribozyme. The term "catalytic RNA" or "ribozyme" refers to a non-coding RNA molecule, which is capable of specifically binding to a target mRNA, i.e. a haploinsufficient gene transcript, and of cutting or degrading said target mRNA. Typically, ribozymes cleave mRNA at site specific recognition sequences and may be designed, engineered and used to destroy haploinsufficient gene transcripts according to the present invention. An envisaged example of a ribozyme is a hammerhead ribozyme. Hammerhead ribozymes typically cleave mRNAs at locations dictated by flanking regions that form complementary base pairs with the target mRNA. The construction and production of hammerhead ribozymes is known in the art and is described in Haseloff and Gerlach, 1988, Nature, 334: 585-591. Preferably, the ribozyme may be engineered so that the cleavage recognition site is located near the 5' end of the haploinsufficient gene transcript.

In a further alternative embodiment, the reduction of the expression of a haploinsufficient gene in the organism may be based on interference with the expressed protein product of a haploinsufficient gene. For example, any suitable means known to interfere with the presence and/or amount of an expressed protein product of a haploinsufficient gene is envisaged by the present invention. Such means could, for example, be an antagonist of the expressed protein product of a haploinsufficient gene. Examples of suitable antagonists include a compound directly or indirectly inhibiting or modulating the activity of the expressed protein product of a haploinsufficient gene, a dominant negative variant of the expressed protein product of a haploinsufficient gene, an aptamer specific for the expressed protein product of a haploinsufficient gene, an antibody or intrabody against the expressed protein product of a haploinsufficient gene or a small molecule capable of specifically binding to the expressed protein product of a haploinsufficient gene.

A "compound directly inhibiting or modulating the activity of an expressed protein product of a haploinsufficient gene" may be any compound which is capable of decreasing the activity of expressed protein product of a haploinsufficient gene and which is directly interacting, e.g. by binding, to the expressed protein product of a haploinsufficient gene. Such a compound may, for example, be an interactor which has negative influence on the catalytic activity protein product of a haploinsufficient gene, e.g. by obstructing further interaction or binding surfaces or pockets.

A "compound indirectly inhibiting or modulating the activity of an expressed protein product of a haploinsufficient gene" may be any compound which is capable of decreasing the activity of an expressed protein product of a haploinsufficient gene by an interaction with a direct interactor of a protein product of a haploinsufficient gene or via an indirect working pathway not involving an interaction with a protein product of a haploinsufficient gene. Examples of such interactors include enzymatic activities degrading activators of protein products of a haploinsufficient gene or proteins capable of binding and quenching activators of a protein product of a haploinsufficient gene. Alternatively, such interactors may positively modulate activities leading to a degradation of a protein product of a haploinsufficient gene, e.g. a proteinases.

A "dominant negative variant of the expressed protein product of a haploinsufficient gene" may be a protein, which comprises an antimorphic modification, which adversely affects the expressed protein product of a haploinsufficient gene. Typically, a dominant negative behavior may occur if the antimorphic variant can interact with the expressed protein product of a haploinsufficient gene but blocks some aspect of its function. Such variants may, for example, comprise or lack specific domains of the expressed protein product of a haploinsufficient gene, e.g. one or more protein-protein interacting or dimerization domains, complex assembly domains, one or more membrane-associated domains etc. This is particularly of importance in a protein that functions as a dimer or multimer. If, for example, one part of that protein complex is mutant in some functional aspect of the multimer but is still able to form the multimer it may have a dominant effect on the other wildtype portions of the complex, and a negative effect if the mutation prevents the complex from carrying out its normal function. A dominant-negative form can, for example, specifically block the action of the expressed protein product of a haploinsufficient gene from which it was derived.

An "aptamer specific for the expressed protein product of a haploinsufficient gene" may be a short peptide capable of interacting with and specifically binding to the expressed protein product of a haploinsufficent gene as defined herein. Such a peptide aptamer may contain a variable peptide loop, comprising for example, 10 to 20 amino acids. In the context of the present invention the peptide aptamer may preferably be attached at one or both ends to a scaffold structure. The scaffold structure may be any molecule, preferably a protein, which has good solubility and capacity properties. Suitable scaffold molecules would be known to the person skilled in the art. A preferred scaffold molecule to be used in the context of the present invention is the bacterial protein thioredoxin A.

An "antibody against the expressed protein product of a haploinsufficient gene" may any immunoglobulin molecule and immunologically active portions of an immunoglobulin molecule, i.e. molecules that contain an antigen binding site that immunospecifically binds an antigen or epitope present on a protein product of a haploinsufficient gene. The immunoglobulin molecules can be of any type (e.g., IgG, IgE, IgM, IgD, IgA and IgY), class (e. g., IgG1, IgG2, IgG3, IgG4, IgA1 and IgA2) or subclass of immunoglobulin molecule. Such an antibody may be a monoclonal, multi-specific, human, humanized or chimeric antibody, a single chain antibody, Fab fragment, Fab' fragment, diabody, or epitope-binding fragments of any of the above. In a preferred embodiment, the antibody binding an antigen or epitope present on a protein product of a haploinsufficient gene is capable of interfering with the activity or function of the bound protein product. Such an interference may be, for example, a reduction of activity, inhibition of activity, deviation from normal localization, inhibition or reduction of interaction with other proteins, degradation, partial degradation etc.

An "intrabody against the expressed protein product of a haploinsufficient gene" as used herein is an antibody that works within the cell. The intrabody is preferably modified for intracellular localization. In certain embodiments, intrabodies may show special alterations such as a modification of immunoglobulin VL domains for hyperstability, provision of resistance to a reducing intracellular environment, or expression as a fusion protein with maltose binding protein or other stable intracellular proteins. In further embodiments, the intrabody may be a single-chain antibody (scFvs). In a preferred embodiment, the intrabody binding an antigen or epitope present on a protein product of a haploinsufficient gene is capable of interfering with the activity or function of the bound protein product. Such an interference may be, for example, a reduction of activity, inhibition of activity, deviation from normal localization, inhibition or reduction of interaction with other proteins, degradation, partial degradation etc.

The term "small molecule capable of specifically binding to the expressed protein product of a haploinsufficient gene" as used in the context of the present invention refers to a small organic compound that is preferably biologically active, i.e. a biomolecule, but is preferably not a polymer and which binds to the expressed protein product of a haploinsufficient gene. Such an organic compound may have any suitable form or chemical property. The compound is preferably a natural compound, e.g. a secondary metabolites which can be produced and/or modified on the basis of genetic/biochemical pathways present in a cell or which can be provided to a cell. In a preferred embodiment, the small molecule binding to a protein product of a haploinsufficient gene is capable of interfering with the activity or function of the bound protein product. Such an interference may be, for example, a reduction of activity, inhibition of activity, deviation from normal localization, inhibition or reduction of interaction with other proteins, degradation, partial degradation etc. Methods and techniques for the identification and production of small molecules as well as assays for the testing of small molecules are known to the person skilled in the art.

The methodology of the present invention requires that said means for reducing the expression of a haploinsufficient gene in the organism is conveyed by a transgenic locus in the organism itself. Accordingly, any means which specifically degrades or inactivates a haploinsufficient gene transcript as defined herein above, any means which specifically disrupts the haploinsufficient gene DNA sequence and/or any means which interferes with the expressed protein product of a haploinsufficient gene may be provided via a transgenic locus within an organism. For instance, RNA or DNA molecules as described herein may be provided via suitable expression constructs present in said transgenic locus. The expression construct may, for example, comprise control elements allowing to regulate the expression of any of the RNA or DNA species mentioned herein above. The regulation may, for example, be performed via promoter elements operably linked to expression cassettes or expression modules for siRNA, miRNA, antisense RNA or DNA, dsRNA, nucleases, e.g. ZFNs, TALENs, CRISPR or meganucleases, or proteinesous compounds directly or indirectly inhibiting or modulating the activity of the expressed protein product of a haploinsufficient gene, dominant negative variants of expressed protein products of a haploinsufficient gene, aptamers specific for the expressed protein product of a haploinsufficient gene, antibodies or intrabodies against the expressed protein product of a haploinsufficient gene or a small molecule capable of specifically binding to the expressed protein product of a haploinsufficient gene. Such regulation may, for example, be based on promoters, which can be controlled by different parameters such as presence of metabolites or small molecules, pH, temperature, light, presence of growth factors etc. Also envisaged are constitutively active promoters. In case of RNA species to be generated the expression modules may provide suitable linker structures allowing to produce looped or double stranded RNA molecules, binding sites for RNA polymerases, internal binding or cleavage sites etc. In the case of expression constructs for proteins or polypeptides or peptides any suitable element for the enhancement of transcription and/or translation of the coding sequence may be provided, e.g. ribosomal entry sites, transcription factor binding site etc. Antibodies may, for example, be expressed in a single or multiple gene manner. For the provision of small molecules one or more pathway members of synthetic pathways, e.g. heterologous or homologous synthetic pathways, may be expressed.

In further embodiments of the invention, means for reducing the expression of a haploinsufficient gene in the organism may be provided in a two or multi step manner. For example, a transgenic locus may provide an activity leading to the provision of a DNA, RNA, protein or small molecule species. The transgenic locus may additionally provide a further activity, which is capable of modifying said previously generated DNA, RNA, protein or small molecule species. This modification may lead to an increase of its function, a change of its targeting, and an alteration of its interaction capabilities. The expression cassettes may further comprise terminator regions, regions necessary for genomic integration, and/or regions necessary for avoidance of genomic silencing.

The protein encoding sequences may further be adapted in their coding usage to the prevalent codon usage of the organism, species, class, order or family in which they are used. The adaptation of the codon usage may, for example, be a mono-codon usage adaptation, i.e. an adaptation to the usage frequency of single codons among all expressed genes, or among the 10%, 15%, 20%, 30%, 40%, 50% or 60% of most often expressed genes. Alternatively, the adaptation of the codon usage may be a di-codon usage adaptation, i.e. an adaptation to the usage frequency of a combination of two consecutive codons among all expressed genes, or among the 10%, 15%, 20%, 30%, 40%, 50% or 60% of most often expressed genes. Such a di-codon usage may be helpful in avoiding the presence of sequence motifs, which may have a detrimental effect on the transcription of the gene, e.g. cryptic termination or RNA degradation sequences etc.

In further specific embodiments, an activity which leads to the reduction of the expression of a haploinsufficient gene in an organism may be provided as external compound which is to be administered to a cell or organism, but which does not unfold its function before having been activated or modified. The activation or modification may be provided by a means as described herein above, e.g. by a protein or nucleic acid which is expressed via a transgenic locus as defined herein. For example, the reduction of the expression of a haploinsufficient gene in an organism may be initiated by administering to a cell or organism a precursor compound, which is unable to interact with the haploinsufficient gene transcript or expressed protein product, and requires a modification by an activity provided by the transgenic locus, e.g. an enzymatic cleavage step, a enzymatic conversion and the like.

In a second step of the method for reducing the competitive fitness of an organism in hemizygotes according to the invention the reduced expression of a haploinsufficient gene in the organism is rescued. The term "rescuing" as used herein means that an activity is provided which essentially renders a cell or organism at least partially resistant to a suppression of expression of a haploinsufficient gene in hemizygotes as defined herein and a complete rescue in homozygotes. Use of the term rescue includes any instances where the genetic phenomena of transvection contributes to the rescuing of the competitive fitness reducing phenotype in homozygotes.

The provision of such an at least partial resistance or partial rescue to a suppression of expression of a haploinsufficient gene means that a situation is generated, in which the total haploinsufficient gene activity or functionality is not or no longer reduced, or is not or no longer substantially reduced. For example, the activity or functionality of rescue expression situation with respect to a wildtype expression situation may be in a range of about at least about 20% 30% 40%, 45%, 50%, 55%, 60%, 65%, 70%, 75%, 80%, 85%, or 90% or any value in between these value of a wildtype expression situation in at least some haploinsufficient sensitive cells which contribute to the competitive fitness reducing phenotype, i.e. a situation in which wildtype activity or functionality is present if the rescuing is provided by a hemizygous, e.g. heterozygous transgenic locus. The activity or functionality of a rescue expression situation with respect to a wildtype expression situation may be in a range of about at least about 30% 40%, 45%, 50%, 55%, 60%, 65%, 70%, 75%, 80%, 85%, or 90% 91%, 92%, 93%, 94%, 95%, 96%, 97%, 98%, 99%, 99.5% or more or any value in between or any value in between these values of a wildtype expression situation, i.e. a situation in which wildtype activity or functionality is present if the rescuing is provided by a homozygous transgenic locus. The rescue or wildtype expression situation accordingly refers to the expression of all copies of a haploinsufficient gene within an organism including resistant copies which are part of an underdominant construct. This can, for example, be measured in transcript detection assays, enzymatic activity assays, by detecting the presence of structural complexes in a cell or by any other suitable approach.

The copy number of a rescue gene per genome may be one or more. The copy number may vary according to the genetic setup of an organism, the rescue mechanism, the expression properties at the insertion site of the transgenic locus, the ploidy of the organism or the number of paralogous genes in the genome of an organism, or other suitable parameters, in particular the hemizygosity or homozygosity of the organism for a transgenic locus as defined herein. For example, in a diploid organism one transgenic allele as defined herein which may include a single copy of a rescue gene may be present in a hemizygous situation, or in a diploid organism two transgenic loci as defined herein which may include each a single copy of a rescue gene may be present in a homozygous situation. Further envisaged are diploid organisms with more than one rescue gene per transgenic locus.

In a polyploid organism, e.g. a tetraploid organism, a hemizygous setup may include the presence of 1, 2 or 3 transgenic alleles at a locus, while a homozygous setup may include the presence of 4 transgenic alleles at a locus. These transgenic alleles may comprise one or more than one copy of a rescue gene.

In further specific embodiments of the invention a second or further copy of a rescue gene may be present at a second or further position within the genome of an organism. The exact number of copies of the rescue gene in the transgenic locus may preferably be determined empirically, e.g. in dependence of the expression properties of the transgenic locus integration position, the ploidy of the organism, the number of paralogous genes in the genome which are substantially functionally redundant etc.

In certain embodiments, the rescuing may lead to a complete restoration of the wildtype activity or functionality of a haploinsufficient gene whose expression was reduced in an initial step as defined herein above. In further embodiments, the rescuing may lead to a partial restoration of the wildtype activity or functionally of a haploinsufficient gene whose expression was reduced in an initial step as defined herein above, e.g. a restoration of about 20% 30% 40%, 50%, 60%, 70%, 80%, 85%, 90%, 91%, 92%, 93%, 94%, 95%, 96%, 97%, 98%, 99%, 99.5% in at least some haploinsufficient sensitive cells which contribute to the competitive fitness reducing phenotype in hemizygotes, or more or any value in between these value of the wildtype activity or functionally of the haploinsufficient gene whose expression was reduced in an initial step as defined herein above.

The rescuing may be provided, for example, by a modification of the haploinsufficient gene, whose expression was reduced in an initial step as defined herein above, or by the provision of a rescue gene.

The term "rescue gene" as used herein refers to a copy of a haploinsufficient gene which may include flanking regulatory regions and which has been modified to render it resistant to a suppression of expression of a haploinsufficient gene as defined herein. The provision of an at least partial rescue to a suppression of expression of a haploinsufficient gene may preferably be without reducing its functionality, or without substantially reducing its functionality. For example, the functionality of a rescue gene with respect to a wildtype allele may be in a range of about at least 5% 10% 20% 30% 40%, 50%, 60%, 70%, 80%, 90%, 100%,110%, 120%, 130%, 140%, 150%, 160%, 170%, 180%, 190%, or any value in between these value of a wildtype activity or functionality in cells which are haploinsufficient sensitive. In one embodiment where a single non-paralogous haploinsufficient locus, preferably not a gene family of substantially functionally redundant haploinsufficient genes, is targeted in a diploid from a single underdominant locus, it is envisaged that the functionality of the rescue per transgenic allele will not exceed about 200% of the functionality of a wildtype allele at the haploinsufficient locus targeted. It is understood that such an effect ensures a functionality deficit in hemizygotes versus homozygotes, which is at the basis of underdomiance.

In further embodiments, a gene family of substantially functionally redundant haploinsufficient genes may be targeted or the organism may be polyploid. In such situations the functionality of the rescue per transgenic allele may assume any value of relative functionality with respect to all wildtype alleles in the gene family which may be in a range of about at least 5% to 190%, e.g. 5%, 10%, 20%, 30%, 40%, 50%, 60%, 70%, 80%, 90%, 100%, 110%, 120%, 130%, 140%, 150%, 160%, 170%, 180%, 190%, or any value in between these values of a wildtype activity or functionality in cells which are haploinsufficient sensitive. Functionality, may, for example, be measured in enzymatic activity units, presence of structural complexes in a cell or by any other suitable approach.

The copy number of a rescue gene per genome may be one or more per haploid genome and can in some embodiments be located at more than one transgenic locus. The copy number of the rescue gene, which may be a part of the transgenic construct, may vary according to the genetic setup of an organism, the rescue mechanism, the expression properties at the insertion site of the transgenic locus, the ploidy of the organism or the number of paralogous genes in the genome of an organism, or other suitable parameters. For example, in a diploid organism a transgenic locus as defined herein may include a single locus with a variable number of copies of the transgenic locus. In a polyploid organism, e.g. a tetraploid organism, there may be more than one transgenic locus targeting or rescuing the same group of haploinsufficient genes. In further embodiments rescuing activity of a gene may be split across multiple transgenic loci. For example a second or further copy of a rescue gene or rescuing activity may be present at a second or further locus within the genome of an organism. The exact number of copies of the rescue gene or rescuing activity in the transgenic locus may preferably be determined empirically, e.g. in dependence of the expression properties of the transgenic locus integration position, the ploidy of the organism, the number of paralogous genes in the genome which are substantially functionally redundant etc.

The modification of the haploinsufficient gene in order to allow for a rescuing of a reduced expression maybe a modification of the genomic sequence of the haploinsufficient gene. The modification may, for example, be a modification of the primary sequence of a haploinsufficient gene by mutation, which have no phenotypic effect, i.e. lead to the same amino acid sequence. Also envisaged are mutations, which lead to a different amino acid sequence, which provides a similar or equivalent activity or functionality as the original or wildtype amino acid sequence. A reduction of the wildtype activity or functionality per allele by the modification to about 50%, 60%, 70%, 85%, 90%, 95%, 96%, 97%, 98%, or 99% is also envisaged in a very specific embodiment of the present invention. It is preferred to use synonymous mutations, which do not alter the wildtype amino acid sequence. Such mutations may be carried out at all codon, or at a portion of the codons, or at only one, two, 3, 4, 5, 6, 7, 8, 9, 10, 11, 12, 13, 14, 15, 16, 17, 18, 19, 20, 21, 22, 23, 24, 25 or more codons of a haploinsufficient gene. The mutations may be provided at one location within the open reading frame of the haploinsufficient gene, or at 2, 3, 4, 5, 6, 7 or more locations within the open reading frame of the haploinsufficient gene. In further embodiments, the mutations may also be present in non-coding regions of the haploinsufficient gene, e.g. in the 3' untranslated region, in the 5' untranslated region, or both. The mutations may be provided at one location in non-coding regions of the haploinsufficient gene, or at 2, 3, 4, 5, 6, 7 or more locations in the non-coding region(s) of the haploinsufficient gene. Also envisaged is a combination of mutations in both sectors of the haploinsufficient gene.

The modification may further be a synonymous modification according to any possibility of synonymously coded amino acids according to the genetic code of an organism to be used. In further embodiments, the modification may be a synonymous modification, which is based on the preferred codon usage in the organism to be used. The modification of the primary sequence or genomic sequence of the haploinsufficient gene may lead to the avoidance or absence of recognition sites for means which specifically degrade gene transcripts, or which disrupt DNA sequences as defined herein.

For example, the rescuing modification of the haploinsufficient gene as defined herein may lead to the avoidance of binding of antisense, siRNA, miRNA etc. molecules to the transcript of the haploinsufficient gene, thus preventing the degradation of said transcript. Alternatively, the rescuing modification of the haploinsufficient gene as defined herein may lead to the prevention of recognition and/or binding of nucleases such as ZNF, meganuclease, CRISPR or TALEN, thus avoiding the genomic modification of the underlying primary sequence. In a further alternative, the rescuing modification may lead to changed amino acid sequence of the expressed protein product of the haploinsufficient gene, which may no longer be recognized and/or inhibited and/or interfered with by entities such as aptamers, antibodies, intrabodies, small molecules, dominant negative variants etc. as define herein above. For example, epitopes may be modified, functionally non-relevant interaction domains may be modified, functionally non-relevant interfaces may be modified etc.

In specific embodiments, the rescuing activity may be provided by an ortholog or paralog sequence of the haploinsufficient gene, which is functionally equivalent but is sufficiently diverged at the sequence level to be insensitive to suppression. The term "ortholog sequence" as used herein means sequences derived from genes which are present in different species that originated by vertical descent from a single gene of the last common ancestor. The ortholog sequence preferably has the same activity as the wildtype sequence in an organism, or it has an activity which is similar to the wildtype sequence in an organism, and/or which can complement a missing wildtype activity. The ortholog sequence may show modifications at the primary sequence level, i.e. DNA or genomic sequence level, which may render it resistant to any reducing activity as defined herein. Similarly, the ortholog sequence may show modifications at the amino acid level while essentially keeping the wildtype activity of its wildtype homologue, which may render it resistant to any reducing activity as defined herein. The term "paralog sequence" as used herein refers to homologous sequences which were separated by a gene duplication. The paralog sequence preferably has the same activity as the wildtype sequence in an organism, or it has an activity which is similar to the wildtype sequence in an organism, and/or which can complement a missing wildtype activity. The paralog sequence may show modifications at the primary sequence level, i.e. DNA or genomic sequence level, which may render it resistant to any reducing activity as defined herein. Similarly, the paralog sequence may show modifications at the amino acid level while essentially keeping the wildtype activity of its wildtype homologue, which may render it resistant to any reducing activity as defined herein.

The rescue gene or rescuing activity as defined herein may be provided at any suitable location within the organism. The activity may, for example, be provided within a construct, which is genomically integrated in the organism.

It is preferred that the rescue gene or rescuing activity is provided to the organism on an underdominant construct as defined herein. The organism may accordingly have a transgenic locus comprising an underdominant construct comprising at least the rescuing activity or rescue gene and the means for reducing the expression of a haploinsufficient gene in the organism. Further included may be one or more effector genes as defined herein.

In embodiments, in which 2, 3, 4, 5, 6, 7, 8, 9, 10 or more haploinsufficient genes are reduced in their activity or functionality according to the principles mentioned herein, e.g. at the same time or in a timely staggered manner these in their activity or functionality reduced 2, 3, 4, 5, 6, 7, 8, 9, 10 or more haploinsufficient genes may be rescued in an organism as described herein.

In embodiments of the invention in which the reduction of the activity or functionality of one or more haploinsufficient genes is based on the presence of a single transgenic locus as defined herein, a rescuing may also be based on a single transgenic locus, i.e. the same transgenic locus as used for the reduction activity. In alternative embodiments, in which the reduction of the activity or functionality of one or more haploinsufficient genes is based on the presence of more than one transgenic locus, e.g. 2, 3, 4, 5, 6, 7, 8, 9, 10 or more, as defined herein, a rescuing may also be based on more than one transgenic locus, e.g. 2, 3, 4, 5, 6, 7, 8, 9, 10 transgenic loci, e.g. the same number and sequence of transgenic locus as used for the reduction activity, or a different number and sequence of transgenic loci.

In a further embodiment, the reduction of the activity or functionality of one or more haploinsufficient genes may be based on the presence of more than one transgenic locus, e.g. 2, 3, 4, 5, 6, 7, 8, 9, 10 or more transgenic loci as defined herein, and a rescuing may be based on a single transgenic locus, e.g. one of the transgenic loci as used for the reduction activity or a different transgenic locus.

It is preferred that the reduction of the expression of a haploinsufficient gene and the rescuing of the expression of said haploinsufficient gene is conveyed by physically linked transgenic loci. The term "physically linked" as used herein means that reducing and recuing activities are provided in direct proximity within a transgenic locus, e.g. within a distance of about 50 nt, 100 nt, 150 nt, 300 nt, 500 nt, 1000 nt, 5000 nt, or 10000 nt or any value in between these values.

It is particularly preferred that the reduction of the expression of a haploinsufficient gene and the rescuing of the expression of said haploinsufficient gene is conveyed by functionally cross linked transgenic loci. The term "functionally cross-linked" as used herein means that reducing and rescuing activities are provided at different transgenic loci. The functional cross-linkage between transgenic loci may be provided in any suitable form. In a specific embodiment of the present invention said functional linkage may have a form such that linked loci comprise a means for reducing the expression of a haploinsufficient gene of a first haploinsufficient gene, and a rescuing agent able to increase the reduced expression of a second haploinsufficient gene at a first transgenic locus; and a means for reducing the expression of a haploinsufficient gene of a second haploinsufficient gene, and a rescuing agent able to increase the reduced expression of a first haploinsufficient gene at a second transgenic locus. Such a functional cross-linkage of two or more different haploinsufficient genes and corresponding reducing and rescuing activities has the potential to increases the effectiveness of underdominant approaches aimed at biocontainment, population transformation and/or population suppression. It is understood that unlike underdominant constructs which are not functionally cross-linked, it is possible in functionally cross-linked constructs to generate, e.g. through the action of meiotic recombination and chromosomal segregation, unrescued genotypes where the expression of a haploinsufficient is reduced by the action of a transgenic locus and no rescue is provide from any transgenic locus. In a preferred embodiment the phenotype of unrescued genotypes may be embryonic lethality of sterility. This unrescued phenotype may be mechanistically distinct from the hemizygous competitive fitness reducing phenotype detailed herein, while the latter relies on haploinsufficiency, the former does not. In a specific embodiment the haploinsufficient and the unrescued phenotype may work in concert in all generation after the F2 generation of crosses to individuals possessing wildtype alleles at some or all transgenic loci. Further details may be derived from Example 10, whose content or parts of its content is to be regarded as embodiment of the invention. Also envisaged are similar cross provisions of more than two haploinsufficient genes. For example, in transgenic locus 1 a means for reducing haploinsufficient gene 1 and a means for rescuing haploinsufficient gene 3, in transgenic locus 2 a means for reducing haploinsufficient gene 2 and a means for rescuing haploinsufficient gene 1, and in transgenic locus 3 a means for reducing haploinsufficient gene 3 and a means for rescuing haploinsufficient gene 2 or any variation thereof, etc. are provided.

In a further preferred embodiment the reduction of the expression of two or more haploinsufficient genes may be conveyed by one transgenic locus as defined herein, and the rescuing of the expression these two or more haploinsufficient genes may be conveyed by two or more transgenic loci, wherein said transgenic loci are functionally cross-linked.

In a further specific embodiment, the reduction of the expression of a haploinsufficient gene and its rescuing as defined herein may be combined with the use of a mechanistically distinct population transformation system. For example, a mechanistically distinct transformation construct may additionally be introduced into an organism according to the invention. The mechanistically distinct transformation construct may further comprise an effector gene as defined herein.

Examples of mechanistically distinct transformation systems, which are envisaged by the present invention, are the Medea (Maternal-effect dominant embryonic arrest) system as described in Lorenzen et al, 2008, PNAS, 105 (29): 10085-10089, the HEG system as described by Windbichler et. al.. Nature 473, 212-215 (2011). Burt, Proceedings. Biological sciences/The Royal Society 270, 921-8 (2003) or the Wolbachia system as described by Sinkins et al. Nature 7, 427-435 (2006)), or other systems such as the system described by Huang et al., Insect biochemistry and molecular biology 37, 1054-63 (2007), or any other system including a system which may be developed in the future.

The provision of means which reduce the expression of a haploinsufficient gene in the organisms, and of means which rescue the reduced expression within an organism may be carried out accordingly to any suitable method of genetic or molecular introduction. For example, means which reduce the expression of a haploinsufficient gene in the organisms, and means which rescue the reduced expression in the organism may be introduced into a cell or an organism as defined herein as nucleic acid constructs or entities. Suitable introduction methods would be known to the skilled person. The introduction methods may be adapted to the organism or class or organisms in which they are employed and may accordingly vary. For example, such introduction may be carried out by transfection, e.g. DEAE-dextran mediated transfection, electroporation, microinjection, infection with a viral or bacteriophage vector containing the nucleic acid sequences, cell fusion, chromosome-mediated gene transfer, microcell-mediated gene transfer, cationic lipid-mediated transfection, spheroplast fusion, etc. Further introduction technique contemplated by the present invention include the contacting with defective or attenuated retrovirals, microparticle bombardment, the use of coatings with lipids or cell-surface receptors or transfecting agents, the use of encapsulation in liposomes, microparticles, or microcapsules, for instance by administering them in linkage to a peptide which is known to enter the nucleus, or by administering it in linkage to a ligand subject to receptor-mediated endocytosis. Typically, a plasmid vector is introduced in a precipitate, such as a calcium phosphate precipitate, or in a complex with a charged lipid. If the vector is a virus, it may preferably be packaged in vitro using an appropriate packaging cell line and then transduced into host cells. These and numerous further techniques are known in the art for the introduction of nucleic acid molecules or vectors into cells and may be used in accordance with the present invention. Following the introduction of the nucleic acid, engineered cells may be allowed to grow under suitable conditions as known to the person skilled in the art, e.g. for 1-2 days in an enriched media, and then are switched to a selective media. Appropriate culture media and conditions for the above described host cells and vectors are known in the art. A plasmid vector containing the underdominant construct and a visible phenotypic marker can, for example, be microinjected into an early embryo or into a variety of animals. After normal or enhanced care procedures progeny of the injected embryos may be screened for a visible phenotypic marker or for the presence of a suitable genetic marker. These and numerous further techniques are known in the art for the introduction of nucleic acid molecules or vectors into animal genomes and may be used in accordance with the present invention.

The presence of introduced elements may be controlled by numerous standard methods, e.g. gene expression tests, or genomic digestion and hybridization tests, amplification techniques such as PCR etc., which would be known to the person skilled in the art. For instance, the transcription of an introduced nucleic acid may be tested in Northern analysis tests and/or the presence of correspondingly translated polypeptides may be tested via Western analysis tests. Further details and additional tests may be derived from qualified textbooks, e.g. from Ausubel et al., eds, 2007, Current Protocols in Molecular Biology, John Wiley & Sons, Inc., New York.

In one embodiment of the invention an organism according to the invention may be transformed with an underdominant construct as defined herein comprising a sequence leading to the provision of a means which specifically degrades or directly inactivates the haploinsufficient gene transcript or expression product, or which specifically disrupts the haploinsufficient gene DNA sequence; and additionally comprising a modified version of the haploinsufficient gene, which is resistant to a means which specifically degrades or directly inactivates the haploinsufficient gene transcript or expression product, or which specifically disrupts the haploinsufficient gene DNA sequence as defined herein above. The presence of the introduced construct in the targeted organism, e.g. in the genome of the targeted organism, may be tested by genomic digestion and hybridization tests or by site or gene specific amplification techniques. The control of the introduction result may further comprise a control of the number of introduced constructs, e.g. a check whether the construct is present as single or multiple copy and/or whether the construct is present in a hemizygous context (e.g. on only one or a single chromosome) or a homozygous context (e.g. on two or all chromosomes). Suitable organisms comprising the introduced construct in a desired amount and/or at a desired locus may be chose for subsequent uses or method steps.

In a further embodiment an organism according to the invention is initially transformed with an independent transgenic construct comprising a modified version of the haploinsufficient gene, which is resistant to a means which specifically degrades or directly inactivates the haploinsufficient gene transcript or expression product, or which specifically disrupts the haploinsufficient gene DNA sequence as define herein above. The presence of the introduced construct may be tested by genomic digestion and hybridization tests or site or gene specific amplification techniques. The control of the introduction result may further comprise a control of the number of introduced constructs, e.g. a check whether the construct is present as single or multiple copy and/or whether the construct is present in a hemizygous context (e.g. on only one or a single chromosome) or a homozygous context (e.g. on two or all chromosomes). Suitable organisms comprising the introduced construct in a desired amount and/or at a desired locus may be chose for subsequent transformation steps. Such a subsequent transformation step may be a transformation of the organism with an underdominant construct as defined herein, comprising a sequence leading to the provision of a means which specifically degrades or directly inactivates the haploinsufficient gene transcript or expression product, or which specifically disrupts the haploinsufficient gene DNA sequence as defined herein above; and a haploinsufficient gene that comprises the provision of an at least partial rescue to a means which specifically degrades or directly inactivates the haploinsufficient gene transcript or expression product, or which specifically disrupts the haploinsufficient gene DNA sequence as defined herein above. This approach offers the advantage that, for example, once an effective 'rescue' only stock has been established in can be used for all subsequent attempts to place a complete underdominant construct comprising both a rescue gene and a means to reduce the expression of a haploinsufficient gene.

The presence of the second introduced construct may be tested by genomic digestion and hybridization tests or by site or gene specific amplification techniques. The result of this second transformation step may also be controlled, e.g. according to methods as outlined above. The control may further comprise a control of the number of introduced constructs, e.g. a check whether the construct is present as single or multiple copy and/or whether the construct is present in hemizygous context (e.g. on only one or a single chromosome) or a homozygous context (e.g. on two or all chromosomes). Suitable organisms comprising the second introduced construct in a desired amount and/or at a desired locus may be chose for subsequent uses or additional method steps as described herein.

In a further embodiment an organism according to the invention may be co-transformed with an independent transgenic construct comprising a modified version of the haploinsufficient gene, which is resistant to the means by which a given underdominant construct specifically degrades or directly inactivates the haploinsufficient gene transcript or expression product, or which specifically disrupts the haploinsufficient gene DNA sequence, as defined herein above, and with an underdominant construct comprising a sequence leading to the provision of a means which specifically degrades or directly inactivates the haploinsufficient gene transcript or expression product, or which specifically disrupts the haploinsufficient gene DNA sequence; and a haploinsufficient gene that comprises the provision of an at least partial rescue to a means which specifically degrades or directly inactivates the haploinsufficient gene transcript or expression product, or which specifically disrupts the haploinsufficient gene DNA sequence. The co-transformation may be performed by using two different transformation entities such as plasmids or viral vectors etc. Suitable methods for co-transformation of cells or embryos would be known to the skilled person. These methods may preferably correspond to standard protocols, except that a mixture of more plasmid, e.g. two plasmids is used. The presence of the co-transformed constructs in the targeted organism, e.g. in the genome of the targeted organism, may be tested by genomic digestion and hybridization tests or by site or gene specific amplification techniques. The control of the introduction result may further comprise a control of the number of introduced constructs, e.g. a check whether the construct is present as single or multiple copy and/or whether the construct is present in a hemizygous context (e.g. on only one or a single chromosome) or a homozygous context (e.g. on two or all chromosomes). Suitable organisms comprising the co-transformed constructs in a desired amount and/or at a desired locus may be chose for subsequent uses or method steps. This approach offers the advantage that it may be quicker experimental route than first establishing a rescue only stock, which could then be injected.

The transformation or introduction as mentioned above may be carried out in a single organism. In a single organism the transformation or introduction may be carried out in a single cell or multitude of cells, e.g. in specific tissue such as regenerative tissue etc. In a further embodiment, the transformation or introduction as mentioned above may be carried out in a group of organisms, e.g. a population of organisms of a species. Also envisaged is the transformation of organisms of more than one species, e.g. closely related species, or even non-related species. The number of members of a group to be transformed may vary and depend on parameters such as the size of the organism, the use of transformation techniques, the organism's reproduction scheme and time etc. The transformation may further be carried out in such group either once or more than one time, e.g. 2, 3, 4 or 5 times etc. if a first, $2^{nd}$, $3^{rd}$ etc. round of transformation does not yield the desired introduction of an underdominant construct as described herein.

In a preferred embodiment of the invention the transformation or introduction methodology as described herein above may further comprise the step of obtaining an organism which is homozygous for the introduced construct, e.g. the introduced underdominant construct, or for the correspondingly established transgenic locus. Such a step may include a selection for homozygous organism as defined herein, or a separation of homozygous and hemizyogous organisms as defined herein.

In a further embodiment, correspondingly obtained homozygous organisms may further be modified by the removal of the independent transgenic construct as mentioned herein, i.e. a transgenic construct comprising a modified version of the haploinsufficient gene, which is resistant to the means by which a given underdominant construct specifically degrades or directly inactivates the haploinsufficient gene transcript or expression product, or which specifically disrupts the haploinsufficient gene DNA sequence. Such a removal may be accomplished by chromosomal recombination or by segregation. A chromosomal recombination may, for example, be based on the use of site specific recombinases such as Cre or FLP and the presence of cognate recognition sites for Cre or FLP or any other suitable recombinase at the flanks of the independent construct. In further embodiments, the removal may be carried out by segregation, i.e. via repeated rounds of sexual reproduction and selection for absence of the independent construct. This could, for example, be facilitated by suitable visual or genetic markers being present on the distinct loci in question, enabling the simultaneous selection against the rescues only construct in each generation and for underdominant loci.

After having performed a reduction of expression of a haploinsufficient gene in an organism and a rescuing of the reduced expression as described herein, e.g. based on the transformation procedure as defined herein above, an organism or a group of organisms is obtained, which are less competitively fit if hemizygous for the transgenic locus than if homozygous for the transgenic locus. The accordingly obtained organism may be either homozygous for the transgenic locus or be hemizygous for the transgenic locus. The provision of homozygous or hemizygous individuals may be controlled by an adaptation of genetic transformation procedure. For example, a high efficiency transformation of underdominant constructs into an organism may lead to a homozygous genetic situation, or the introduction of two or more alleles of an underdominant construct into the genome at the same location. It is accordingly preferred to use a defined landing site systems, e.g. system based on PhiC31, Cre or FLP recombinases (further details may be derived from Nimmo et al., Insect molecular biology, 15, 129-36 (2006); or from Bischof et al., PNAS, 104, 3312-7 (2007)). This approach may preferably provide direct generation homozygous stocks without the transitory need to generate hemizygotes.

In a preferred embodiment of the present invention, the method as defined herein above, comprising reducing the expression of a haploinsufficient gene in the organism and rescuing the reduced expression, thus yielding an organism which is less competitively fit if hemizygous for the transgenic locus than if homozygous for said locus, may additionally comprise the step of selecting for homozygous organisms. Such a selection step may be carried out on the basis of competitive fitness as defined herein, leading to viability disadvantages and/or the eventual elimination of hemizygous organisms. The selection for completely homozygous stocks may further be facilitated by the use of suitable genetic or visible markers. The detailed property of underdominant constructs to eliminate wildtype alleles at a transgenic locus once the frequency of the underdominant construct exceeds the unstable allelic equilibrium frequency may advantageously be exploited as a method to rapidly and efficiently establish homozygous. Such an approach may, for example, be used as an alternative to the method of selecting families established from single pair crosses or selfing where for two consecutive generations a pattern of inheritance of informative markers is consistent with the founder individual or individuals having been homozygous. Suitable markers in such methods may include the observation of growth differences, or other phenotypic differences which are either indicative for homozygosity or hemizygosity. Further envisaged are molecular detection approaches, which may, for example, be linked to effector genes such as visual markers or color markers etc. The presence of a certain color or its intensity may provide information on the homozygosity and/or hemizygosity of an individual organism. The presence and amount of a transgenic locus and/or its identity may further be determined by molecular analysis, e.g. DNA hybridization techniques, DNA or RNA amplification approaches, e.g. based on polymerase chain reaction, or by determining a phenotypic trait based on optical or visual marker genes or elements, antibiotics resistance genes, herbicide resistance genes included in the transgenic constructs Organisms obtained according to a method as defined herein above, e.g. with or without subsequent homozygous/hemizygous separation step, may be used for subsequent interfertile sexual reproduction within this group of organisms. This may lead to the further provision of homozygous or hemizygous individuals.

For certain applications of the method it may be advantageous to obtain and use organisms which are homozygous for the transgenic locus. Such organisms show a normal or restored competitive fitness in comparison to wildtype organisms and may lead to hemizygous or heterozygous progeny in a next generation if mated with wildtype organisms leading to sexual reproduction. For other applications of the method it may be advantageous to obtain and use organisms which are homozygous or hemizygous for a transgenic locus. The release of hemizygous individuals for the application of population size suppression may preferably be used in situations, where the competitive fitness reducing phenotype is largely confined to reduced fertility.

In a particularly preferred embodiment of the invention an organism obtainable according to a method as defined herein above, in particular obtainable by reducing the expression of a haploinsufficient gene in the organism and rescuing the reduced expression, yielding an organism which is less competitively fit if hemizygous for the transgenic locus than if homozygous for said locus, may be released into a population of the same species. The term "population of the same species" as used herein means a group of otherwise interfertile individuals which are considered to belong to the same taxonomical cluster. The term "otherwise interfertile" as used herein describes groupings of individuals that excepting the effect of any transgenic locus integrated into their genome would be substantially interfertile and capable of producing viable and competitive offspring at appreciable frequencies.

Aiming at a population size suppression a target population or groups of populations may have any size. The number of individuals may be dependent on the number, the sex ratio and/or competitive fitness of the transgenic individuals that can be made available for release. Release ratios of transgenic:wild individuals of more than 1:1, 10:1, 100:1 or 1000:1 or more or any value in between these values may be required for multiple consecutive generations Aiming at a population transformation a target population or groups of populations may in theory have any size. The suitability of target populations may depend on the species, its generation or reproduction time and the rate of migration between target and non-target populations. For example, populations which exhibit an average emigration rate to any non-target populations of about or less than 0.1%, 1%, 2%, 4%, 6%, 8%, 10% or 20% would be most likely to limit the high frequency spread of the underdominant construct to neighboring non-target populations. For example, populations which exhibit an average net immigration rate from wildtype non-target populations of about or less than 0.1%, 1%, 2%, 4%, 6%, 8%, 10% or 20% would be most stable, maintaining the underdominant construct at high frequency in the target populations. To approximately calculate the number of individuals required to be released to achieve population transformation any suitable methodology may be used. It is preferred that equation 1 as mentioned in Example 5 is used. Equation 1 of Example 5 may also be used to calculate the approximate number of wildtype individuals that would be needed to be released in an already transformed population to remove underdominant transgenic constructs. To approximately calculate the geographic stability of population transformation in terms of the capacity to restrict the high frequency presence of the underdominant loci it is preferred to use equations 2 to 12 of Example 5. Alternatively, their derivatives or any other suitable methodology known to the skilled person may be used.

The organism to be released may be hemizygous for the transgenic locus or homozygous for the transgenic locus as defined herein above. Also envisaged is the release of a mixture of homozygous and hemizygous organisms. The release of homozygous organisms is preferred. The release of such organisms may lead to an establishment of the transgenic locus at a high frequency in the population.

The term "establishment of the transgenic locus" as used herein means that the transgenic locus is kept within the population at high equilibrium frequency of transgenic alleles at a transgenic locus of near 100%, or at least 99%, 98%, 97%, 96%, 95%, 85%, 80%, or 75% or any value in between these values. This high frequency equilibrium is intended to persist until population extinction occurs or population transformation is intentionally reversed by the release of sufficient numbers of wildtype individuals over a single or successive generations to exceed the allelic population transformation threshold or if immigration into the transformed population by wildtype individuals is sufficient in a single or successive generations to exceed the allelic population transformation threshold. The loss of population transformation in all these instances implies that the population is returned to its original wildtype state with respects to transgenic loci.

The term "high frequency in the population" as used herein means that the transgenic locus or the genomically inserted underdominant construct is present in the population at near 100%, or at least 99%, 98%, 97%, 96%, 95%, 85%, 80%, or 75% or any value in between these values.

The release of the organisms for the purposes of population transformation may be performed once only, or it may be carried out in phases or stages, covering multiple consecutive generations, e.g. after an initial release a second release may take place after 1 week, 2 weeks, 3 weeks, 4 weeks, 2 months, 3, months, 4 months, 5 months, 6 months, 7 months, 8 months, 9 months, 10 months, 11 months, 12 months, 1.5 years, 2 years etc, or any time point between these time points depending on the generation time of the target organism. The release of the organisms may further be carried out continuously, e.g. every day or every second day for a certain period of time, e.g. for 1 week, 2 weeks, 3 weeks, 4 weeks, 2 months, 3, months, 4 months, 5 months, 6 months, 7 months, 8 months, 9 months, 10 months, 11 months, 12 months etc. The equations given in Example 5 provide some approximations of the unstable allele thresholds which will need to be traversed to achieve population transformation or reversal. During periods of exceptionally high migration or local population extinction and re-colonization it may in some circumstances be desirable to temporarily restart releases.

The release of the organisms may be carried out during one generation of an organism, or during more than one generation, e.g. during 2, 3, 4, 5, 6, 7, 8, 9, 10 or more generations.

The number of released organisms depends on several parameters such as the organism itself, its species, its ecological role and behavior, the reproduction rate, the generation time, the mobility of the organisms, the size of the standing wild population, the geographic spreading of the organisms, the interfertility of the organisms, the climate, the average temperatures, the seasons etc. An adaptation of the release numbers to one or more of these parameters may be carried out by the skilled person. In a preferred embodiment the release may be carried out with sufficient numbers of transgenic individuals to result in a frequency in population of the same species which is greater than the unstable allelic equilibrium frequency predicted by the competitive fitness. The term "unstable allelic equilibrium frequency predicted by the competitive fitness" as used herein means that population allele frequencies starting below this point are expected to decline over time, due to natural selection. Allele frequencies starting above this point are expected to increase over time due to natural selection (further details may be derived from Fisher, 1922, Proc. Roy. Soc. Edinburgh 42:321-341; Wright, 1931, Genetics 16:97-159; Wright, 1941, The American Naturalist 75:513-522; Wiener, 1942, Science 96:407-408; or Li, 1955, Am. Nat. 89:281-295). This critical point is known as 'unstable threshold' allele frequency. The threshold allele frequency for population transformation may be calculated for an isolated population with any suitable methodology, preferably using equation 1 depicted in Example 5. Based on the calculated approximate unstable threshold allele frequency a release strategy can be developed which minimizes the practical resources required to achieve population transformation.

In further embodiments of the invention the method as defined herein above may additionally comprise the step of using an organism obtainable according to a method as defined herein above, in particular obtainable by reducing the expression of a haploinsufficient gene in the organism and rescuing the reduced expression, yielding an organism which is less competitively fit if hemizygous for the transgenic locus than if homozygous for said locus, thus being transgenic, in an environment which comprises otherwise interfertile sexually reproducing wildtype individuals of the organism. This use implies the eventual mating of a transgenic organism with wildtype organisms. It is preferred to use homozygous organisms, e.g. obtained and selected according to the above described methods, for this approach. The mating with wildtype organisms may provide hemizygous progeny, which has a reduced competitive fitness in comparison to the homozygous progeny. The competitive fitness of a hemizygous transgenic organism may accordingly be of a value of about 5%, 10%, 15%, 20%, 25%, 30%, 40%, 50%, 60%, 70%, 80%, or 85% or any value in between these values of a corresponding wildtype organism. In further embodiments, the competitive fitness of a hemizygous transgenic organism may accordingly be of a value of about 5%, 10%, 15%, 20%, 25%, 30%, 40%, 50%, 60%, 70%, 80%, or 85% or any value in between these values of a corresponding homozygous transgenic organism The relative competitive fitness of genotypes can, for example, be inferred from allele frequency changes between generations (see Catteruccia & Godfray Science 299, 2001-2003 (2003)) using an appropriate statistical framework (further details may be derived from Clark et al., Heredity 46, 321-46 (1981) or from FIG. 8 of the application). Alternatively, the relative competitive fitness of genotypes can be estimated by measuring life-history traits in a single generation that are likely to contribute to competitive fitness. Such traits may include, fecundity, variability, weight of individuals, sexual attractiveness, number of gametes generated, growth rates, and/or mobility in a single generation (further details may be derived from Irvin et al., PNAS, 101, 891-6 (2004); or Amenya et al., Insect Molecular Biology, 19, 263-269 (2010)).

In preferred embodiments, the reduced competitive fitness is a reduced viability and/or a reduced fertility of the organism. For example, the viability of a hemizygous transgenic organism may be reduced by a value of about 5%, 10%, 15%, 20%, 25%, 30%, 40%, 50%, 60%, 70%, 80%, or 85% or any value in between these values of a corresponding wildtype organism, or the viability of a hemizygous transgenic organism may be reduced by a value of about 5%, 10%, 15%, 20%, 25%, 30%, 40%, 50%, 60%, 70%, 80%, or 85% or any value in between these values of a corresponding homozygous transgenic organism. The fertility of a hemizygous transgenic organism may be reduced by a value of about 5%, 10%, 15%, 20%, 25%, 30%, 40%, 50%, 60%, 70%, 80%, or 85% or any value in between these values of a corresponding wildtype organism, or the fertility of a hemizygous transgenic organism may be reduced by a value of about 5%, 10%, 15%, 20%, 25%, 30%, 40%, 50%, 60%, 70%, 80%, or 85% or any value in between these values of a corresponding homozygous transgenic organism. In certain embodiments, reductions of viability and fertility may be present at the same time or in the same organism.

The relative fecundity or viability of genotypes can, for example, be estimated using the standard biological techniques as describe in Irvin et al., PNAS, 101, 891-6 (2004); or Amenya et al., Insect Molecular Biology, 19, 263-269 (2010).

In a very specific embodiment the reduction of the competitive fitness in a hemizygous organism may not involve substantial reduction in mean viability. In a further very specific embodiment the reduction of the competitive fitness in a hemizygous organism involve substantial reduction in mean fertility. It is conceivable that competitive fitness may be substantially reduced by depressing sexual attractiveness, e.g. through the disruption of secondary sexual characterizes used in mate choice.

In a specific aspect the present invention relates to a method for the transformation of a population of sexually reproducing organisms, with the proviso that said organism is not a human being, comprising the steps of: (a) reducing the expression of a haploinsufficient gene in the organism, wherein said reduction is conveyed by a transgenic locus in the organism as defined herein above; (b) rescuing the reduced expression in the organism, wherein said rescue is conveyed by the same transgenic locus in the organism as defined herein above, and (c) releasing homozygous organisms obtained in the preceding step into a population of the same species such that the transgenic locus is established at a high frequency in the population. The term "transformation of a population" as used herein refers to a process by which through the deliberate mass release of individuals comprising a transgenic locus to increase the transgenic locus' frequency over the course of subsequent generations in predictable manner until it is stably maintained in the target population at a high frequency, e.g. a frequency of high equilibrium frequency of transgenic alleles at a transgenic locus of near 100%, or at least 99%, 98%, 97%, 96%, 95%, 85%, 80%, or 75% or any value in between these values.

In specific embodiments, the transformation of a population may be achieved by exceeding a threshold frequency of the transgenic locus as described herein in the target population. The threshold frequency may, for example, be greater than 0.5, 0.6, 0.7, 0.8 or 0.9 or more when not combined with other population transformation systems. The homozygous organism to be used may be selected or separated from hemizygous organisms according to method steps as defined herein above. Such method steps may also be included in the method envisaged by the present invention. The transformation of a population may thus result in a population replacement, i.e. a replacement of wildtype organisms by organisms being homozygous or hemizygous for the transgenic locus as described herein. A population transformation may be achieved, for example, by a mass release of individuals carrying the transgenic loci. The term "mass release" as used herein means that at least 40%, 50%, 60%, 70%, 80%, 90%, 100%, 110%, 200%, 300%, 1000% or more or any value in between these values of the current number of wildtype individuals of a given population are released. This mass release may be performed once, or more than one time, e.g. 2, 3, 4, 5, 6, 7 or more times. The release may be carried out during one generation or during multiple generations and may be set up during phases or time frames as defined herein above. The releases may be of a single sex, preferably male only, or constitute a mixture of both sexes in various proportions.

Based on this principle the present invention also provides in a further aspect a method for reducing the size of a wild population of otherwise interfertile sexually reproducing organisms, with the proviso that said organism is not a human being, comprising the steps of: (a) reducing the expression of a haploinsufficient gene in the organism, wherein said reduction is conveyed by a transgenic locus in the organism; (b) rescuing the reduced expression in the organism, wherein said rescue is conveyed by the same transgenic locus in the organism, and (c) using a hemizygous transgenic organism obtained in step (b) or a mixture of homozygous and hemizygous transgenic organisms obtained in step (b) in an environment comprising otherwise interfertile sexually reproducing wildtype individuals of the organism, wherein the competitive fitness of hemizygous progeny is reduced. Releases may be of a single sex, preferably male only, or constitute a mixture of both sexes in various proportions. The term "wild population" as used herein means that the individuals encompassed in said population do not comprise or contain a transgenic locus or underdominant construct as defined herein. Such individuals are considered as wildtype individuals or wildtype organisms.

A "reduction of the size" of such wild populations as used herein refers to a relative reduction of the number of members of a certain genotype, e.g. a genotype of not comprising a transgenic locus as defined herein, while the overall number of individuals of a species comprising transgenic and non-transgenic genotypes may not be altered or be increased. Also possible is a reduction of the overall number of individuals of a species comprising transgenic and non-transgenic genotypes, which is however smaller or less pronounced than the reduction of the wildtype individuals. The reduction of the wild population according to this aspect of the invention may be a reduction by 5%, 10%, 15%, 20%, 25%, 30%, 35%, 40%, 45%, 50%, 60%, 70%, 80%, 90%, 99% or more or any value in between these values in comparison to the number of wildtype individuals before the performance of the method, or in comparison to a wild population which was not treated or into which no transgenic individuals were released. In certain cases the degree of suppression may be 100% resulting in local extinction of the target population. The releases may be of a single sex, preferably male only, or constitute a mixture of both sexes in various proportions.

In a particular embodiment of the population suppression aspect of the invention, homozygous and/or hemizygous transgenic individuals may be released into areas with no known interfertile wildtype population. It is preferred to perform such a step as part of a preventative release program to reduce the potential of wild populations to establish themselves in a risk or sensitive area.

The reduction of a wild population of individuals may be based in one embodiment on a decrease of sexual reproduction of individuals hemizygous for the transgenic locus as defined herein. The decrease of sexual reproduction may be due to a reduction of general fitness, e.g. due to the partial rescue of a haploinsufficient gene as defined herein above The organism to be used in this method is either a hemizygous transgenic organism or a mixture of a homozygous and a hemizygous transgenic organisms. The release of hemizygous individuals for the application of population size suppression is particularly envisaged, where the competitive fitness reducing phenotype is largely confined to reduced fertility. It is preferred to release homozygote transgenic organisms.

In further embodiments, the frequency of the transgenic locus in a method for transformation of a population or a method for reducing the size of a wild population may increase during the release and/or after the release of individual organisms as defined herein.

In a further specific aspect the present invention relates to a method for decreasing the introgression of a transgenic locus in an organism into a population of otherwise interfertile sexually reproducing organisms, with the proviso that said organism is not a human being, comprising the steps of: (a) reducing the expression of a haploinsufficient gene in the organism, wherein said reduction is conveyed by a transgenic locus in the organism; (b) rescuing the reduced expression in the organism, wherein said rescue is conveyed by the same transgenic locus in the organism, and (c) using a transgenic organism obtained in step (b) in an environment comprising otherwise interfertile sexually reproducing wildtype individuals of the organism, wherein the competitive fitness of hemizygous progeny is reduced, thereby decreasing the rate of sexually reproduction and/or viability of hemizygous progeny. The term "decreasing the introgression of a transgenic locus into a population of otherwise interfertile sexually reproducing organisms" as used herein means that the frequency of a transgenic locus in a population of otherwise interfertile sexually reproducing organisms is brought below a level which would be expected for a neutral trait a selectively advantageous or selectively deleterious trait or a trait which does not have influence on the competitive fitness of the organism in the environment. The decrease of introgression is advantageously achieved by the fact that the transgenic locus leads to a reduction of the competitive fitness if present in a hemizygous manner in an organism. For diploid organisms the transgenic locus would lead to a reduction of the competitive fitness if present in a heterozygous manner, i.e. as only one copy or allele.

The use of the organism may include the planting of homozygous transgenic underdominant individuals in buffer zones, e.g. around outcrossing plants, to limit the spread of the individuals across the buffer, while at the same time limiting the potential for introgression in subsequent generations due to the reduced competitive fitness of hemizygotes in the next generations. This application is of particular use in containing the unintentional outcrossing of genetically modified plants.

The reduction of the competitive fitness of hemizygous progeny may be, for example, a reduction of about 50%, 60%, 70%, 80%, 85%, 90%, 95% or, preferably 100%, or any value in between these values of the competitive fitness of a corresponding wildtype organism or of a corresponding homozygous transgenic organism. In preferred embodiments, the reduced competitive fitness is a reduced viability and/or a reduced fertility of the organism. For example, the viability of a hemizygous transgenic organism may be reduced by a value of about 50%, 60%, 70%, 80%, 85%, 90%, 95% or, preferably 100%, or any value in between these values of a corresponding wildtype organism or of a corresponding homozygous transgenic organism. The fertility of a hemizygous organism may be reduced by a value of about 50%, 60%, 70%, 80%, 85%, 90%, 95% or 100%, or any value in between these values of a corresponding wildtype organism or of a corresponding homozygous transgenic organism. The reduced competitive fitness in the context of a method for decreasing the introgression of a transgenic locus into a population of otherwise interfertile sexually reproducing organisms may also be or result in a complete non-viability of progeny, and/or complete non-fertility of progeny. This may be observed at any suitable growth phase. In case of non-viability the absence of progeny may be detectable. In the case of infertility the fertilized zygotes may be scored.

In a preferred embodiment of the present invention the decrease of introgression of a transgenic locus in an organism is a prevention of introgression of a transgenic locus into population of otherwise interfertile sexually reproducing wildtype individuals of the organism. The reduction of competitive fitness in this embodiment may accordingly eliminate the viability of progeny.

In an alternative, preferred embodiment, the possibility of sexual reproduction of hemizygous progeny may be eliminated. Hemizygous progeny may, for example, show normal or healthy growth or environment survival behavior, but may be unable to reproduce within its population or with any other population of wildtype or homozygous or hemizygous individual of its species, or with other species. This behavior may, for example, be due to a reduction in the ability of hemizygous plants to generate viable pollen or ovules or support seed development.

Haploinsufficient mutations of CRP genes in plants may, for example, result in the reduction of the viability of pollen and ovules, e.g. by 70% and 50% respectively, in addition to reduced seed production (further details may be derived from Weijers et al., Cell 4299, 4289-4299 (2001); or Degenhardt, Plant physiology, 147, 128-42 (2008)).

In a further aspect the present invention relates to a genetic system which comprises (a) a means for specifically reducing the expression of a haploinsufficient gene as defined herein above; and (b) a rescuing agent able to increase the reduced expression of said haploinsufficient gene as defined herein above. The term "specifically reducing" as used herein refers to a targeted, non-random approach towards a haploinisufficiency gene. The term excludes approaches for the reduction of expression which are based on random modifications such as random mutagenesis or insertional approaches, which, for example, by chance happen to hit a haploinsufficiency gene. Such approaches are considered to be non-specific and therefore cannot be subsumed under the term used. In particular, random mutagenesis or insertional approaches tend to modify genomic sequences not only at one position, but often at several positions leading to unforeseeable genetic implications which cannot be expected to be specifically rescued by the expression of a specific rescue gene or specific rescue genes. The genetic system may, for example, be provided as single transformation entity, i.e. as entity which can be introduced as single molecule into a target organism. Also envisaged is the provision of the genetic system as multiple transformation entity, i.e. as entity, which can be introduced into a target organism by 2, 3 or more different molecules. The molecules may be any suitable introduction vehicle such as a mobile genetic element, plasmid DNA, viral vector, or genomic insertion cassette or exogenous DNA capable of genomic integration. The vehicle may be circular or linear, e.g. have been linearized by cutting with a restriction enzyme or been sheared by physical forces. A mobile genetic element may be, for example, a transposable element, which is capable of insertion at an arbitrary or predefined location within the genome of an organism. This transposable element may comprise one or more an underdominant constructs as defined herein. Examples of suitable transposable elements include DNA transposons such as sleeping beauty or derivatives thereof, Ac/Ds or derivatives thereof, P elements or derivatives thereof, mariner elements or derivatives thereof, Tc1 or Tc3 or derivatives thereof, piggyback elements, Minos elements or retrotransposons such as Ty1 or derivatives thereof. In addition various defined landing site systems based on PhiC31, Cre or FLP recombinases may be used with suitable plasmids to integrate them at defined positions in the genome (further details may be derived from Nimmo et al., Insect molecular biology, 15, 129-36 (2006); or Bischof et al., PNAS, 104, 3312-7 (2007)).

In a further aspect, the present invention relates to the use of a genetic system as described above for the population transformation of an organism according to the present invention. The population transformation may essentially be carried out as outlined in the context of the introduction of underdominant constructs into an organism herein above. It is particularly preferred that the transformation be carried out in a multitude of organisms or a population of organisms. This multitude of organisms or population of organisms is preferably of the same species.

In a further preferred embodiment, the genetic system according to the invention may be used for establishing a means for reducing the expression of a haploinsufficient gene in organism and for establishing a rescuing agent able to increase the reduced expression of the haploinsufficient gene in an organism. The genetic system may preferably be used to establish the reducing and rescuing activities in a homozygous form in an organism. Corresponding obtained organism may further lead to an establishment of the genetic system at a high frequency in a population of an organism.

It is further preferred that the genetic system according to the invention may be used for decreasing its own introgression into a population of otherwise interfertile sexually reproducing organisms. The genetic system may accordingly be provided in an organism, which is otherwise interfertile and sexually reproducing with other organisms of the same species. The genetic system may preferably be provided in a homozygous form in an organism. Based on the reduced competitive fitness of hemizygous progeny of an organism comprising a genetic system as defined herein, an introgression of the genetic system into a population of not transformed individuals may be achieve. For example, wildtype organisms which mate with organisms comprising a genetic system as defined herein may have a reduced competitive fitness, e.g. be non-viable and/or non-fertile or have reduced viability and/or a reduced fertility. Such organisms may not contribute to a dissemination of the genetic system to further progeny and thus an introgression of the genetic system into the wild population. In a specific embodiment, the genetic system as defined herein may be used for the prevention of introgression of the genetic system itself into a population of wildtype organisms by an elimination or limitation of the sexual reproduction of hemizygous progeny. Such elimination or limitation may be based on effects due to one or more haploinsufficient genes or due to effects based on one or more effector genes, which may be provided together with the genetic system as described herein above.

In yet another aspect the present invention relates to a genetically modified organism, which comprises (a) a means for specifically reducing the expression of a haploinsufficient gene as defined herein above; and (b) a rescuing agent able to increase the reduced expression said haploinsufficient gene as defined herein above. The term "specifically reducing" as used in this context is to be understood as defined herein above. In specific embodiment, the genetically modified organism is not a human being. In a further specific embodiment, the genetically modified organisms may be obtained or is obtainable by carrying out the method for reducing the competitive fitness of an organism as defined herein. The genetically modified organism according to the invention may be homozygous for one or more underdominant constructs as defined herein. In a further embodiment, the genetically modified organism may be hemizygous for one or more underdominant constructs as defined herein. In yet another preferred embodiment, the genetically modified organism being hemizygous for one or more underdominant constructs as defined herein, may have a reduced competitive fitness compared to the organism homozygous for an underdominant construct according to the invention.

An organism as mentioned herein above, e.g. an organism with which the methods according to the invention are carried out, or a genetically modified organism encompassed by the present invention may be any suitable organism known to the skilled person. Examples of such organisms include animals, plants, fungi or protists. Among the animals disease vectoring animals, disease causing animals and livestock animals are preferred. The term "disease vectoring animal" as used herein refers to any animal, which transmits a disease from one host to another. Such a disease may be an animal, e.g. human disease or a plant disease. Examples of such animals are an insect, an arachnid, or a rodent. Among the insects a mosquito or a fly is preferred. Particularly preferred are plant disease vectoring insects, e.g. Acyrthosiphon pisum, *Agromyzidae* Sp., *Anthomyiidae* Sp., Beet leafhopper, Brevicoryne brassicae, Cacopsylla melanoneura, Common brown leafhopper, Culmicole, CurculionidaeE, Eumetopina flavipes, Frankliniella occidentalis, Frankliniella triticiG, Glassy-winged sharpshooter, Jumping plant louse, Leaf beetle, Leafhopper, Mealybug, Melon fly, Molytinae, Pegomya hyoscyami, Pissodes, Pissodes strobi, Pissodini, Planthopper, Pseudococcus viburni, Psylla pyri, Rhabdophaga rosaria, Rhynchophorus palmarum, Scaphoideus titanus, Scirtothrips dorsalis, Silverleaf whitefly, Tephritidae, Thripidae, Thrips palmi, Tomicus piniperda, Toxoptera citricida, Treehopper, Triozidae. Also envisaged are animal disease vectoring insects, e.g. *Aedes* sp., *Anopheles* sp., *Calliphoridae* sp., *Culex* Sp., *Glossinidae* sp., *Haemagogus* sp., *Hippelates* sp., *Ixodoidea* sp., *Phlebotomus* sp., *Rhodnius* sp., *Simuliinae* sp., *Simuliini* sp., *Simulium* sp., or *Triatoma* sp.

A preferred arachnid is a tick. The rodent may be a rat or a mouse. In a further embodiment, the disease causing animal may be a human disease causing nematode, an animal disease causing nematode or a plant disease causing nematode. Examples of such nematodes include *Ancylostoma* sp., *Aphelenchoides* sp., *Ascari* sp., *Bursaphelenchus* sp., *Ditylenchus* sp., *Enterobius* sp., *Globodera* sp., *Heterodera* sp., *Longidorus* sp., *Meloidogyne* sp., *Nacobbus* sp., *Pratylenchus* sp., *Toxocara* sp., *Trichodorus* sp., *Trichuris* sp., *Tylenchulus* sp., and *Xiphinema* sp.

In a further particularly preferred embodiment said organism is an agricultural plant. An agricultural plant may be any plant, which is used by humans for agricultural purposes. Examples include a staple crop, e.g. a grain crop, root crops, tubers, pulses, or legumes; or a sugar producing crop, or an oil producing plant, e.g. oil palm, or safflower. Particularly preferred examples of agricultural plants are Alfalfa, Anthurium, Apple, Aspen, Bacterium, Bahiagrass, Banana, Barley, Beet, Belladonna, Bermudagrass, Blueberry, Camelina, Carrot, Cassava, Chicory, Chrysanthemum, Clavibacter, Corn, Cotton, Crambe, Cranberry, Cucumber, Eggplant, Falseflax, Gladiolus, Grape, Grapefruit, Grapevine, Guayule, Lettuce, Melon, Miscanthus, Onion, Papaya, Pea, Peanut, Pelargonium, Pepper, Peppermint, Persimmon, Petunia, Plum, Poplar, Potato, Pseudomonas, Rapeseed, Rhizobium, Rice, Safflower, Sorghum, Soybean, Squash, Strawberry, Sugarbeet, Sugarcane, Sunflower, Sweetgum, Switchgrass, Tobacco, Tomato, Walnut, Watermelon, or Wheat.

In a further embodiment the plant may be a pest plant. The term "pest plant" as used herein refers to a plant which is considered to disturbed agricultural or horticultural endeavours of the human being. Envisaged examples or pest plants include *Acmena smithii, Ailanthus altissima, Akebia quinata, Alternanthera philoxeroides, Anredera cordifolia, Araujia sericifera, Aristea ecklonii, Arundo donax, Asparagus asparagoides, Asparagus densiflorus, Asparagus scandens, Berberis darwinii, Bomarea multiflora, Bryonia cretica, Calluna vulgaris, Cardiospermum grandiflorum, Cardiospermum halicacabum, Carpobrotus edulis, Celastrus orbiculatus, Ceratophyllum demersum, Cestrum parqui, Chrysanthemoides monilifera, Clematis flammula, Clematis vitalba, Cobaea scandens, Cortaderia jubata, Cortaderia selloana, Cotoneaster simonsii, Cotyledon orbiculata, Crassula multicava, Cyathea cooperi, Dipogon lignosus, Drosera capensis, Eccremocarpus scaber, Egeria densa, Ehrharta villosa, Eichhornia crassipes, Eomecon chionantha, Equisetum, Eragrostis curvula, Erigeron karvinskianus, Euonymus japonicas, Ficus rubiginosa, Fuchsia boliviana, Galeobdolon luteum, Gunnera tinctoria, Gymnocoronis spilanthoides, Hedychium flavescens, Hedychium gardnerianum, Heracleum mantegazzianum, Hieracium, Homalanthus populifoliusm, Homeria collina, Houttuynia cordata, Hydrilla verticillata, Hydrocleys nymphoides, Hypericum androsaemum, Ipomoea indica, Iris pseudacorus, Jasminum humile, Lagarosiphon major, Lantana camara, Ligustrum lucidum, Lilium formosanum, Lonicera japonica, Ludwigia peploides* subsp. *Montevidensis, Lythrum salicaria, Macfadyena unguis-cati, Menyanthes trifoliate, Myoporum insulare, Myrica faya, Myricaria germanica, Myriophyllum aquaticum, Nassella, Nephrolepis cordifolia, Nuphar lutea, Nymphaea Mexicana, Nymphoides geminate, Nymphoides peltata, Ochna serrulata, Osmunda regalis, Panicum maximum, Passiflora caerulea, Passiflora tarminiana, Passiflora tripartite, Pennisetum, Phragmites australis, Pinus contorta, Pistia stratiotes, Pittosporum undulatum, Plectranthus ciliates, Polygala myrtifolia, Potamogeton perfoliatus, Prunus serotina, Pyracantha angustifolia, Reynoutria japonica, Reynoutria sachalinensis, Rhamnus alaternus, Rhododendron ponticum, Sagittaria montevidensis, Sagittaria platyphylla, Sagittaria sagittifolia, Salix cinerea, Salix fragilis, Salvinia molesta, Schinus terebinthifolius, Schoenoplectus californicus, Selaginella kraussiana, Solanum* marginatum, *Solanum mauritianum, Tradescantia fluminensis, Tropaeolum speciosum, Tussilago farfara, Typha latifolia, Utricularia arenaria, Utricularia gibba, Utricularia livida, Utricularia sandersonii, Vallisneria gigantean, Vallisneria spiralis, Zantedeschia* and *Zizania latifolia.*

In a further preferred embodiment, the plant is an algae. Envisaged examples of algae within the context of the present invention are *Macrocystis*. Particularly preferred are algae for biofuel production such as *Botryococcus braunii, Gracilaria, Pleurochrysis carterae, Sargassum, Ankistrodesmus, Botryococcus braunii, Chlorella protothecoides, Cyclotella, Dunaliella tertiolecta, Hantzschia, Nannochloris, Nannochloropsis, Nitzschia, Phaeodactylum tricornutum, Scenedesmus, Stichococcus, Tetraselmis suecica, Thalassiosira pseudonana, Crypthecodinium cohnii, Neochloris oleoabundans*, and *Schiochytrium.*

In a further preferred embodiment the organism is a fungus, e.g. a toxic fungus or a fungus used in a bioreactor production. Examples of fungi to be used within the context of the present invention are derived from the genus *Saccharomyces* or *Aspergillus*.

The following examples and figures are provided for illustrative purposes. It is thus understood that the examples and figures are not to be construed as limiting. The skilled person in the art will clearly be able to envisage further modifications of the principles laid out herein.

EXAMPLES

Example 1

The endogenous haploinsufficient gene targeted in the construct described is RpL14 (cytogenetic location 66D8), which is a cytoplasmic ribosomal protein (CRP). Heterozygous mutations in RpL14 result in a classic strong Minute phenotype with delayed development, slender scutellar bristles and reduced female fertility (Sæbøe-Larssen et al., 1997 Molecular and General Genetics 255:141-151). The knock-down (RpL14.dsRNA) is a dsRNA inverted repeat, targeting RNAi to 67 bp of the endogenous RpL14 wildtype mRNA (RpL14+). The rescue (RpL14$^r$) is a complete copy of the wildtype RpL14 gene (including its promoter and flanking regions) where 14 synonymous mutations had been introduced within the 67 bp region targeted for RNAi by RpL14.dsRNA (described in further detail below). The number and position of synonymous changes ensures that all of the approximately 21 bp siRNA fragments predicted to be produced by Dicer proteins for RNAi targeting incorporated a minimum of 3 mismatches. A genetic transformation plasmid combining both genes (see FIG. 1) was integrated at an RFP marked attP/ϕC31 landing site on chromosome three (cytogenetic location 86Fb; Bischof, 2007, PNAS, 104:3312-7), resulting in the genotype M{3x-P3-RFP, {attR, w$^{+mc}$, RpL14$^r$, UAS-RpL14.dsRNA}}86Fb referred to as {Ud}86 (the 86 suffix denotes the genomic location of the insert). To drive constitutive expression of the UAS-RNAi knock-down, a second chromosome Actin5c-GAL4 driver was selected, P{w$^{+mc}$=Act5C-GAL4}25FO1.

Development of the dsRNAi.RpL14 Knock-Down of RpL14+

The RpL14 gene (FBgn0017579 or CG6253) was selected as a representative CRP gene, which had previously been described as exhibiting a strong Minute phenotype (Sæbøe-Larssen et al., 1997, Molecular and General Genetics 255:141-151). It was the first gene selected for development of this approach.

To identify an approximately 70 bp region of RpL14 to target by RNAi knock-down the following four criterion to the wildtype mRNA sequence were applied: (1) No predicted off-target effects (default setting with 'Off-Target Size' set to 16 bp, flyrnai.org/cgi-bin/RNAi_find_primers.pl), (2) No regions with a high number of non-degenerate codons ATG or TGG, (3) target must be present in all alternative splicing variants, and (4) region exhibits a high degree of structural accessibility (according to default settings of S-Fold, sfold.wadsworth.org/cgi-bin/sirna.pl). When these criteria were applied it was not possible to target a single contiguous region, so two non-contiguous regions were selected (called blocks A and B); both blocks happened to be in exon 2. The sequence of RpL14.dsRNA is shown in FIG. 3. Block A is 41 bp (targeting to 3L:8594414 . . . 8594454 of RpL14+) and block B is 31 bp long (targeting to 3L:8594485 . . . 8594515 of RpL14+). A short KpnI containing linker was inserted between the block A and B after checking that the linker did not cause any predicted off-target effects.

An inverted repeat of the targeting sequence was assembled and cloned into the pUASattB plasmid (Genbank: EF362409; Bischof, 2007, PNAS 104:3312-7) at the multiple cloning site, downstream of the UAS promoter. SURE 2 supercompetent *E. coli* cells (Agilent Techologies) were used for bacterial transformation to ensure the stability of the short hairpin structure. The effectiveness of RpL14.dsRNA in targeting RpL14+ was experimentally demonstrated using flies transformed with {UAS-RpL14.dsRNA} crossed to GAL4 drivers: (w*; P{w$^{+mc}$=GAL4-ninaE.GMR}12 resulted in necrotic eye spots, y$^1$ w* P{w$^{+mc}$=GAL4-Act5C(FRT.CD2).P}D resulted in lethality, and w*; P{w$^{+mc}$=GAL4-ey.H}3-8 resulted in uneclosed headless adults (see Enerly et al., 2003, Gene 320:41-48).

Development of the Rescue RpL14$^r$

The RpL14 region was amplified using Phusion Taq (Finnzyme) from DNA prepared from the genome reference stock (Bloomington Stock: 2057, y[1]; Gr22b[1] Gr22d[1] cn[1] CG33964[R4.2] bw[1] sp[1]; LysC[1] MstProx[1] GstD5[1] Rh6[1]). This was done using the following primers NotI-5'-TATGCGGCCGCttgattagtttcctggccactt (SEQ ID NO: 3) and EcoRI-5'-TATGAATTCaaggcataagagctttgaatcg (SEQ ID NO: 4). This resulted in amplification of 3L: 8593592 . . . 8596494. To maximize the likelihood that regulatory regions of RpL14 were incorporated, fragments of the flanking genes were also included in the PCR product (FIG. 1). The endogenous RpL14 fragment was cloned into the HindIII site immediately upstream of the UAS promoter in the pUASattB plasmid already containing the UAS-RpL14.dsRNA sequence described above (see FIG. 4). The full plasmid DNA sequence is given in the attached genbank formatted file.

The 14 synonymous mutations that conferred insensitivity of RpL14$^r$ to RNAi targeting were introduced into exon 2 by synthesizing a new sequence (DNA2.0, Inc., dna20.com/). This was then ligated into the plasmid in the place of the corresponding wildtype sequence, using standard cloning techniques. The 14 synonymous mutations were distributed to ensure that every 21 bp includes at least 3 synonymous mismatches with the RpL14$^r$ mRNA. As far as possible the introduced mutations preserved the same balance between *D. melanogaster* preferred and un-preferred codons.

Germline transformants of *D. melanogaster* were generated by inserting the {Ud} plasmid (see FIG. 4) into the 86Fb (3R:7634329) landing site by BestGene, Inc. (thebestgene.com/) using the attP/$\phi$C31 integration system (Bischof, 2007, PNAS, 104:3312-7).

The insensitivity of RpL14' to RNAi targeting was demonstrated by its ability to rescue the lethality of UAS-RpL14.dsRNA in the presence of GAL4-Act5C expression. This construct was then used in all subsequent experiments. The expression of the rescue gene was confirmed in adults using allele-specific RT-qPCR (see Example 2) both in the presence and absence of GAL4 (see FIG. 5 and FIG. 6, respectively).

Generation of Outbred Transgenic Stocks

Two red-eyed stocks were generated for subsequent experiments to survey for strong underdominance: w*; {Act5C-GAL4}/CyO; {Ud}86/{Ud}86 and w*; {Act5C-GAL4}/CyO: +/+. *Drosophila* lines that are highly homozygous and maintained in the laboratory for several generations can have dramatically lowered fitness and quickly accumulate additional deleterious mutations throughout the genome (Seager et al., 1982, Genetics 102:485-502; Wallace, 1956, J. Genetics 54:280-293). To ensure a robust test of underdominance, both stocks were initially out crossed for 3 generations to a mixed stock composed of globally derived lines.

Heterozygous {Ud} transformants ($y^1$ w*; M{3x-P3-RFP, {attR, $w^{+mc}$, RpL14$^r$, UAS-RpL14.dsRNA}}86Fb/+) were outcrossed to mixed assortment of the following wild derived stocks which were made white eyed, $w^{1118}$, by establishing them from w $F_2$ offspring from a female parent backcross, the wildtype lines are Bloomington stock 3848, CO3 (NY, USA); Bloomington stock 3885, Wild 5A (GA, USA); Aquadro lab, B96 (Beijing, China), and 9 isofemale lines established in 2009 (from Plon and Kiel, Germany). The transformed $w^{+mc}$ individuals were left at <0.3 frequency (to maximize recombination with wildtype chromosomes) for >3 generations to recombine en masse. After the $4^{th}$ generation $y^+$, RFP, $w^{+mc}$ individuals were selected for the crosses outlined in the following scheme:

Crosses were done reciprocally with as many individuals as possible (>10) to maximize natural variation in the final stocks. Crosses 1 and 2 are done in parallel and the offspring are used to initiate cross 3.

Cross 1
  w[*]; T(2;3)ap[Xa], ap[Xa]/CyO; TM3, Sb[1] (Bloomington 2475)
  X
  w[*]; +; M{3x-P3-RFP, w[+mC], {Ud}}86/+(out crossed {Ud}86 heterozygotes)
  Select ap$^+$, w$^+$, RFP, Cy$^-$, Sb$^-$ progeny yielding
  w[*]; +/CyO; M{3x-P3-RFP, w[+mC], {Ud}}86/TM3, Sb[1]

Cross 2
  y[1] w[*]; P{w[+mC]=Act5C-GAL4}25FO1/CyO, y[+] (Bloomington 4414)
  X
  w[*]; T(2;3)ap[Xa], ap[Xa]/CyO; TM3, Sb[1] (Bloomington 2475)
  Select y$^+$, ap$^+$, w$^+$, RFP, Cy$^-$, Sb$^-$ progeny yielding
  w[*]; T(2;3)ap[Xa], ap[Xa]/P{w[+mC]=Act5C-GAL4}25FO1; +/TM3, Sb[1]

Cross 3
  w[*]; +/CyO; M{3x-P3-RFP, w[+mC], {Ud}}86/TM3, Sb[1] (cross 1 progeny)
  X
  w[*]; T(2;3)ap[Xa], ap[Xa]/P{w[+mC]=Act5C-GAL4}25FO1; +/TM3, Sb[1] (cross 2 progeny)
  Select Cy$^-$, RFP, progeny yielding
  w[*]; P{w[+mC]=Act5C-GAL4}25FO1/CyO; M{3x-P3-RFP, w[+mC], {Ud}}86/TM3, Sb[1]
  and
  w[*]; P{w[+mC]=Act5C-GAL4}25FO1/CyO; M{3x-P3-RFP, w[+mC], {Ud}}86/+

This last cross yields two types of third chromosome heterozygotes. {Ud}86 with the TM3 balancer and {Ud}86 with a wildtype chromosome. In the following generations Sb$^-$ is selected against to remove the balancer. Third chromosome +/+ wildtype homozygotes and {Ud}/{Ud} homozygotes are selected (by selecting for and against RFP) to initiate the following experiments.

The full resulting genotypes are
w[*]; P{w[+mC]=Act5C-GAL4}25FO1/CyO; M{3x-P3-RFP, w[+mC], {Ud}}86
and
w[*]; P{w[+mC]=Act5C-GAL4}25FO1/CyO; +

As the genotypes differ only on the third chromosomes, only the third chromosomes genotype is indicated elsewhere in the text. Note that the driving promoter, act5c, could be used to directly drive the RNAi and generate underdominance in a single cassette (act5c-RpL14.dsRNA, RpL14$^r$), but we used the binary GAL4/UAS system here in order to have the flexibility to test the effects of different expression patterns.

Fly Rearing

In this and in following examples, all flies were maintained on standard media (flystocks.bio.indiana.edu/FlyWork/media-recipes/bloomfood.htm) in an incubator at 24° C. under a 14:10 hour light/dark cycle. Either 50 mL vials or 300 mL bottles, as specified below, containing food were used. When flies were added to a new container, yeast was added to the food surface to stimulate egg laying. When adults were cleared from a bottle two Kimwipes™ were added to reduce emerging adult death rates (from getting stuck in liquefied food).

Epi-Fluorescent Genotyping of Flies

In this and in following examples, genotyping of flies was done by surveying for the RFP fluorescence of the 3x-P3-RFP gene at the {Ud}86 landing site. Scoring of fluorescence was done on a Leica MZ10 F epi-fluorescent microscope with a Leica EL 6000 light source in a darkened room. Flies were lightly anesthetized using $CO_2$. All flies had red eyes, w$^+$. RFP scoring in the eye was unreliable due to quenching; however, using the ocelli +/+ flies could reliably be distinguished from +/{Ud}86 or {Ud}86/{Ud}86 flies. For RFP scoring a Leica-dsRED filter set was used (excitation 545/30 nm, emission 620/60 nm). For experiments requiring the identification of all three genotypes 3x-P3-GFP expression could be co-dominantly scored along with RFP by the additional use of a Leica-GFP2 filter set (excitation 480/40 nm, emission 510 nm).

Example 2

Determining Gene Expression Levels with Quantitative RT-PCR

Total amounts of RpL14 mRNA and the ratios of endogenous RpL14$^+$ transcript to the RpL14$^r$ rescue construct were assessed with two-step reverse-transcription quantitative PCR (RT-qPCR). RNA was isolated from 10 adult flies for each sex or 10 unsexed L3 stage larvae using Trizol (Invitrogen) and DNAse treated using a PureLink RNA Mini Kit (Invitrogen). RNA quality was assessed using a Nano-Drop spectrophotometer and 100 ng of RNA was used for cDNA synthesis using Maxima First Strand cDNA synthesis kit for RT-qPCR (Fermentas). 1 µL of the resulting reaction was used for as a template for qPCR, using TaqMan Fast Master Mix (Applied Biosystems) for relative ratios or SYBR Green Fast Master Mix (Applied Biosystems) for total RpL14 mRNA levels. Each sample was run in triplicate on an ABI 7900HT machine (Applied Biosystems).

Both wild-type and rescue PCR products were amplified with the same primer pair sitting over an intron-exon boundary; 5'-TCTTTCCGGTTAGCGTCAT (SEQ ID NO: 5); 5'-CGCCAGTCAGAGGACCAT (SEQ ID NO: 6).

Expression of wild-type and rescue transcripts were detected with TaqMan MGB probes (Applied Biosystems) labeled with FAM (wild-type) and VIC (rescue). Both probes had the same base composition, but differed by two bases, allowing for specific detection of wild-type and rescue transcripts and facilitating the calculation of ratios of expression; probe-wild-type FAM-TTGC-CAAGGCCTCCGC-MGB (SEQ ID NO: 7); probe-rescue VIC-TCGCCAAAGCCTCCGC-MGB (SEQ ID NO: 8).

For normalization of the qPCR signal, we used GeNorm method (see Vandesompele et al., 2002 Genome Biology 3: 1-12) and used 8 genes (selected by Chintapalli et al., 2007, Nature Genetics 39:715-20) as a set for normalization of qPCR reactions. These genes were tested for stability of expression in the described experimental conditions (in larvae and adults for all genotypes) across 10-log serial dilutions of cDNA template. Three of these genes, FBgn0032882, FBgn0039259 and FBgn0002021 were identified as the least variable in the flies and used for the calculation of the normalization factor. RpL14 mRNA levels are expressed relative to the normalized geometric mean of the three normalization genes.

Figure 5:
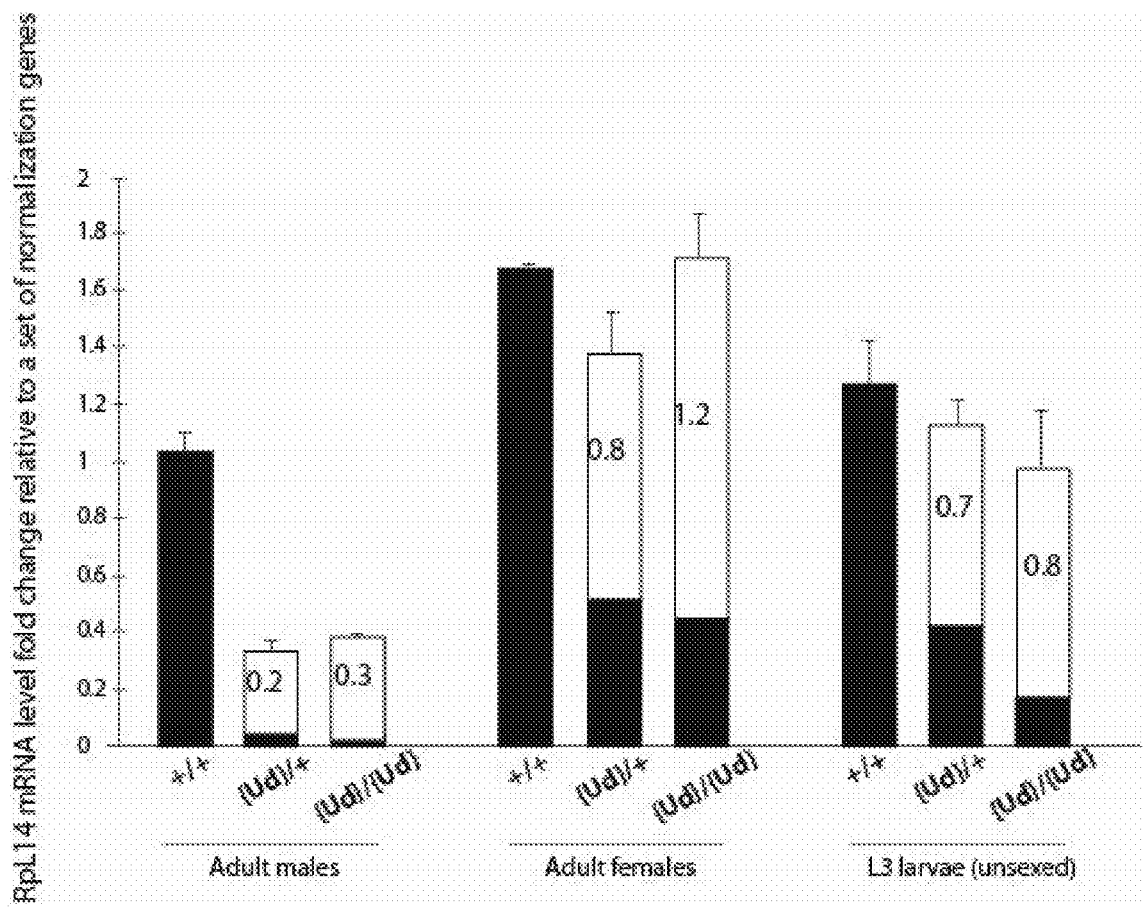
FIG. 5 shows the amount of RpL14 mRNA in adults and larvae relative to three normalization genes. Heights of bars indicate total amount of RpL14 based on SYBR green-based quantitative reverse transcription PCR and each bar is split to represent the proportion of total RpL14 expressed from the RpL14$^r$ gene in {Ud}86 (white) and the endogenous RpL14 gene (black), based on gene-specific TaqMan probes. Error bars represent 1 standard error for three biological replicates.
Figure 6:
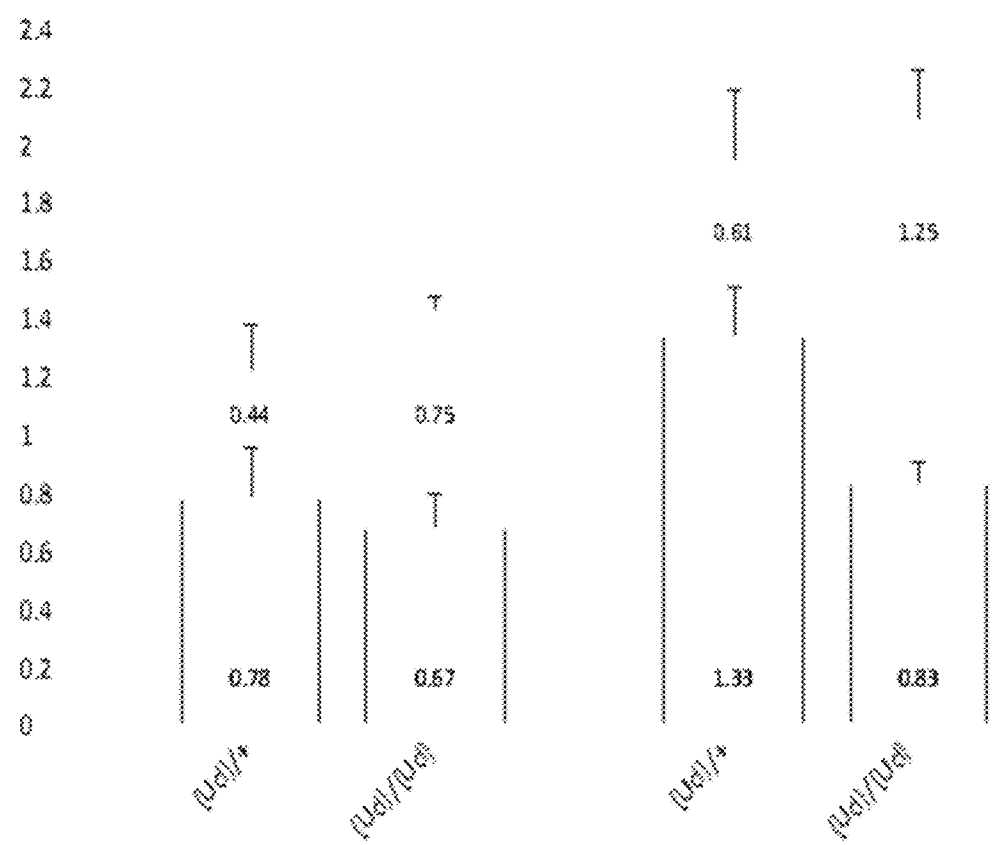
FIG. 6 shows genotypic levels of total RpL14 mRNA expression without GAL4 expression. Depicted is the amount of RpL14 mRNA in adult male genotypes (left two bars) and adult females (right 2 bars) in the absence of Act5C-GAL4 expression, relative to three normalization genes. The heights of bars indicate total amount of RpL14 based on SYBR green-based quantitative reverse-transcription PCR to the same scale as shown in FIG. 5 and each bar is split to represent the proportion of total RpL14 expressed from the RpL14 gene in {Ud}86 (white) and the endogenous RpL14 gene (black), based on gene-specific TaqMan probes. Error bars represent 1 standard error for three biological replicates.

A locus-specific RNAi induced reduction in wildtype RpL14$^+$ mRNA in both transgenic genotypes could be observed (see FIG. 5). In adult males and females heterozygotes had the lowest total amount of RpL14. However, there were striking differences in the extent of RpL14$^+$ reduction between males and females, with {Ud}86/{Ud}86 males having much less total RpL14 mRNA compared to females (see FIG. 5). The L3 larvae were not sexed and, it is not known if there are also large differences in expression levels between male and female larvae, so the larvae cannot at this time be reliably used to estimate relative genotype expression levels; however, the larvae do verify that the RNAi knockdown and rescue expression is functional at the L3 stage.

Example 3

{Ud86} Effects on Life-History Traits

Given the strong fitness reduction in heterozygotes and the pleiotropic impact of CRP hypomorphs (see S. J. Marygold et al., 2007 *Genome Biology* 8:R216; Sæbøe-Larssen, S. et al., 1997 *Molecular and General Genetics* 255:141-151), life history and morphological traits that could correlate with this genotype were examined. No overt morphological abnormalities in either {Ud}86 genotype were observed. Interestingly, heterozygotes do not exhibit the short and thin scutellar bristles that are a characteristic feature of the RpL14 Minute phenotype and most *D. melanogaster* CRP mutations. However, in common with Minute phenotypes, heterozygotes exhibited a development time prolonged by approximately 20 hours (see FIG. 7A, P<1× 10$^{-30}$), while {Ud}86/{Ud}86 homozygotes exhibited no significant differences from wildtype homozygotes (experiments described below). Furthermore, no difference in dry weight was observed between adults of the three genotypes (males, F=0.55, p=0.591; females, F=1.34, p=0.298). The relative egg-to-adult viability of the heterozygous genotype was 20%-50% lower than homozygotes (see FIG. 7B); however, this alone is insufficient to fully explain the 70-80% reduction in fitness over the entire lifecycle relative to homozygotes (see FIG. 8C; Example 4) and suggests additional factors in the lifecycle are negatively impacted in {Ud}86/+ hemizygotes.

Figure 2:
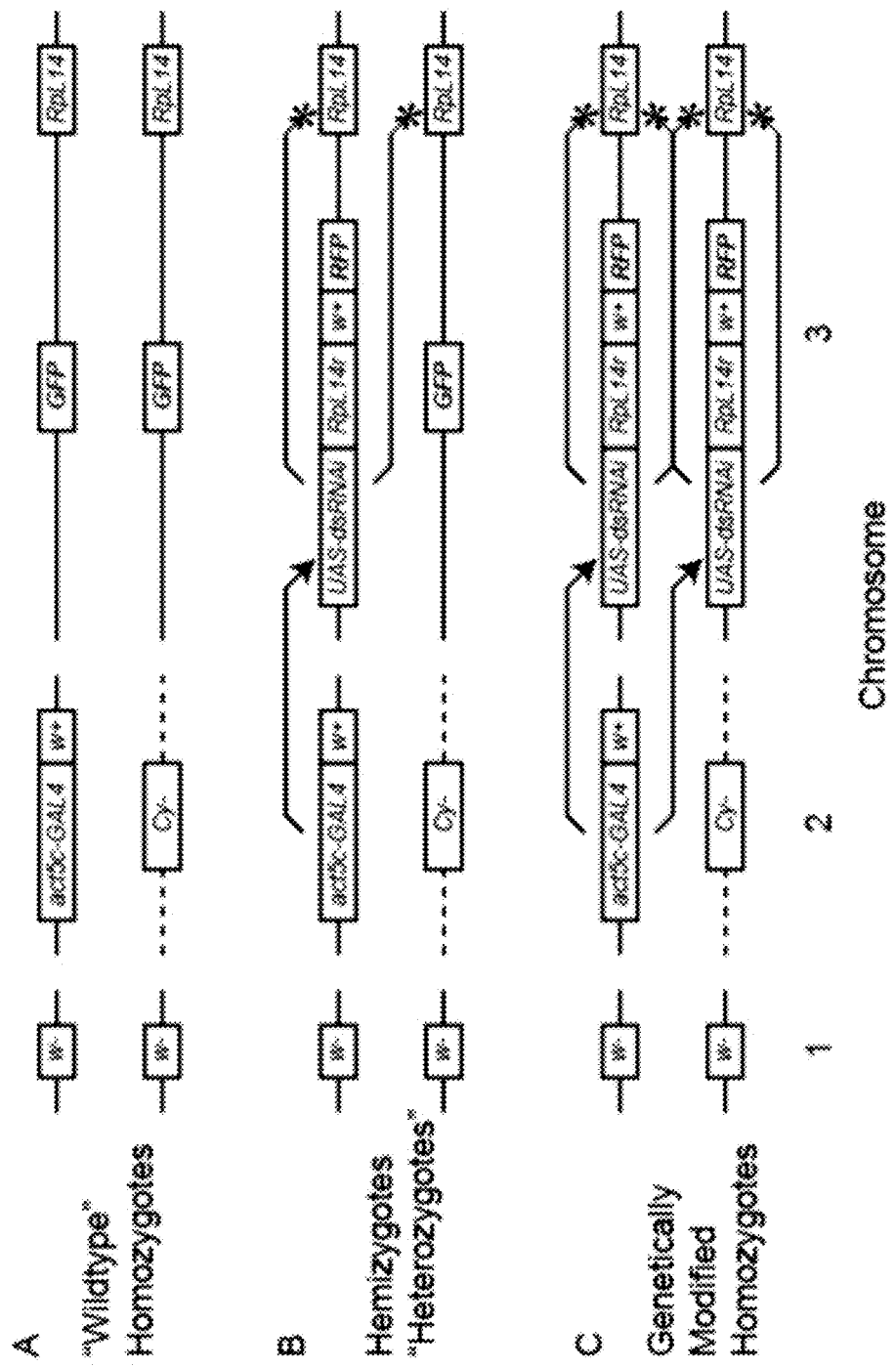
FIG. 2 shows the haploinsufficient poison-rescue underdominance strategy according to embodiments of the present invention. All flies are w$^-$ on the first chromosome and have actin driven GAL4 balanced over CyO for the second chromosome. Importantly, the actin5c-GAL4 p-element insert is marked by mini-white, so all flies are effectively wildtype for white.

In order to more precisely quantify development time and egg-to-adult departure (due to differences in viability) from expected Mendelian ratios among the three genotypes, a line was created with GFP expression from the 86Fb cytological insert site as a proxy for wildtype (see FIG. 2). This GFP stock had the genotype w[*]; CyO/P{w[+mC]=Act5C-GAL4}25FO1; M{{3x-P3-GFP}}86Fb and was generated from a modification of a plasmid (pGFP-lox-attB_12.gb.1) provided by Dr. Johannes Bischof (University of Zurich). The {Ud}86 RFP and GFP stocks were crossed to each other for >6 generations en masse, before the experiment, to help homogenize genetic backgrounds and provide some natural genetic variation on each chromosomal background.

Figure 7:
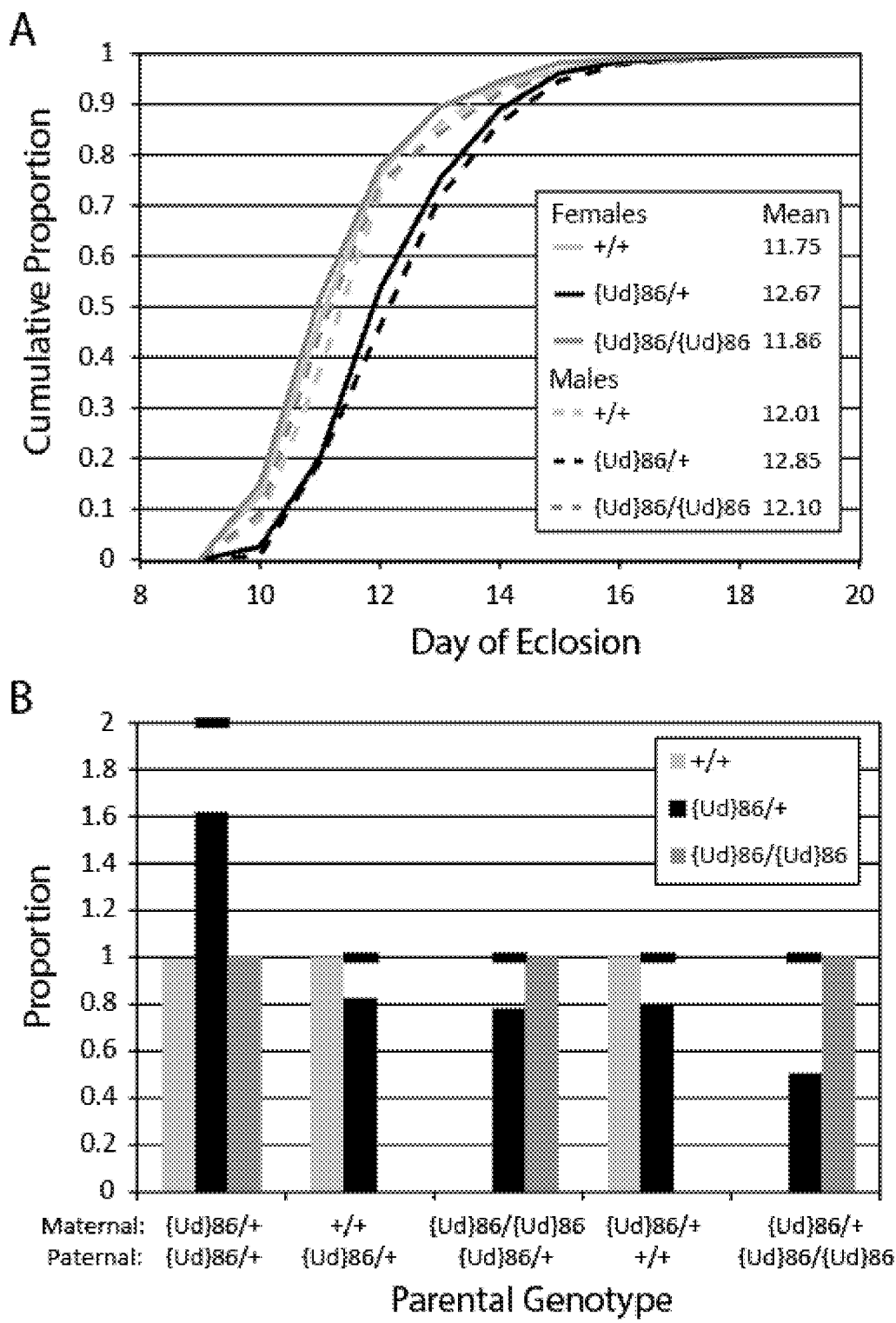
FIG. 7 depicts egg-to-adult development time and survival.

Vials were used in this experiment and crosses were set up according to the parental types indicated in FIG. 7B. The parental flies were transferred to new vials each day, for a total of 10 days, and the resulting newly eclosing offspring were scored, for sex and RFP/GFP presence/absence, each day over the following 25 days. The data is given in the following Table 2.

TABLE 2

Data from the development time and genotype viability experiments.

| | Day | | | | | | | | | | | | |
|---|---|---|---|---|---|---|---|---|---|---|---|---|---|
| | 9 | 10 | 11 | 12 | 13 | 14 | 15 | 16 | 17 | 18 | 19 | 20 | 21 |
| {Ud}86/+ × {Ud}86/+ | | | | | | | | | | | | | |
| +/+ m | 0 | 50 | 103 | 68 | 29 | 24 | 10 | 9 | 0 | 3 | 1 | 1 | 0 |
| {Ud}86/+ m | 0 | 8 | 122 | 107 | 84 | 52 | 46 | 24 | 6 | 5 | 2 | 0 | 0 |
| {Ud}86/{Ud}86 m | 0 | 39 | 94 | 63 | 22 | 26 | 14 | 12 | 3 | 0 | 0 | 2 | 0 |
| +/+ f | 2 | 82 | 81 | 52 | 36 | 25 | 14 | 9 | 4 | 4 | 1 | 0 | 0 |
| {Ud}86/+ f | 0 | 28 | 144 | 124 | 84 | 78 | 47 | 16 | 8 | 1 | 3 | 1 | 0 |
| {Ud}86/{Ud}86 f | 0 | 85 | 103 | 68 | 37 | 21 | 16 | 4 | 2 | 3 | 0 | 0 | 0 |

TABLE 2-continued

Data from the development time and genotype viability experiments.

| | Day | | | | | | | | | | | | |
|---|---|---|---|---|---|---|---|---|---|---|---|---|---|
| | 9 | 10 | 11 | 12 | 13 | 14 | 15 | 16 | 17 | 18 | 19 | 20 | 21 |
| +/+ × {Ud}86/+ | | | | | | | | | | | | | |
| +/+m | 0 | 3 | 60 | 105 | 38 | 17 | 4 | 2 | 1 | 3 | 0 | 0 | 0 |
| {Ud}86/+m | 0 | 0 | 23 | 49 | 62 | 27 | 12 | 3 | 2 | 2 | 1 | 0 | 0 |
| {Ud}86/{Ud}86 m | 0 | 0 | 0 | 0 | 0 | 0 | 0 | 0 | 0 | 0 | 0 | 0 | 0 |
| +/+f | 0 | 11 | 115 | 98 | 38 | 6 | 2 | 3 | 2 | 1 | 0 | 0 | 0 |
| {Ud}86/+f | 0 | 1 | 22 | 106 | 60 | 26 | 16 | 5 | 1 | 2 | 0 | 1 | 0 |
| {Ud}86/{Ud}86 f | 0 | 0 | 0 | 0 | 0 | 0 | 0 | 0 | 0 | 0 | 0 | 0 | 0 |
| {Ud}86/{Ud}86 × {Ud}86/+ | | | | | | | | | | | | | |
| +/+m | 0 | 0 | 0 | 0 | 0 | 0 | 0 | 0 | 0 | 0 | 0 | 0 | 0 |
| {Ud}86/+m | 0 | 0 | 18 | 43 | 43 | 29 | 12 | 2 | 0 | 0 | 0 | 0 | 0 |
| {Ud}86/{Ud}86 m | 0 | 10 | 65 | 72 | 25 | 11 | 6 | 0 | 0 | 0 | 0 | 0 | 0 |
| +/+f | 0 | 0 | 0 | 0 | 0 | 0 | 0 | 0 | 0 | 0 | 0 | 0 | 0 |
| {Ud}86/+f | 0 | 0 | 12 | 75 | 55 | 34 | 9 | 1 | 1 | 0 | 0 | 1 | 0 |
| {Ud}86/{Ud}86 f | 0 | 11 | 96 | 91 | 26 | 7 | 7 | 0 | 1 | 0 | 0 | 0 | 0 |
| {Ud}86/+ × +/+ | | | | | | | | | | | | | |
| +/+m | 0 | 0 | 21 | 49 | 13 | 1 | 1 | 0 | 0 | 1 | 0 | 0 | 0 |
| {Ud}86/+m | 0 | 0 | 2 | 22 | 33 | 14 | 2 | 1 | 0 | 0 | 0 | 1 | 0 |
| {Ud}86/{Ud}86 m | 0 | 0 | 0 | 1 | 3 | 0 | 0 | 0 | 0 | 0 | 0 | 0 | 0 |
| +/+f | 0 | 0 | 52 | 52 | 9 | 0 | 2 | 0 | 0 | 0 | 1 | 0 | 0 |
| {Ud}86/+f | 0 | 0 | 4 | 42 | 26 | 11 | 3 | 1 | 0 | 0 | 0 | 0 | 0 |
| {Ud}86/{Ud}86 f | 0 | 0 | 0 | 0 | 2 | 0 | 0 | 0 | 0 | 0 | 0 | 0 | 0 |
| {Ud}86/+ × {Ud}86/{Ud}86 | | | | | | | | | | | | | |
| +/+m | 0 | 0 | 0 | 0 | 0 | 0 | 0 | 0 | 0 | 0 | 0 | 0 | 0 |
| {Ud}86/+m | 0 | 0 | 11 | 24 | 11 | 5 | 3 | 1 | 1 | 0 | 0 | 0 | 0 |
| {Ud}86/{Ud}86 m | 0 | 3 | 43 | 31 | 6 | 8 | 4 | 2 | 1 | 0 | 0 | 0 | 0 |
| +/+f | 0 | 0 | 0 | 0 | 0 | 0 | 3 | 0 | 0 | 0 | 0 | 0 | 0 |
| {Ud}86/+f | 0 | 0 | 16 | 17 | 16 | 5 | 7 | 1 | 0 | 0 | 0 | 0 | 0 |
| {Ud}86/{Ud}86 f | 0 | 11 | 64 | 26 | 19 | 9 | 3 | 2 | 1 | 0 | 0 | 0 | 0 |

The counts of offspring from the various types of crosses presented in FIG. 7B are given below. The nine offspring with observed genotypes that were not allowed by the cross setup are underlined and in bold. These were used to estimate the genotyping error rate and were excluded from all other calculations. The female parent is listed first. Male offspring are indicated by "m" and female offspring by "f".

The heterozygous to homozygous parental backcrosses allowed the rate of erroneous genotype scoring to be estimated. Vials for each cross were given an alphanumeric identifier and offspring were scored "blind" each day without knowledge of the parental cross. A total of 9 offspring with genotypes not allowed by the cross (e.g., RFP/RFP homozygous offspring from GFP/RFP×GFP/GFP parents) were detected out of 2,636 offspring from crosses where these types of errors could be detected. Assuming that half of the erroneous genotype scores are detectable (the remaining falling into an allowed genotype category for a particular cross), the predicted genotyping error rate is 0.68%. In a worst case scenario where all genotyping errors miss scored heterozygotes as homozygous genotypes, this factor is not large enough to explain the reduction of heterozygotes in the observed data without fitness differences among the genotypes (FIG. 7B).

Dry Weight

Five sets of 10 one-day old adult flies of each sex and genotype were frozen overnight then dried in a heater for six hours at 30° C. The flies were weighed in batches of 10 at a time in order to get more accurate measurements. This data is given in the following Table 3.

TABLE 3

Dry Weight Data. Dry weights in grams for batches of 10 flies weighed at a time for each sex, replicate and genotype.

| | {Ud}86/{Ud}86 | {Ud}86/+ | +/+ |
|---|---|---|---|
| Females Genotype | | | |
| Replicate 1 | 0.0031 | 0.0032 | 0.0031 |
| Replicate 2 | 0.0030 | 0.0031 | 0.0032 |
| Replicate 3 | 0.0037 | 0.0030 | 0.0032 |
| Replicate 4 | 0.0033 | 0.0038 | 0.0031 |
| Replicate 5 | 0.0033 | 0.0034 | 0.0026 |
| Mean | 0.00328 | 0.0033 | 0.00304 |
| Males Genotype | | | |
| Replicate 1 | 0.0020 | 0.0022 | 0.0022 |
| Replicate 2 | 0.0022 | 0.0023 | 0.0023 |
| Replicate 3 | 0.0024 | 0.0022 | 0.0025 |
| Replicate 4 | 0.0026 | 0.0028 | 0.0022 |
| Replicate 5 | 0.0024 | 0.0026 | 0.0022 |
| Mean | 0.00232 | 0.00242 | 0.00228 |

Example 4

Population Experiments

To test for the frequency dependent fixation of alleles that is diagnostic of underdominance, replicated bottles over a range of frequencies were initiated. Genotypes in each generation using the dominant fluorescence of the 3x-P3-RFP marker, which is part of the landing site used in {Ud}86, were scored.

The experiment to measure allele frequency change over multiple generations was initiated with 20 mated females from the above outbred homozygous stocks, at either 20%, 50% or 80% initial {Ud}86/{Ud}86 frequencies. These already mated females were allowed to lay eggs in vials for three days and then cleared. These homozygous female parental flies were termed G0. The purpose of this generation was to minimize the possibility that differences in the condition or maturity between stocks did not strongly bias starting frequencies. The next generation, G1, is genotypically identical to the parents in generation G0, but larval development conditions are better controlled. Up to 100 G1 adults from a vial were collected, scored for sex and RFP using epi-fluorescence microscopy, and then allowed to lay eggs in a new bottle for 3 days before being cleared. Following 12 additional days of larval development, up to (approximately) 100 G2 offspring were collected scored for sex and RFP and introduced into a bottle for three days. This sequence was repeated for all subsequent generations. The G2 generation is the first in which heterozygotes are present and consequently it is the first generation in which an underdominant effect could be detected. This is why generation 2 is the first generation shown in FIG. 8A.

An egg laying time of 3 days and generation spacing of 15 days, from the time of initial addition of flies to each bottle, was chosen to maximize population sizes and minimize possible effects of developmental delay, i.e. the balance between early eclosing genotypes dying in the food and thus underscored and later eclosing genotypes being underscored. Using the curve of development time, FIG. 7A, in a worst case scenario (100% homozygous genotype survival), this would only result in a relative loss of 7% of the expected heterozygous genotypes, which is not sufficient to explain the 78% fitness reduction estimated for heterozygotes.

The strategy of scoring a RFP marker to infer the frequency of {Ud}86 makes minimal assumptions regarding fitness (it assumes Hardy-Weinberg proportions in the absence of selection). The frequency of {Ud}86 was estimated as $p=1-(R/n)$, where $R^-$ is the fraction of non-RFP expressing adults and n is the total number scored (plotted in FIG. 8A). The data is provided in the following Table 4:

TABLE 4

Data from multigenerational population experiments.

| Generation | RFP+ m | RFP+ f | RFP- m | RFP- f | {Ud86} frequency | number scored |
|---|---|---|---|---|---|---|
| Replicate A ||||||| 
| 0 | 0 | 8 | 0 | 8 | 0.5 | 16 |
| 1 | 17 | 13 | 6 | 10 | 0.652174 | 46 |
| 2 | 44 | 29 | 18 | 5 | 0.510527 | 96 |
| 3 | 33 | 34 | 20 | 13 | 0.425544 | 100 |
| 4 | 16 | 32 | 28 | 25 | 0.275602 | 101 |
| 5 | 15 | 15 | 37 | 33 | 0.16334 | 100 |
| 6 | 3 | 6 | 50 | 43 | 0.045136 | 102 |
| 7 | 2 | 0 | 50 | 48 | 0.010051 | 100 |
| Replicate B |||||||
| 0 | 0 | 12 | 0 | 3 | 0.8 | 15 |
| 1 | 21 | 37 | 6 | 5 | 0.84058 | 69 |
| 2 | 41 | 45 | 9 | 5 | 0.625834 | 100 |
| 3 | 45 | 49 | 3 | 3 | 0.755051 | 100 |
| 4 | 58 | 48 | 1 | 0 | 0.903326 | 107 |
| 5 | 38 | 64 | 0 | 0 | 1 | 102 |
| 6 | 49 | 53 | 0 | 1 | 0.901467 | 103 |
| 7 | 47 | 54 | 0 | 0 | 1 | 101 |
| Replicate C |||||||
| 0 | 0 | 3 | 0 | 12 | 0.2 | 15 |
| 1 | 8 | 4 | 16 | 22 | 0.24 | 50 |
| 2 | 18 | 19 | 31 | 32 | 0.206275 | 100 |
| 3 | 8 | 3 | 39 | 51 | 0.056025 | 101 |
| 4 | 4 | 1 | 53 | 42 | 0.025321 | 100 |
| 5 | 3 | 0 | 44 | 53 | 0.015114 | 100 |
| 6 | 0 | 0 | 60 | 44 | 0 | 104 |
| 7 | 0 | 0 | 55 | 43 | 0 | 98 |
| Replicate D |||||||
| 0 | 0 | 8 | 0 | 8 | 0.5 | 16 |
| 1 | 6 | 10 | 17 | 12 | 0.355556 | 45 |
| 2 | 30 | 33 | 18 | 19 | 0.391724 | 100 |
| 3 | 20 | 18 | 26 | 36 | 0.212599 | 100 |
| 4 | 19 | 15 | 29 | 37 | 0.187596 | 100 |
| 5 | 1 | 4 | 48 | 50 | 0.024574 | 103 |
| 6 | 1 | 0 | 49 | 48 | 0.005115 | 98 |
| 7 | 0 | 0 | 47 | 55 | 0 | 102 |
| Replicate E |||||||
| 0 | 0 | 12 | 0 | 3 | 0.8 | 15 |
| 1 | 6 | 11 | 2 | 0 | 0.894737 | 19 |
| 2 | 47 | 49 | 2 | 2 | 0.8 | 100 |
| 3 | 48 | 49 | 1 | 2 | 0.826795 | 100 |
| 4 | 48 | 52 | 0 | 0 | 1 | 100 |
| 5 | 45 | 44 | 0 | 0 | 1 | 89 |
| 6 | | | | | | |
| 7 | | | | | | |
| Replicate F |||||||
| 0 | 0 | 3 | 0 | 12 | 0.2 | 15 |
| 1 | 6 | 3 | 14 | 16 | 0.230769 | 39 |
| 2 | 14 | 12 | 42 | 33 | 0.138273 | 101 |
| 3 | 3 | 1 | 46 | 50 | 0.020204 | 100 |
| 4 | 0 | 0 | 42 | 58 | 0 | 100 |
| 5 | 0 | 0 | 48 | 52 | 0 | 100 |
| 6 | | | | | | |
| 7 | | | | | | |
| Replicate G |||||||
| 0 | | | | | | |
| 1 | | | | | | |
| 2 | 44 | 29 | 18 | 5 | 0.510527 | 96 |
| 3 | 32 | 44 | 9 | 10 | 0.552786 | 95 |
| 4 | 38 | 34 | 16 | 16 | 0.4453 | 104 |
| 5 | 43 | 36 | 16 | 9 | 0.50971 | 104 |
| 6 | 17 | 50 | 4 | 29 | 0.425544 | 100 |
| 7 | 16 | 17 | 32 | 33 | 0.185589 | 98 |
| Replicate H |||||||
| 0 | | | | | | |
| 1 | | | | | | |
| 2 | 41 | 45 | 9 | 5 | 0.625834 | 100 |
| 3 | 39 | 59 | 2 | 0 | 0.858579 | 100 |
| 4 | 50 | 53 | 0 | 0 | 1 | 103 |
| 5 | 58 | 40 | 0 | 0 | 1 | 98 |
| 6 | | | | | | |
| 7 | | | | | | |
| Replicate I |||||||
| 0 | | | | | | |
| 1 | | | | | | |
| 2 | 18 | 19 | 31 | 32 | 0.206275 | 100 |
| 3 | 4 | 4 | 57 | 35 | 0.040834 | 100 |
| 4 | 2 | 0 | 41 | 60 | 0.009756 | 103 |
| 5 | 3 | 0 | 44 | 54 | 0.014963 | 101 |
| 6 | 0 | 0 | 45 | 52 | 0 | 97 |
| 7 | 0 | 0 | 48 | 53 | 0 | 101 |

TABLE 4-continued

Data from multigenerational population experiments.

| Generation | RFP+ m | RFP+ f | RFP− m | RFP− f | {Ud86} frequency | number scored |
|---|---|---|---|---|---|---|
| Replicate J | | | | | | |
| 0 | | | | | | |
| 1 | | | | | | |
| 2 | 30 | 33 | 18 | 19 | 0.391724 | 100 |
| 3 | 14 | 30 | 27 | 30 | 0.248763 | 101 |
| 4 | 14 | 24 | 26 | 36 | 0.212599 | 100 |
| 5 | 15 | 13 | 40 | 35 | 0.14668 | 103 |
| 6 | 13 | 7 | 46 | 36 | 0.103383 | 102 |
| 7 | 4 | 5 | 49 | 50 | 0.042573 | 108 |
| Replicate K | | | | | | |
| 0 | | | | | | |
| 1 | | | | | | |
| 2 | 47 | 49 | 2 | 2 | 0.8 | 100 |
| 3 | 37 | 61 | 1 | 0 | 0.899496 | 99 |
| 4 | 48 | 58 | 1 | 0 | 0.903326 | 107 |
| 5 | 38 | 62 | 0 | 0 | 1 | 100 |
| 6 | 50 | 50 | 0 | 0 | 1 | 100 |
| 7 | | | | | | |
| Replicate L | | | | | | |
| 0 | | | | | | |
| 1 | | | | | | |
| 2 | 14 | 12 | 42 | 33 | 0.138273 | 101 |
| 3 | 10 | 0 | 54 | 36 | 0.051317 | 100 |
| 4 | 0 | 1 | 46 | 53 | 0.005013 | 100 |
| 5 | 0 | 0 | 38 | 62 | 0 | 100 |
| 6 | 0 | 0 | 44 | 56 | 0 | 100 |
| 7 | | | | | | |

The table gives the counts of RFP positive (RFP+) and RFP negative (RFP−), males (m) and females (f) each generation. Only generations 2-7, where heterozygotes could be present over the entire lifecycle, were used for plotting and fitness inference. At generation 2 line G was established from the females of line A after clearing them from A, line H was established from B, I from C, J from D, K from E, and L from F in the same manner. The estimated {Ud}86 insert frequency is also given along with the total number of adults scored. Scoring was discontinued in replicates that had reached apparent loss or fixation for two consecutive generations.

A maximum-likelihood framework (minimizing a G-statistic; see Clark et al., 1981, Heredity 46:321-46) was used to analyze the counts of RFP and non-RFP males and females between generations over a grid of transgenic homozygote and heterozygote fitness values. Changes in frequency between generations and between replicates were considered independent allowing relative likelihoods to be multiplied to generate a composite likelihood surface. Confidence intervals were calculated using a standard $\chi^2$ approximation for likelihood surfaces (plotted in FIG. 8B), i.e. assuming that the errors are normally distributed.

Confirming Homozygosity of Stocks

Homozygosity of replicates that had fixed or lost the {Ud}86 construct in the population experiment was confirmed by crossing large numbers of (n=>30) tester males to virgin females (from a w[1118]/, Dp(2; Y)G, P{w[+mC]=hs-hid}Y virginiser stock) and determining whether all offspring were RFP fluorescent or all non-fluorescent. The following primers were also used on single fly DNA extractions 5' gggccaaagtgtaaataactgg-3' (SEQ ID NO: 9) and 5' aaaatgtccattactttggtgct-3' (SEQ ID NO: 10) to give a 136 bp PCR product (3R:7634237 . . . 7634372) identifying the presence of wildtype third chromosomes (+) and a theoretical product of >10 kb for {Ud}86. Presence of {Ud}86 could be confirmed by using 5' actttccttccgatggacct-3' (SEQ ID NO: 11) and 5' aatgaccaccgtctttcagc-3' (SEQ ID NO: 12) resulting in a 135 bp PCR product from the RFP gene. PCR genotyping by multiplexing both primer sets was not done as this was found to be unreliable.

In summary, FIG. 8A shows a consistent and rapid rise in the frequency of {Ud}86 when above a threshold frequency (estimated at 0.61) and a corresponding decline when below it. The elimination of either + or {Ud}86 based largely on its initial frequency demonstrates the inherent reversibility of underdominant population transformation and also underlies the spatially self-limiting nature of underdominant population transformation. Using a maximum-likelihood approach the relative fitness of the three genotypes was estimated as +/+=1, +/{Ud}86=0.22, {Ud}86/{Ud}86=0.71 (FIGS. 8B and 8C). The reduction n in fitness among the genotypes is consistent with changes in total mRNA abundance of RpL14 (FIG. 9). These fitness values represent a strongly underdominant system where if the {Ud}86 allele is above 61% in a population it is predicted to deterministically (in the absence of stochasticity) proceed to fixation. Considering 3x-P3-RFP as an effector gene, we have demonstrated that the {Ud}86 construct is capable of stably transforming a population to carry the marker for producing red fluorescent protein.

Due to the >3 fold reduction in fitness of +/{Ud}86 heterozygotes relative to {Ud}86/{Ud}86 homozygotes (see FIG. 8C) it is expected that {Ud} would be well suited to fixing even strongly deleterious linked effector genes and remaining underdominant (see Scott et al., 2002, Science 298:117-9).

Example 5

Geographic Stability and Dynamics of Underdominant Population Transformation

Optimal release strategies have been assessed in Altrock et al., 2011 PLoS Computational Biology, 7:e1002260 and Altrock et al., 2010 Journal of Theoretical Biology, 267:62-75 for a simple but meaningful geographic pattern. In the following a quantitative analysis of geographic stability properties of underdominant population transformation with {Ud} constructs is provided. The indicated mathematical methods serve as a quantitative justification for the geographic stability properties discussed herein.

It is assumed that transformation of a target population has already been achieved and the systems potential of further spread of {Ud} compared to the possibility of complete loss of {Ud} is of interest. The mathematical evolutionary model is based on genotypic fitness parameters, migration rates between neighboring populations, and population size, which determine the intrinsic time scale of the extinction process.

In a single locus two allele model the genotypic fitness values that determine the population dynamics of the described system are $$w_{+/+}, w_{+/\{Ud\}86}, \text{ and } w_{\{Ud\}86\{Ud\}86}.$$

Figure 8:
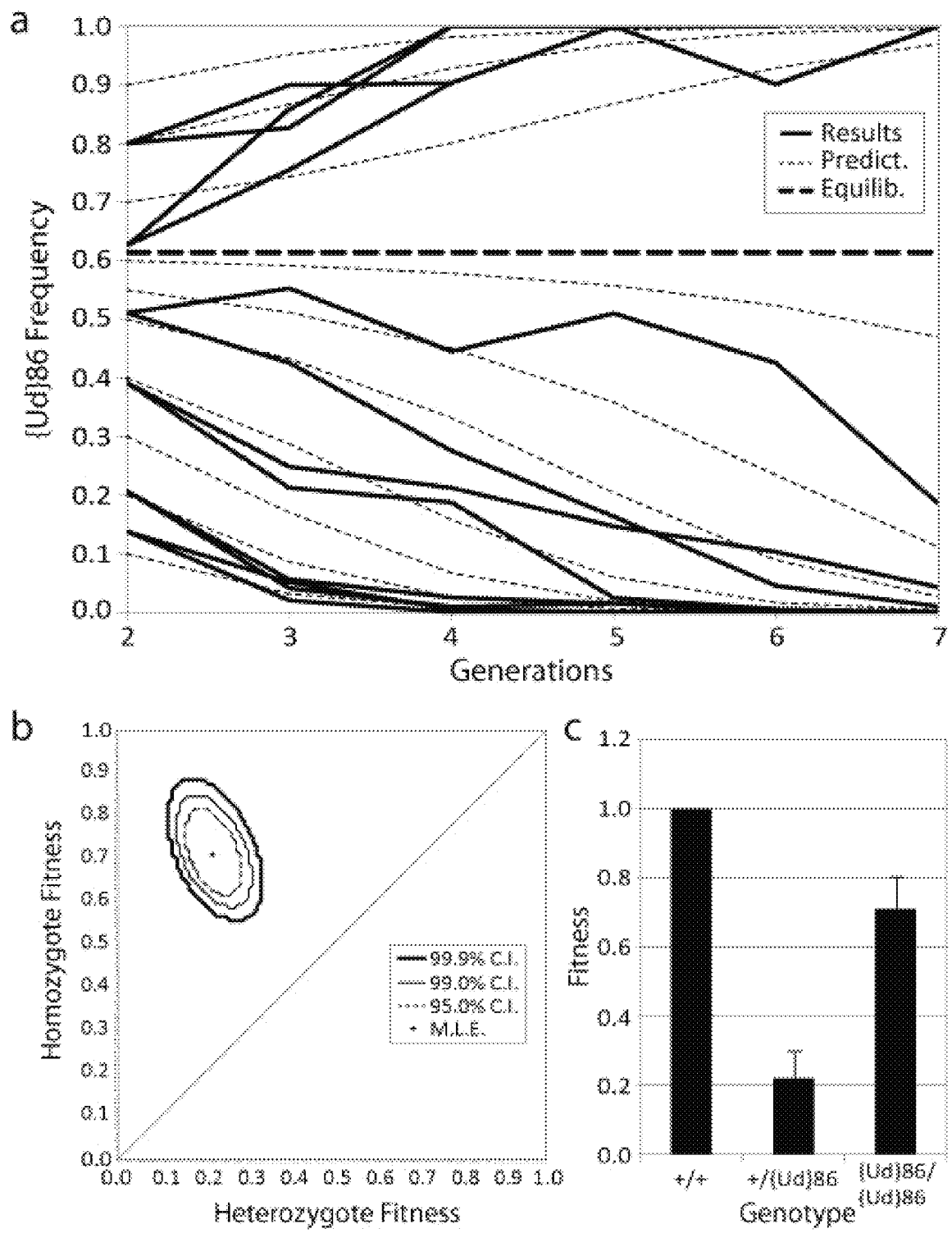
FIG. 8 shows {Ud}86 population experiments demonstrating underdominance.
Figure 9:
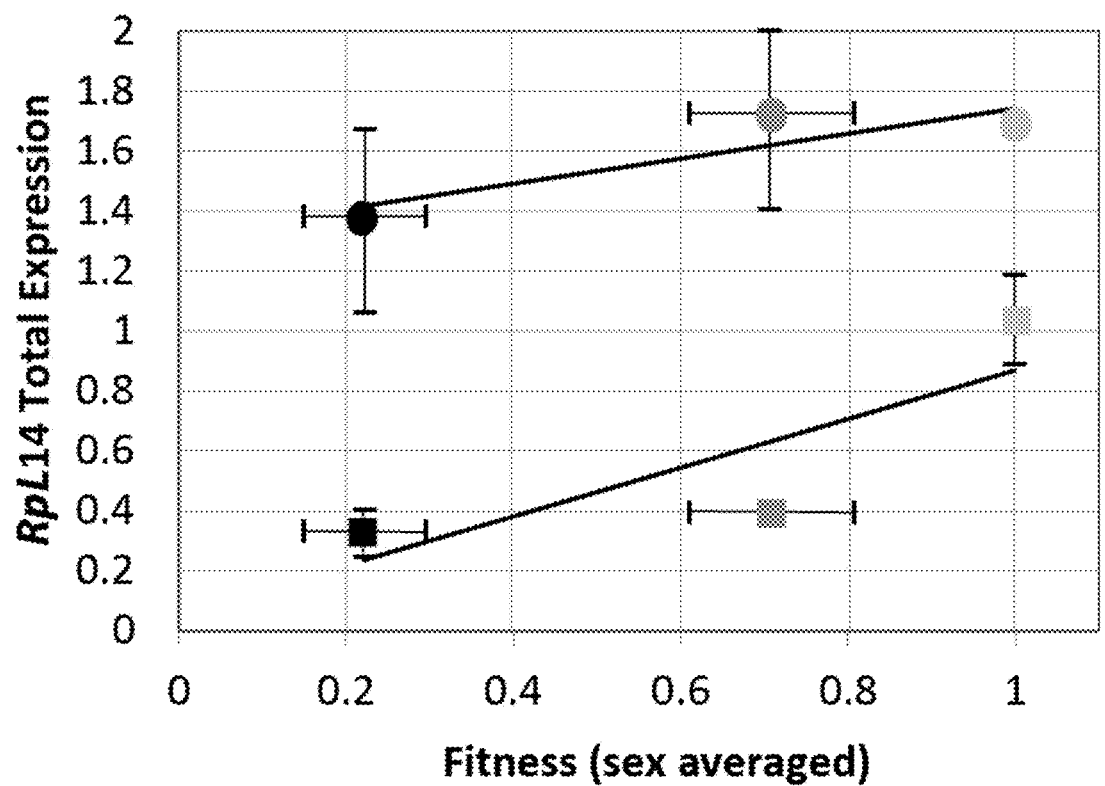
FIG. 9 illustrates the association between total adult RpL14 mRNA abundance and total lifetime fitness as estimated from allele frequency changes between generations. A reduction in expression is consistent with a reduction in fitness. The data plotted here is the same as is used in FIG. 5 and FIG. 8. Data for males are plotted in squares and females in circles. Light gray indicates +/+ genotypes, medium gray indicates {Ud}86/{Ud}86 homozygotes, and black indicates {Ud}86/+ hemizygotes. Fitted least-squares regression lines for males and females are given for illustrative purposes only.

For the analytical and simulation results the MLE fitness estimates of the transgenic genotypes was used, (see FIG. 8 (C)):

$$w_{+/+}=1, w_{+/\{Ud\}86}=0.22, \text{ and } w_{\{Ud\}86\{Ud\}86}=0.71.$$

Under random mating (random union of gametes) it is assumed that diploid individuals pass through Hardy-Weinberg expectations before selection, and thus describe the population system in terms of single alleles (see Altrock et al., 2010 Journal of Theoretical Biology, 267:62-75; Hartl and Clark, Principles of Population Genetics A. D. Sinauer, Ed. (Sinauer Associates, 1997), p. 542). The frequency threshold to transform a target population, neglecting migration, is $$\frac{w_{+/+} - w_{+/\{Ud\}}}{w_{+/+} + w_{\{Ud\}/\{Ud\}} - 2w_{+/\{Ud\}}}, \quad \text{(eq. 1)}$$

which determines an unstable equilibrium of the evolutionary dynamics.

Given that the target population has been transformed, two further threshold allele frequencies can be estimated, respecting migration of gametes prior to mating. First, an approximation for the threshold to transform the neighboring population, under the assumption that the target population is unaffected, can be calculated. Second, the threshold for a transformation of the target population back to wildtype, due to migrants from neighboring wild populations, can be approximated.

For the migration-selection dynamics, the expected allelic fitness values are affected by the migration rate per generation (or any other unit time), but the genotypic fitness values remain constant. The rate of immigrants into a given population prior to mating is given by m. The expected allelic fitness values depend on the allele frequencies, and thus on migration rate. Under the Hardy-Weinberg assumption all fitness values can be expressed in terms of the frequency of {Ud}: $p_T$ in the target population, and $p_N$ in a neighboring population. For a wildtype allele +

$$f_+ = (1-p_T)w_{+/+} + p_T w_{+/\{Ud\}} + m(p_T-p_N)(w_{+/+} - w_{+/\{Ud\}}) \quad \text{(eq. 2)}$$

Likewise, for the underdominant construct allele {Ud}

$$f_{\{Ud\}} = (1 p_T)w_{+\{Ud\}} + p_T w_{\{Ud\}/\{Ud\}} - m(p_T - p_N)(w_{\{Ud\}/\{Ud\}} - w_{+\{Ud\}}) \quad \text{(eq. 3)}$$

Figure 10:
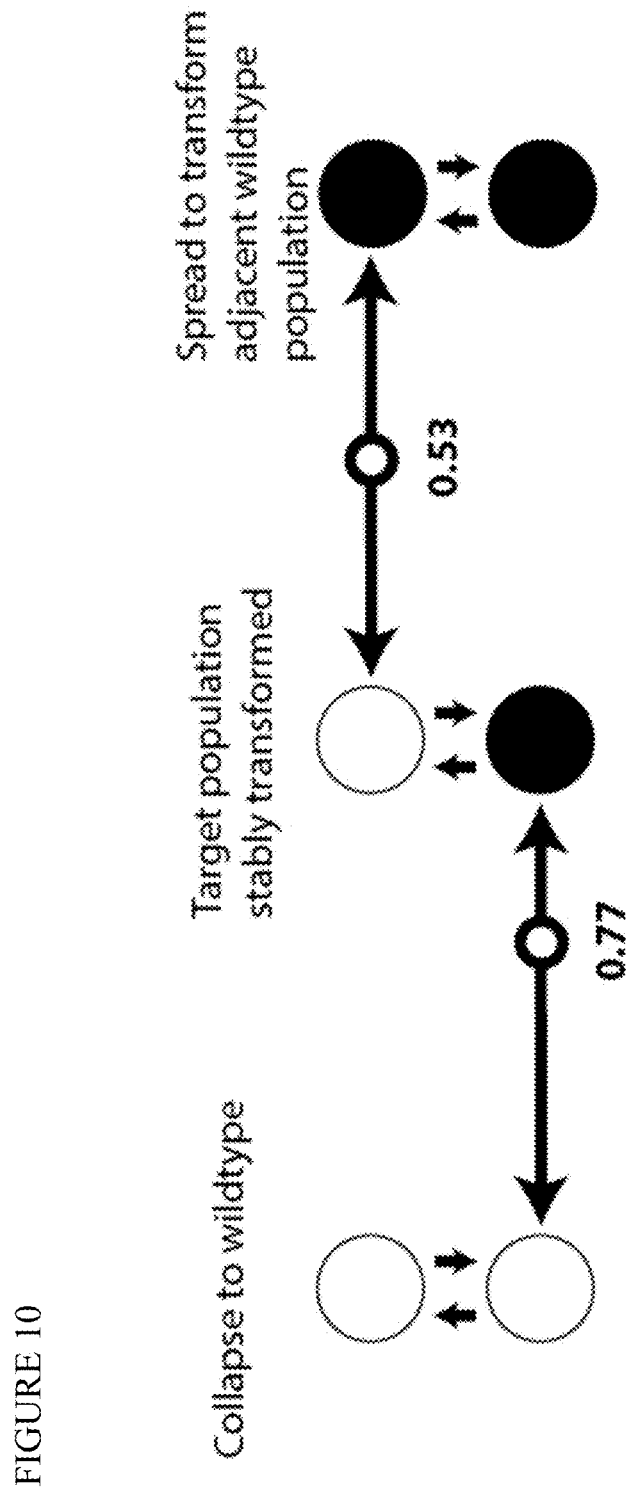
FIG. 10 depicts geographic stability data. The figure shows interconnected populations which are represented as circles, (light gray for wildtype and dark gray for a {Ud}86 transformed population). If a single target population is transformed (center) migration can result in two undesired transitions; collapse of population transformation through loss of {Ud}86 from the target population (left), or spread of {Ud}86 by transformation of an adjacent wildtype population (right). For a migration rate of 0.065 every generation and with the fitness configuration given in FIG. 8B; collapse is only likely to occur if the frequency of {Ud}86 drops below <0.77; spread is only likely to occur if {Ud}86 reaches >0.53 frequency in an adjacent wildtype population. Simulations incorporating drift indicate that for population sizes above 25 individuals the relative probability of collapse is essentially infinitely greater than for spread.

In the second terms of Equations (2), and (3) an important asymmetry in the effect of migration on the average fitness values of the two alleles is noticeable, which eventually leads to the asymmetry described in FIG. 10. The average population fitness in the target population is $$F_T = (1-p_T)f_+ + p_T f_{\{Ud\}} - m(p_T-p_N)(f_{\{Ud\}} - f_+) \quad \text{(eq. 4)}.$$

With the fitness functions (2), (3), and (4) the temporal change of the frequencies of allele {Ud} in the target population, $\Delta p_T$, and in the neighboring population, $\Delta p_N$, per time step $\Delta t$ (typically one generation) can be described (see Altrock et al., 2011 PLoS Computational Biology, 7:e1002260; Altrock et al., 2010, Journal of Theoretical Biology, 267:62-75; Hartl and Clark, Principles of Population Genetics A. D. Sinauer, Ed. (Sinauer Associates, 1997), p. 542), $$\Delta p_T(p_T, p_N) = \Delta p_T(f_{\{Ud\}} - F_T) - m\Delta t(p_T - p_N)f_{\{Ud\}} \quad \text{(eq. 5)}$$

The equation for $\Delta p_N$ follows by exchanging $p_N$ and $p_T$, $$\Delta p_N(p_T, p_N) = \Delta p_T(p_N, p_T) \quad \text{(eq. 6)}.$$

The two equations for the evolutionary dynamics of the frequency of {Ud} in target and neighboring populations (equations 5 and 6) are used to give quantitative estimates for the bi-stable properties and geographic stability in infinitely large populations, FIGS. 8 and 10. The calculation of the thresholds used in FIG. 10 then follows from finding the roots of $$\Delta p_T(\rho_T, 0) = 0, \text{ and } \Delta p_N(\rho_N, 1) = 0.$$

For back-transformation of the target population due to immigration from neighboring populations $p_T$ has to be below $\rho_N$, i.e., increase wildtype from 0 to $1-\rho_T$ frequency. In wild populations, $\rho_N$ is the threshold for transforming a single neighboring population due to emigration from the transformed target. In the following the constant fitness of wildtype homozygotes was set to one, all other fitness values are given in relative terms, $w_{+/+}=1$.

With this the thresholds can be found to have the following form $$\rho_T = \frac{A_T + \sqrt{B_T}}{2(1-m)(1 + w_{\{Ud\}/\{Ud\}} - w_{+/\{Ud\}})}, \quad \text{(eq. 7)}$$

$$\rho_N = \frac{A_N - \sqrt{B_N}}{2(1-m)(1 + w_{\{Ud\}/\{Ud\}} - w_{+/\{Ud\}})}, \text{ with} \quad \text{(eq. 8)}$$

$$A_T = 2 + w_{\{Ud\}/\{Ud\}} - 3w_{+/\{Ud\}} - m(w_{\{Ud\}/\{Ud\}} - w_{+/\{Ud\}}) \quad \text{(eq. 9)}$$

$$A_N = 1 - w_{+/\{Ud\}} - m(1 - 2w_{\{Ud\}/\{Ud\}} - 3w_{+/\{Ud\}}) \text{ and} \quad \text{(eq. 10)}$$

$$B_T = (1-m)^2(w_{\{Ud\}/\{Ud\}} - w_{+/\{Ud\}})^2 - 4m(w_{\{Ud\}/\{Ud\}} - (w_{+/\{Ud\}})^2), \quad \text{(eq. 11)}$$

$$B_N = (1-m)^2(1 - w_{+/\{Ud\}})^2 - 4m(w_{\{Ud\}/\{Ud\}} - (w_{+/\{Ud\}})^2). \quad \text{(eq. 12)}$$

There can only be meaningful results as long as $B_T$, and $B_N$ are nonnegative, which holds for migration below critical thresholds. As migration goes to zero, both thresholds converge to the well-known threshold in isolated populations, equation (1). It also becomes obvious that $\rho_N \le \rho_T$ for migration below critical bounds. This asymmetry is responsible for the self-limiting property: loss is more likely than spread (see Altrock et al., 2011, PLoS Computational Biology, 7:e1002260).

Equations (2), (3), and (4) can also be used to mathematically model stochastic dynamics in finite populations, either using a Moran or Wright-Fisher approach (see Altrock et al., 2011, PLoS Computational Biology, 7:e1002260 and Altrock et al., 2010, Journal of Theoretical Biology, 267: 62-75). Such simulations also reveal that only population sizes of a magnitude below $10^2$ have a realistic chance that undesired spread to neighboring populations may occur.

Example 6

Currently, there are only two population transformation systems that have worked in laboratory experiments: a maternal poison-rescue system termed Medea and a homing-endonuclesase base system termed HEG. As a single locus, neither Medea or HEG achieved complete fixation in experimental populations, with the equilibrium frequency of wildtype alleles remaining at approximately 0.1 for Medea (see FIG. 1F in Chen et al., 2007, Science, 316:597-600) and >0.1 for HEG (supplementary FIG. 5 in Windbichler et al., 2011, Nature, 473, 212-215), while complete fixation is achieved for {Ud}86 (FIG. 8A). A potential concern is that persisting wildtype alleles could facilitate selection for resistance by the insect to the driving properties of HEG or Medea or by the pathogen to the linked disease refractory gene (see Scott et al., 2002, Science 298:117-9). The underdominant approach demonstrated here avoids this complication by rapidly eliminating all wildtype alleles in a population (see, for example, FIG. 8A).

The initiation of underdominant population transformation is a more resource intensive approach than for HEG or Medea, where very small numbers of individuals can be released and the genetic modification invades from low frequencies; for {Ud}86 this would require much larger numbers in order to exceed an allele frequency of 0.61 in a wild population (see FIG. 8A). However, the predicted release sizes are much smaller than those successfully used in sterile insect techniques (which can be >10 times the wild population size). Furthermore, in situations where spatial control, or recall ability, is valued, FIG. 10 illustrates the extent of the geographic stability {Ud}86 could exhibit even with substantial levels of migration. Obvious candidates for {Ud} transformation include the mosquitoes *Culex quinquefasciatus, Aedes aegypti* and *Anopheles stephensi*, where refractory genes have been developed for dengue fever, human malaria and avian malaria (see Isaacs et al., 2011, PLoS Pathogens 7:e1002017; Jasinskiene et al., 2007, The American Journal of Tropical Medicine and Hygiene, 76:1072-8; and Franz et al., 2006, PNAS, 103:4198-203).

Example 7

{Ud} in Plants

In addition to insect population transformation {Ud} constructs have other high value applications, for example in limiting unwanted out-crossing of genetically modified plant cultivars whilst preserving crop yields and the ability of farmers to save seed from year to year (see Hills et al., 2007, Trends in Plant Science, 12:177-83).

The fact that the dry weight and morphology of {Ud}86/{Ud}86 flies were indistinguishable from wildtype is suggestive that it would be possible to develop {Ud} germline transformation plasmids for plants that would not negatively impact crop yields. If crop germline transformation routinely used underdominant plasmids out-crossing may render hybrid plants highly unfit or dead. In the field this would limit hybridization between different genetically modified crop varieties grown adjacent to each other and control hybridization with wild relatives or non-genetically modified crops, including traditional varieties. This may also allow pure breeding stocks to be maintained more efficiently because unwanted crosses would be suppressed. Furthermore, a useful elaboration in plants is to limit {Ud} expression to the roots so that cell competition in the germline, which may promote mutations that disrupt the {Ud} system, is inhibited.

Example 8

{Ud} and Engineered Nucleases

The fact that RpL14 was the first gene selected for the development of this technique suggests that this approach may be readily applied in other non-model organisms. The haploinsufficiency and the deleterious nature of CRP mutations is well conserved across wide evolutionary distance with numerous examples in fungi, *Arabidopsis, Drosophila*, zebrafish, humans and mice (see Table 1). Consequently, CRPs should represent a rich source of genes that can potentially be targeted by {Ud} constructs in any sexually reproducing eukaryote.

As an alternative to targeting the mRNA of haploinsufficient genes by RNAi, it is also possible to target their chromosomal DNA using zinc finger nucleases (ZFNs), Transcription Activator-Like Effector Nuclease (TALEN), a CRISPR or meganucleases. These are synthetic restriction endonucleases where it is possible to engineer the recognition sequence. These synthetic nucleases could be used to knock-down expression by inducing null mutations in haploinsufficient genes through non-homologous end joining repair of doubles stranded chromosomal breaks induced by ZFNs, TALENs, CRISPR or meganucleases (e.g. targeted to transcription initiation sites). The rescue copy would again be insensitive to targeting due to the introduction of benign mutations, this time at the nuclease recognition site. In addition to enhancing the predictability and effectiveness of targeting, the use of ZFNs, TALENs, CRISPR or meganucleases have the potential to further reduced the loss of fitness in {Ud}/{Ud} homozygotes. Finally the use of ZFNs, TALENs, CRISPR or meganucleases extends the {Ud} approach to sexual organisms where RNAi targeting is ineffective.

Example 9

{Ud} and Countering the Colony Effect

{Ud} constructs also have the potential to overcome a problem common to many programs involving the long-term mass release of insects, particularly genetically modified ones. This is a pronounced reduction in fitness of released individuals due to selection for phenotypes that are advantageous for colony maintenance but which are deleterious upon environmental release. The accumulation of deleterious alleles in small captive populations may also contribute, and inbreeding associated with long-term colony maintenance exacerbates these effects. Continuous outbreeding of colonies with wild caught individuals whilst maintaining homozygosity at a transgenic locus in release individuals is generally impractical. However, underdominant colonies could readily be maintained as fully outbred by adding a percentage of wild caught individuals every generation well under the threshold frequency required for transformation. Homozygous individuals intended for release could come from sub-colonies maintained for a small number of generations without the addition of wild caught individuals that would become substantially homozygous at the {Ud} locus. This colony fitness reduction would not likely compromise short-term releases necessary for population transformation approaches, but the long-term suppression of insect populations sizes using transgenic sterile insect technique (SIT) is likely to be impacted. The use of {Ud} germline transformation constructs would be extremely valued in maintaining the long-term fitness of these types of colonies.

Example 10

Functionally Cross-Linking Underdominant Loci

A functional cross-linking underdominant approach is based on the presence of the following elements:
P1=poison reducing haploinsufficient gene 1
P2=poison reducing haploinsufficient gene 2 (not the same gene as 1)
R1=rescue gene 1
R2=rescue gene 2
In one configuration the two functionally independent underdominant loci on different chromosomes in the same genome are exemplified by the formula:

{P1,R1};{P2,R2}

In this setup, the rescue gene and the poison are physically linked at each locus, while the loci are not functionally cross linked.

The individuals homozygous for both loci are mated with a wildtype, as outlined below:

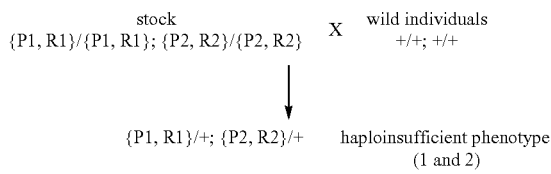

{P1, R1}/+; {P2, R2}/+    haploinsufficient phenotype (1 and 2)

The offspring are mated, while the phenotype is not 100% lethal or infertile, with any genotype. The outcome of this mating is shown below:

| | |
|---|---|
| {P1, R1}/{P1, R1}; {P2, R2}/+ | haploinsufficient phenotype (2) |
| {P1, R1}/{P1, R1}; +/+ | wildtype rescue phenotype |
| {P1, R1}/{P1, R1}; {P2, R2}/{P2, R2} | wildtype rescue phenotype |
| {P1, R1}/+; {P2, R2}/+ | haploinsufficient phenotype (1 and 2) |
| {P1, R1}/+; +/+ | haploinsufficient phenotype (1) |
| {P1, R1}/+; {P2, R2}/{P2, R2} | haploinsufficient phenotype (1) |
| +/+; {P2, R2}/+ | haploinsufficient phenotype (2) |
| +/+; +/+ | wildtype |
| +/+; {P2, R2}/{P2, R2} | wildtype rescue phenotype |

In an alternative approach, the two loci are functionally crosslinked:

{P1,R2}/{P1,R2};{P2,R1}/{P2,R1}

Individuals homozygous for both loci are mated with a wildtype according to the following scheme:

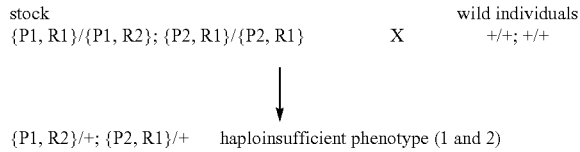

{P1, R2}/+; {P2, R1}/+    haploinsufficient phenotype (1 and 2)

The offspring are mated, while the phenotype is not 100% lethal or infertile, with any genotype. The outcome of this mating in subsequent generations is shown below:

| | |
|---|---|
| {P1, R2}/{P1, R2}; {P2, R1}/+ | haploinsufficient phenotype (1) |
| {P1, R2}/{P1, R2}; +/+ | LETHAL (no R1) |
| {P1, R2}/{P1, R2}; {P2, R1}/{P2, R1} | wildtype rescue phenotype |
| {P1, R2}/+; {P2, R1}/+ | haploinsufficient phenotype (1 + 2) |
| {P1, R2}/+; +/+ | LETHAL (no R1) |
| {P1, R2}/+; {P2, R1}/{P2, R1} | haploinsufficient phenotype (2) |
| +/+; {P2, R1}/+ | LETHAL (noR2) |
| +/+; +/+ | wildtype |
| +/+; {P2, R1}/{P2, R1} | LETHAL (noR2) |

Since in the functionally cross-linked setup the introgression or population transformation relies on both haploinsufficiency and lethality, the second approach with cross-linked P1, R2 and P2, R1 is highly efficient, in particular for:

(1) BIOCONTAINMENT since any F1 escapers only have 1 genotype out of 9 where they have wildtype fitness. In the uncrosslinked approach 4 out of 9 genotypes are wildtype fitness (based solely on haploinsufficiency).

(2) WILD POPULATION SIZE SUPPRESSION since any F1 escapers have reduced viability.

(3) POPULATION TRANSFORMATION since it relies on two different mechanisms, namely haploinsufficiency and unrescued poisoning.

Example 11

Underdominance in Plants Using TALEN and miRNA or Other Targeting Mechanisms

The success of the experimental approach in demonstrating underdominance relies on finding {Ud} insertions which cause a strongly haploinsufficient phenotype as heterozygotes, but are not so severe that all plants are inviable or infertile. This phenotype then needs to be substantially rescued in some or all plants homozygous for the insert. Timely success will depend on surveying a sufficient number of insertion sites to find those, which are underdominant Tandem insertions of >3 are not expected to be underdominant due to having excessive rescue copies for haploinsufficiency. T-plasmid transformation is known to provide a range of tandem copy numbers. In some circumstances also multiple insertions could prove to be underdominant.

Figure 13:
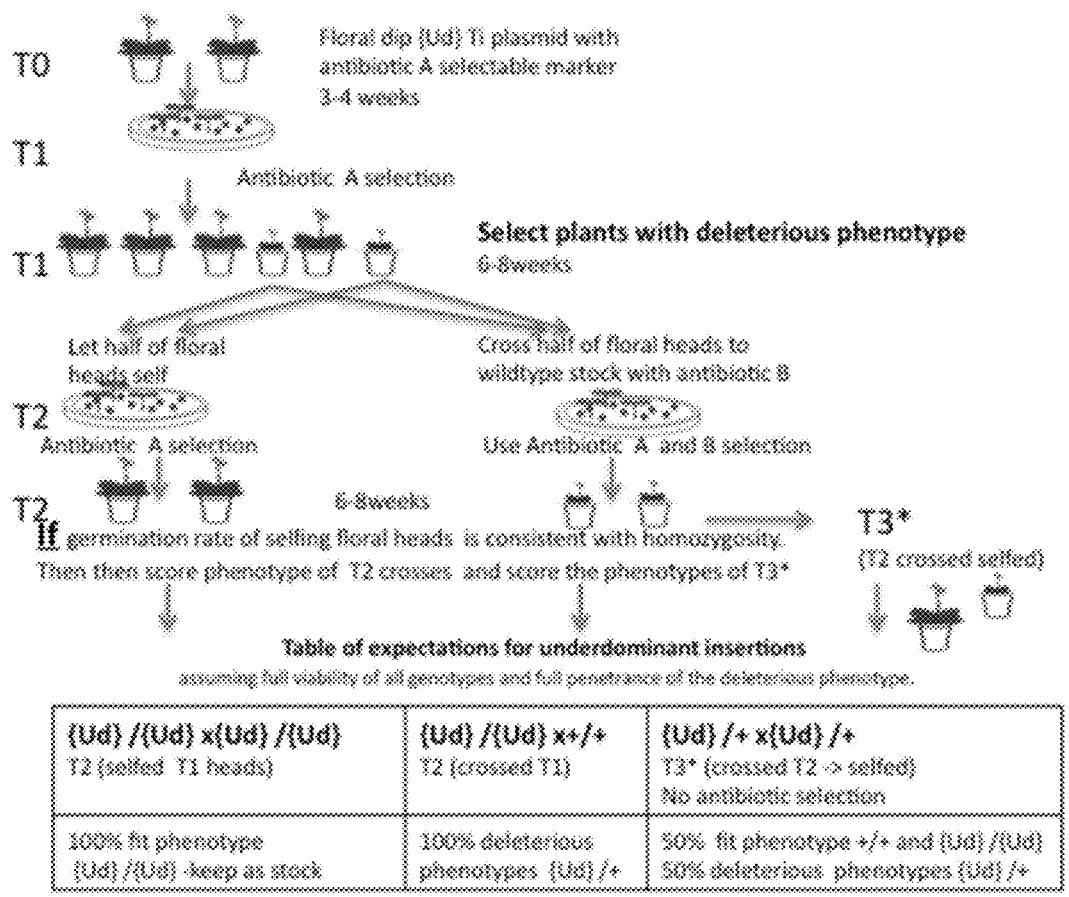
FIG. 13 is a scheme depicting an experiment to identify underdominant inserts in plants.

The experiment to identify underdominant inserts in plants I performed using variations according to FIG. 13.

The aberrant phenotype is described relative to wildtype or control plants in terms of properties likely to impact the competitive fitness of the plants (for example fertility, growth rate, stress tolerance). The degree of phenotypic rescue is described in terms of the relative reduction in the severity of the aberrant phenotype and or the competitive fitness of heterozygotes relative to homozygotes.

Insertions where agronomic traits such as stress tolerance and crop yield are not negatively impacted in homozygotes, while heterozygotes experience a significant loss of competitive fitness will be of particular value. If the frequency of the aberrant phenotype is substantially reduced in the T2 generation compared to the T1 generation that indicates an underdominant insert.

Example 12

Generation of Entry Plasmids for TALEN Experiment

For an implementation of the TALEN-based underdominance approach a TALEN construct is directly cloned into entry vectors, because TALENs cannot be PCR amplified and cannot be supplied in a gateway vector (plasmid 1 and 3).

Plasmid 2 is also assembled directly into entry vector since in 3 fragments need to be incorporated. TALEN1 and TALEN2 are half sites of the same protein. Cloning is done in normal cells.

The plasmid construction is carried out according to the following Table:

| | Plasmid name | | |
|---|---|---|---|
| | 1 | 2 (jai) | 3 |
| Source plasmids | TALEN 1 (Amp)-RE digest 5500bp | Terminator PCR from MIGS3.1 (Kan), 731bp | TALEN 2 (Amp) - RE digest 5500bp |

-continued

| | Plasmid name | | |
|---|---|---|---|
| | 1 | 2 (jai) | 3 |
| Source | | Rescue (RpL23aA including all regulatory sequences but with about 15 synonymous changes made, will flank with Cre/lox sites for flipping out rescue in plasmid and in vivo PCR(Amp)2500bp | |
| Source plasmids | | P35S→ PCR from MIGS3.1 (Kan!), 841bp | |
| Source plasmids DpnI digest | pENTR L1-L4 PCR (Kan), 2570bp | pENTR R4R3 PCR (Kan) 2535bp | pENTR L3-L2 PCR (Kan!), 2551bp |
| method of cloning | Genart 2 fragments | Geneart-PCR 4 fragments or (7 if rescue is simultaneously assembled) | Genart 2 fragments |
| Selection | Blue white Kan | Kan Spectinomycin sensitivity | Kan Tetracycline sensitivity |
| Results in | L1-TALEN1-L4 | R4-Terminator-Rescue-Pro→-R3 | L3-TALEN2-L2 |

Generation of Entry Plasmids for miRNA Experiment and Fluorescent Markers

For miRNA experiments plasmids for two different miR-NAs (TTACTTACCAGTTATAGGCAT (SEQ ID NO: 13) & TGTAAGCCTCACGTAAGGCTA (SEQ ID NO: 14)) are provided. The plasmid construction for miRNA experiments and fluorescent markers is carried out according to the following Table:

| | Plasmid name | | |
|---|---|---|---|
| | 4 | 5 | 6 |
| Source plasmids | B1-synthesised fragment miRNA-B4 pDONR 221 P1-P4 | B3-mCitrine-B2 PCRattb pMD146 # x | B1-mCherry-B4 PCRattb MD143 pDONR 221 P1-P4 |
| Entry vector full name | pENTR L1-miRNA-L4 | pENTR L3-L2 | pENTR L1-L4 |
| method of cloning | Gateway BP clonaseII | Gateway BP clonaseII | Gateway BP clonaseII |
| Selection | ccdB Kan | ccdB Kan | ccdB Kan |
| Results in | L1-miRNA-L4 | pENTR L3 ≥mCitrine NLS L2 | pENTR L1 ≥mCitrine NLS L4 |

LR Gateway Reaction (3 Fragments)

Destination vector MIGS3.1 (where miR173 gene has been removed by BamHI digestion and re-ligation) is constructed according to the following scheme:
(promoter) 35s→-attR1-attR2 rbcs
Selection ccdB, Bar selection in plants

| experiment | final | Plasmids used in LR |
|---|---|---|
| TALEN | 35s→: T1: rbcs -Rescue- 35s →: T2: rbcs | 1 + 2 + 3 + MIGS3.1 |
| miRNA | 35s→: miRNA: rbcs -Rescue- 35s →: mCitrine: rbcs | 4 + 2 + 5 + MIGS3.1 |
| Poison control for each construct (do TALENs and miRNAs cause a dominant phenotype) | 35s→: T1: rbcs - - 35s →: T2: rbcs or 35s→: miRNA: rbcs - - 35 s →: mCitrine: rbcs | Each of the above plasmids exposed to Cre recombinase. Can also be done in vivo using arabidopsis.org/ servlets/TairObject?id= 1010229171&type= germplasm |
| Rescue control for all experiments (does rescue alone cause a dominant phenotype) | 35 s→: RED : rbcs -Rescue- Pro→: mCitrine: rbcs | 2 + 5 + 6 + MIGS3.1 |

Example 13

Generation of Plasmids for miRNA Targeting Experiment

Figure 11:
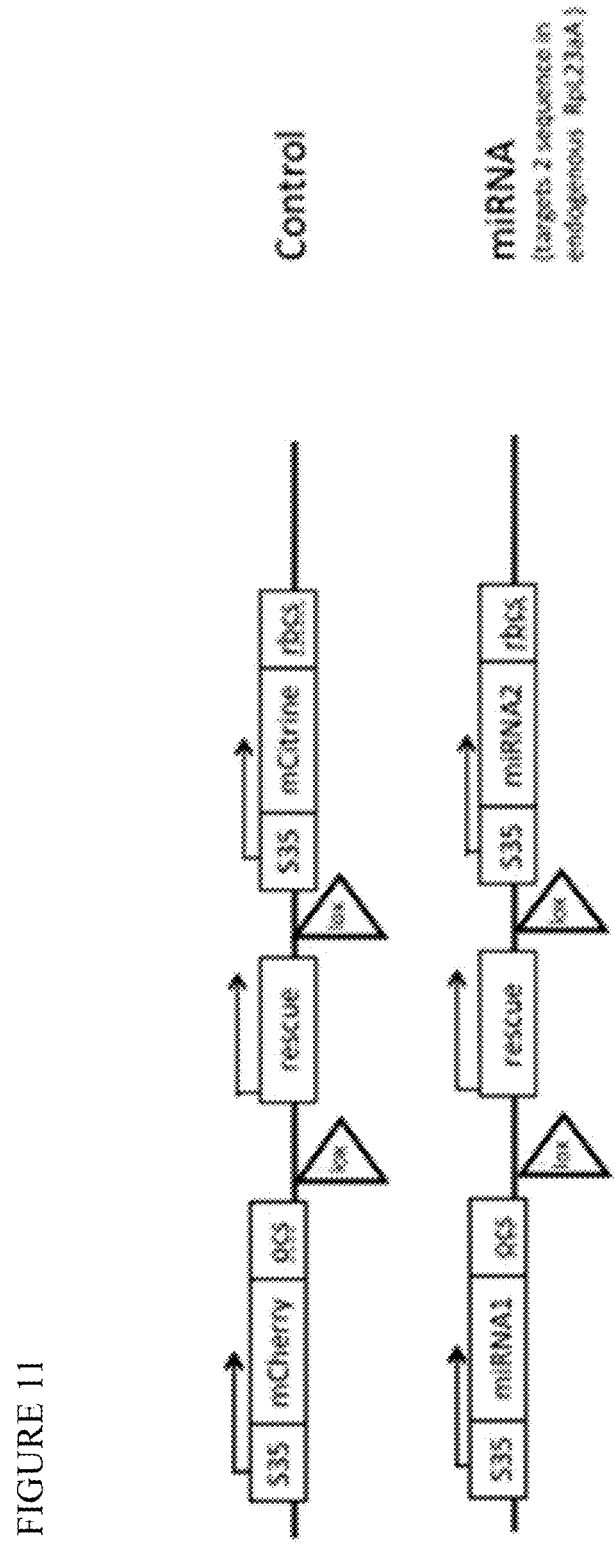
FIG. 11 depicts a scheme for a {Ud} construct targeting the *Aradabopsis thaliana* gene RpL23aA and an appropriate transformation control plasmid. S35=a promoter, OCS=terminator, rbcs=terminator, and rescue=RpL23aA gene with flanking regions where synonymous substitutions have been introduced. In the control plasmid only fluorescent proteins are expressed from the two S35 promoters while in the functional {Ud} plasmid two miRNA genes target two regions of RpL23aA are expressed. The rescue gene in both plasmids is the full RpL23aA gene including flanking regions where synonymous mutations have been introduced to render it insensitive to the targeted RNAi knock down (see also FIG. 12). Lox=CRE recombinase recognition sites which can be used to remove the rescue gene in vivo to determine the phenotype of unrescued knock-down by the miRNA genes.

For an implementation of the miRNA underdominance approach a plasmid was generated using standard laboratory cloning procedures The plasmid construction is carried out using standard cloning techniques. As shown in FIG. 11 two miRNA genes redundantly target parts of the Aradabopsis thaliana RpL23aA mRNA. This is rescued by a single complete copy of the RpL23aA gene where synonymous mutations have been introduced to render it substantially insensitive to knock-down by miRNA expression (FIG. 12). The targeted and targeting sequences can be selected using a variety of selection procedures. The miRNA approach used here follows the approach of Schwab et al The Plant Cell, Vol. 18, 1121-1133.

The invention claimed is:

1. Method for reducing the competitive fitness of an animal hemizygous for a transgenic locus compared to the animal homozygous for the transgenic locus, wherein the animal is *Drosophila melanogaster* comprising the steps of:
 (a) reducing the expression of a haploinsufficient gene in the animal, wherein said reduction is conveyed by a transgenic locus in the animal, wherein said hapoinsufficient gene is RpL14, wherein said transgenic locus comprises an underdominant construct, said underdominant construct encoding and expressing (i) a double-stranded ribonucleic acid (dsRNA) molecule that specifically inhibits expression of the haploinsufficient gene; and (ii) a modified haploinsufficient gene that is resistant to dsRNA inhibition; and
 (b) rescuing the reduced expression in the animal, wherein said rescue is conveyed by the same transgenic locus in the animal,
 wherein transformation for said reduction and said rescue is carried out simultaneously yielding an animal which is less competitively fit if hemizygous for the transgenic locus than if homozygous for the transgenic locus.

2. The method of claim 1, additionally comprising (i) the step of releasing a transgenic animal obtained in step (b) into a population of the same species such that the transgenic locus is established at a high frequency at a locus in the population; or (ii) the step of crossing a transgenic animal obtained in step (b) with otherwise interfertile sexually reproducing wildtype individuals of the animal, whereby the competitive fitness of hemizygous progeny is reduced.

3. Method for the transformation of a population of sexually reproducing animals, wherein the animal is *Drosophila melanogaster* comprising the steps of:
 (a) reducing the expression of a haploinsufficient gene in the animal, wherein said reduction is conveyed by a transgenic locus in the animal, wherein said hapoinsufficient gene is RpL14, wherein said transgenic locus comprises an underdominant construct, said underdominant construct encoding and expressing (i) a dsRNA molecule that specifically inhibits expression of the haploinsufficient gene; and (ii) a modified haploinsufficient gene that is resistant to dsRNA inhibition;

(b) rescuing the reduced expression in the animal, wherein said rescue is conveyed by the same transgenic locus in the animal, wherein transformation for said reducing and said rescuing is carried out simultaneously, and (c) releasing homozygous animals obtained in the preceding step into a population of the same species such that the transgenic locus is established at a high frequency in the population.

4. The method of claim 2, wherein said releasing step comprises the release, in a single or over multiple generations, of animals into the population to result in a frequency in population of the same species greater than the unstable allelic equilibrium frequency predicted by the competitive fitness, wherein the allelic frequency in the population exceeds 50%.

5. The method of claim 1, wherein said rescuing the expression of a haploinsufficient gene comprises a modification of the haploinsufficient gene sequence.

6. The method of claim 1, additionally comprising the steps of obtaining animals homozygous for said underdominant construct; and removing said independent transgenic construct by chromosomal recombination or segregation.

7. The method of claim 1, wherein said underdominant construct additionally comprises an effector gene.

8. The method of claim 1, wherein said animal is a disease vectoring animal.

9. The method of claim 3, wherein said rescuing the expression of a haploinsufficient gene comprises a modification of the haploinsufficient gene sequence.

10. The method of claim 3, additionally comprising the steps of obtaining animals homozygous for said underdominant construct; and removing said independent transgenic construct by chromosomal recombination or segregation.

11. The method of claim 3, wherein said underdominant construct additionally comprises an effector gene.

* * * * *

SEQUENCE LISTING

<160> NUMBER OF SEQ ID NOS: 25

<210> SEQ ID NO 1
<211> LENGTH: 21
<212> TYPE: PRT
<213> ORGANISM: Artificial Sequence
<220> FEATURE:
<223> OTHER INFORMATION: Chimeric peptide derived from Vespula lewisii
      and Homo sapiens sequences

<400> SEQUENCE: 1

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 2
<211> LENGTH: 8
<212> TYPE: PRT
<213> ORGANISM: Homo sapiens

<400> SEQUENCE: 2

Asp Arg Val Tyr Ile His Pro Phe
1               5

<210> SEQ ID NO 3
<211> LENGTH: 33
<212> TYPE: DNA
<213> ORGANISM: Artificial Sequence
<220> FEATURE:
<223> OTHER INFORMATION: Primer

<400> SEQUENCE: 3
tatgcggccg cttgattagt ttcctggcca ctt                              33

<210> SEQ ID NO 4
<211> LENGTH: 31
<212> TYPE: DNA
<213> ORGANISM: Artificial Sequence
<220> FEATURE:
<223> OTHER INFORMATION: Primer

<400> SEQUENCE: 4
tatgaattca aggcataaga gctttgaatc g                                31

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
tctttccggt tagcgtcat                                              19

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
cgccagtcag aggaccat                                               18

```
<210> SEQ ID NO 7
<211> LENGTH: 16
<212> TYPE: DNA
<213> ORGANISM: Artificial Sequence
<220> FEATURE:
<223> OTHER INFORMATION: Probe
<220> FEATURE:
<221> NAME/KEY: misc_structure
<222> LOCATION: (1)..(1)
<223> OTHER INFORMATION: Comprises FAM extension at 5' terminus

<400> SEQUENCE: 7
ttgccaaggc ctccgc                                                     16

<210> SEQ ID NO 8
<211> LENGTH: 16
<212> TYPE: DNA
<213> ORGANISM: Artificial Sequence
<220> FEATURE:
<223> OTHER INFORMATION: Probe
<220> FEATURE:
<221> NAME/KEY: misc_structure
<222> LOCATION: (1)..(1)
<223> OTHER INFORMATION: Comprises VIC extension at the 5' terminus

<400> SEQUENCE: 8
tcgccaaagc ctccgc                                                     16

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
gggccaaagt gtaaataact gg                                              22

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
aaaatgtcca ttactttggt gct                                             23

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
actttccttc cgatggacct                                                 20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
aatgaccacc gtctttcagc                                                 20
```

```
<210> SEQ ID NO 13
<211> LENGTH: 21
<212> TYPE: DNA
<213> ORGANISM: Drosophila melanogaster

<400> SEQUENCE: 13
ttacttacca gttataggca t                                              21

<210> SEQ ID NO 14
<211> LENGTH: 21
<212> TYPE: DNA
<213> ORGANISM: Drosophila melanogaster

<400> SEQUENCE: 14
tgtaagcctc acgtaaggct a                                              21

<210> SEQ ID NO 15
<211> LENGTH: 80
<212> TYPE: DNA
<213> ORGANISM: Drosophila melanogaster

<400> SEQUENCE: 15
cctttcgaga gattcgtaca aactggtcgc attgccaagg caggtaccag gccattgtcg    60
acgtcattga ccaaaacaga                                                80

<210> SEQ ID NO 16
<211> LENGTH: 102
<212> TYPE: DNA
<213> ORGANISM: Drosophila melanogaster

<400> SEQUENCE: 16
cctttcgaga gattcgtaca aactggtcgc attgccaagg cctccgccgg tcccctgaag    60
gggcgcctgg tggccattgt cgacgtcatt gaccaaaaca ga                      102

<210> SEQ ID NO 17
<211> LENGTH: 102
<212> TYPE: DNA
<213> ORGANISM: Drosophila melanogaster

<400> SEQUENCE: 17
cccttcgagc gcttcgtgca aacaggccgc atcgccaaag cctccgccgg tccccctgaag   60 gggcgcctgg tcgccatcgt cgatgtcatc gaccagaaca gg                      102

<210> SEQ ID NO 18
<211> LENGTH: 21
<212> TYPE: DNA
<213> ORGANISM: Drosophila melanogaster

<400> SEQUENCE: 18
atgcctataa ctggtaagta a                                              21

<210> SEQ ID NO 19
<211> LENGTH: 21
<212> TYPE: DNA
<213> ORGANISM: Drosophila melanogaster

<400> SEQUENCE: 19
aagcctagaa ctggtaagta c                                              21

<210> SEQ ID NO 20
<211> LENGTH: 21
```

```
<212> TYPE: DNA
<213> ORGANISM: Drosophila melanogaster

<400> SEQUENCE: 20
aagccacgta ccggaaagta c                                      21

<210> SEQ ID NO 21
<211> LENGTH: 21
<212> TYPE: DNA
<213> ORGANISM: Drosophila melanogaster

<400> SEQUENCE: 21
gttcctagaa agcctaagta c                                      21

<210> SEQ ID NO 22
<211> LENGTH: 21
<212> TYPE: DNA
<213> ORGANISM: Drosophila melanogaster

<400> SEQUENCE: 22
tagccttacg tgaggcttac a                                      21

<210> SEQ ID NO 23
<211> LENGTH: 21
<212> TYPE: DNA
<213> ORGANISM: Drosophila melanogaster

<400> SEQUENCE: 23
aaggcttacg tgaggcttac a                                      21

<210> SEQ ID NO 24
<211> LENGTH: 21
<212> TYPE: DNA
<213> ORGANISM: Drosophila melanogaster

<400> SEQUENCE: 24
aaggcttatg ttaggttgac a                                      21

<210> SEQ ID NO 25
<211> LENGTH: 21
<212> TYPE: DNA
<213> ORGANISM: Drosophila melanogaster

<400> SEQUENCE: 25
aaggcgtatg tgaggttgac t                                      21
```